US007459604B2

(12) United States Patent
Onstenk E. V. Fierens et al.

(10) Patent No.: US 7,459,604 B2
(45) Date of Patent: Dec. 2, 2008

(54) METHODS FOR GENERATING RESISTANCE AGAINST CGMMV IN PLANTS

(75) Inventors: Bernarda Gerharda Johanna Onstenk E. V. Fierens, Veenendaal (NL); Michiel Theodoor Jan De Both, Wageningen (NL)

(73) Assignee: Keygene N.V., Wageningen (NL)

(*) Notice: Subject to any disclaimer, the term of this patent is extended or adjusted under 35 U.S.C. 154(b) by 387 days.

(21) Appl. No.: 10/467,622

(22) PCT Filed: Feb. 8, 2002

(86) PCT No.: PCT/NL02/00088

§ 371 (c)(1), (2), (4) Date: Apr. 5, 2004

(87) PCT Pub. No.: WO02/063019

PCT Pub. Date: Aug. 15, 2002

(65) Prior Publication Data

US 2004/0237136 A1 Nov. 25, 2004

(30) Foreign Application Priority Data

Feb. 8, 2001 (EP) .................................. 01200448

(51) Int. Cl.
*C12N 15/82* (2006.01)
*A01H 5/00* (2006.01)
*A01H 5/10* (2006.01)

(52) U.S. Cl. ....................... 800/279; 800/285; 800/265; 800/295; 435/419; 435/468

(58) Field of Classification Search ....................... None
See application file for complete search history.

(56) References Cited

FOREIGN PATENT DOCUMENTS

| | | | |
|---|---|---|---|
| WO | WO 92/03539 | * | 3/1992 |
| WO | WO 95/04825 | * | 2/1995 |
| WO | WO 01/09300 A2 | | 2/2001 |

OTHER PUBLICATIONS

Thomas et al. Size constraints for targeting post-transcriptional gene silencing and for RNA-directed methylation in Nicotiana benthamiana using a potato virus X vector. (2001) The Plant Journal, vol. 25, pp. 417-425.*
Waterhouse et al. Virus resistance and gene silencing in plants can be induced by simultaneous expression of sense and antisense RNA. (1998) PNAS, vol. 95, pp. 13959-13964.*
Ugaki et al. THe complete nucleotide sequence of cucumber green mottle mosaic virus (SH strain) genomic RNA (1991) Journal of General Virology, vol. 72, pp. 1487-1495.*
Shi et al. Cloning and expression of Potato virus Y HC-Pro (2005) GenBank Accession AY518285, pp. 1-2.*
Tan et al. The genome structure of kyuri geen mottle mosaic tobamovirus and its comparison with that of cucumber green mottle mosaic tobamovirus. (2000) Arch. Virol.; vol. 145, pp. 1067-1079.*

* cited by examiner

*Primary Examiner*—Russell Kallis
*Assistant Examiner*—Cathy Kingdon Worley
(74) *Attorney, Agent, or Firm*—Browdy and Neimark, PLLC

(57) ABSTRACT

The present invention relates to methods for generating resistance against Cucumber Green Mottle Mosaic Virus (CGMMV) in plants, in particular in plants susceptible to infection by CGMMV, such as Cucurbitaceae species, including melon, cucumber, watermelon and bottlegourd. The methods are based on the use of genetic constructs that induce post-transcriptional gene silencing and/or use a nucleotide sequence that encodes a defective variant of the replicase of CGMMV.

17 Claims, 16 Drawing Sheets

METHODS FOR GENERATING RESISTANCE AGAINST CGMMV IN PLANTS

The present invention relates to a method for generating resistance against Cucumber Green Mottle Mosaic Virus (CGMMV) in plants, in particular in plants that are susceptible to infection by CGMMV, such as species of the Cucurbitaceae family.

The invention further relates to genetic constructs suitable or use in said method, and to CGMMV-resistant transgenic plants obtained via said method.

Methods of introducing DNA sequences into the genome of plants have been known for many years and have been widely used to alter the properties of plants varieties. Such methods are among others *Agrobacterium*-mediated transformation (Horsch et al., 1985; Rogers et al., 1986), protoplast transformation using electroporation or other techniques to introduce naked DNA molecules into the plant call (Shillito et al. 1985), and particle bombardment to introduce naked DNA molecules into plant cells or tissues (Christou et al., 1994).

Among the most important applications of plant genetic engineering are those aimed at introducing resistance genes to a wide variety of plant pests and plant pathogens, such as bacteria, fungi, nematodes, insects and viruses. Many examples of virus resistance in a wide variety of plant species have been described over the last decades (Wilson et al., 1993). The various methods to obtain virus resistance in plants through the introduction of gene sequences are either based on the use of genes of plant origin; on the use of sequences/genes derived from the viral pathogen itself (so-called pathogen-derived resistance (Wilson et al., 1993), or on the use of genes of yet different origin. Sequences originating from the viral genome can be either cloned or PCR-amplified DNA sequences obtain from the genome of DNA viruses, such as geminiviruses (Kunik et al., 1994) or the cDNA sequences obtained from the genomes of RNA viruses through the use of cDNA cloning or RT-PCR amplification.

Examples of sequences/genes of RNA viruses that have been successfully used in the engine of virus resistance in plants include:
1. cost protein genes of tobamoviruses, cucumoviruses, potyviruses, potexviruses (Beachy et al., 1990);
2. RNA dependent RNA polymerase genes (replicase genes) of tobamoviruses, cucumoviruses, potyviruses (Anderson et al., 1992; Donson et al., 1993; Audy et al., 1994);
3. nucleoprotein genes of tospoviruses (Goldbach and De Haan, 1993; Prins et al., 1994; Vaira et al., 1995);
4. movement protein genes of tobamoviruses and cucumviruses (Cooper et al, 1995).

Cucumber Green Mottle Mosaic Virus (CGMMV) is a member of the tobamovirus group and infects plant species of the Cucurbitaceae family: melon (*Cucumis melo*), cucumber (*C. sativus*), watermelon (*Citrullus vulgaris*) and bottlegourd (*Lagenaria siceraria*), but not apparently *Cucurbita pepo* (squash, pumpkin, courgette). The host range of the virus is basically restricted to members of the Cucurbitaceae and/or the diagnostic species *Datura stramonium* and *Chenopodium amaranticolor* (Hollings et al., 1975).

Several different strains can be distinguished serologically and by their response in *C. amaranticolor* and *D. stramonium* (Hollings et al., 1975) The "type strain" was originally identified in Europe and does not normally cause fruit symptoms in cucumber. Another European strain, called the cucumber aucuba mosaic strain, cucumber virus 4 or *Cucumis* virus 2A causes fruit symptoms in cucumber. A number of strains are known from Japan. In watermelon, the watermelon strain causes serious disease, whereas the Japanese cucumber strain (also called Kyuri Green Mottle Mosaic Virus) and the Yodo strain cause fruit distortions in cucumber. The CGMMV-C strain from India is a pathogen on bottlegourd and serious infectious can cause complete crop losses.

In cucumber, CGMMV causes vein clearing light and dark green leaf mottle, leaf blistering and malformation and stunted growth, seriously affecting fruit yield. The East European isolates of the aucuba mosaic strain produces bright yellow leaf mottling and fruit discoloration.

CGMMV is transmitted through seed, but mostly through mechanical infection via the roots in contaminated soil, and through foliage contact and handing of plants (Hollings et al., 1975). The virus particles are extremely stable and survive several months at normal temperatures. This stability combined with the very high infectivity through mechanical contact of the foliage is responsible for the economic importance of this virus as even one or a few infected plants in a cucumber greenhouse can eventually cause the infection and loss of the total crop. Also, infection may not only spread rapidly over a current crop, but also—due to the strong persistence of the virus—affect subsequent crops. Therefore, a CGMMV infection may require sterilization of an anti greenhouse, as well as the use of sterile tools and materials.

The complete sequence of only one isolate of CGMMV has been determined (Ugaki et al., 1991; Genbank accession numbers D12505 and D01188). This isolate "SH" had been found in infected watermelon plants in East Asia. Furthermore, the sequence of the coat protein gene of one other isolate ("W") obtained from infected watermelon is known (Meshi et al., 1983; Genbank accession numbers V01551 and J02054), as well as the sequence of the 29 kD movement protein gene of a watermelon strain (Saito et al., 1988; Genbank accession number J04332). The nucleotide sequence of the CGMMV-SH isolate shows 55 to 56% identity with tobacco mosaic virus (TMV) and tobacco mild green mosaic (TMGMV), both other members of the tobamovirus group (Ugaki et al., 1991).

As described by Ugaki et al., the genome of CGMMV consists of a single-stranded RNA molecule coding for at least four open reading frames, encoding putative proteins of 186 kD, 129 kD, 29 kD and 17.3 kD, of which the 17.3 kD ORF is known to encode the coat protein. In this respect, Ugaki et al. state "No CGMMV-encoded proteins except for the coat protein have yet been identified in vivo".

The CGMMV genome is schematically shown in FIG. 1. As can be seen therein, the ORF encoding the 186 kD protein starts at the same site as the ORF encoding the 129 kD protein, and adds a putative 57 kD polypeptide to the 129 kD ORF. The presence of this 57 kD protein alone has not been detected in infected plants. Instead, the 186 kD protein has been found, being the product of a read-through translation of the 129 kD and the 57 kD ORFs.

This 186 kD protein is thought to play a role in virus replication. Also, the 129 kD ORF is thought to encode a replicase function, whereas the 29 kD ORF is thought to encode a movement protein.

Hereinbelow, the nucleotide sequence corresponding to the ORF encoding the 129 kD protein will be referred to as "129 kD sequence", the sequence corresponding to the 186 kD readthrough protein will be referred to as "186 kD sequence", and the nucleotide sequence corresponding to the ORF encoding the 57 kD readthrough part will be referred to as "57 kD sequence". These nucleotide sequences and the corresponding protein sequences are given in the sequence listings, as further described below.

Object of the invention was to provide a method for protecting plants, in particular plants susceptible to infection with CGMMV such as species of the Cucurbitaceae family, against infection with CGMMV, and in particular against infection with strains of CGMMV prevalent in Europe, such as the strains encountered in the cultivation of cucumbers in greenhouses.

Further objects were to provide means for use in said method, in particular a genetic construct that can be used for transforming plants or plant material so as to provide transgenic plants resistant against infection with CGMMV. Further objects of the invention will become clear from the description given hereinbelow.

For these purposes, applicant has investigated the symptomatology and the nucleotide sequence of the coat protein genes of 10 European strains of CGMMV, and compared these with the SH strain described by Ugaki et al. A list of these strains, with their geographical origin and symptoms on cucumber, is given in Table 1.

TABLE 1

List of collected CGMMV-isolates with their geographical origin and symptoms on cucumber.

| CGMMV isolate | Geographical origin | Symptoms on cucumber |
| --- | --- | --- |
| 1 | Eastern Europe | vein clearing, mosaic |
| 2 | Eastern Europe | vein clearing, mosaic |
| 3 | IPO-DLO, the Netherlands | almost without symptoms |
| 4 | The Netherlands | weak leaf chlorosis |
| 5 | The Netherlands | weak leaf chlorosis |
| 6 | Proefstation Naaldwijk, the Netherlands | Chlorosis |
| 7 | Rijk Zwaan, the Netherlands | Chlorosis |
| 8 | Israel | Chlorosis |
| 9 | Almeria, Spain | chlorotic leaf spots |
| 10 | Almeria, Spain | weak leaf chlorosis |
| CGMMV-SH | Japan | strong chlorotic leaf mosaic |

It was found that the sequences for the 10 European isolates are highly homologous (i.e. homology on the nucleotide level of 97%), and show about 90% homology (on the nucleotide level) with the SH-isolate. The nucleotide sequences encoding the coat proteins of each of the isolates 1-10, as well as strain SH, are given in the sequence listings, as further described below. The corresponding phytogenetic tree is shown in FIG. 2. This shows that the European isolates can be considered to constitute a subgroup of the CGMMV species.

In the sequence listings:

SEQ ID no.1 gives the nucleotide sequence encoding the 129 kD replicase protein of CGMMV isolate 4, with the ORF of the coat protein starting with the ATG codon at bp 523-525;

SEQ ID no.2 gives the amino acid sequence of the 129 kD replicase protein of CGMMV isolate 4; with the ORF of the coat protein starting with the ATG codon at bp 523-525;

SEQ ID no.3 gives the nucleotide sequence encoding the 57 kD protein of CGMMV isolate 4, with the ORF of the coat protein starting with the ATG codon at bp 523-525;

SEQ ID no.4 gives the amino acid sequence of the 57 kD replicase protein of CGMMV isolate 4, with the ORF of the coat protein starting with the ATG codon at bp 523-525;

SEQ ID no.5 gives the nucleotide sequence encoding the 186 kD readthrough protein of CGMMV isolate 4, with the ORF of the coat protein staring with the ATG codon at bp 523-525;

SEQ ID no.6 gives the amino acid sequence of the 186 kD readthrough protein of CGMMV isolate 4, with the ORF of the coat protein staring with the ATG codon at bp 523-525;

SEQ ID no.7 gives the nucleotide sequence encoding the coat protein of CGMMV isolate 1, with the ORF of the coat protein starting with the ATG codon at bp 523-525;

SEQ ID no.8 gives the nucleotide sequence encoding the coat protein of CGMMV isolate 2, with the ORF of the coat protein starting with the ATG codon at bp 523-525;

SEQ ID no.9 gives the nucleotide sequence encoding the coat protein of CGMMV isolate 3, with the ORF of the coat protein starting with the ATG codon at bp 523-525;

SEQ ID no.10 gives the nucleotide sequence encoding the coat protein of CGMMV isolate 4, with the ORF of the coat protein starting with the ATG codon at bp 523-525;

SEQ ID no.11 gives the nucleotide sequence encoding the coat protein of CGMMV isolate 5, with the ORF of the coat protein stating with the ATG codon at bp 523-525;

SEQ ID no.12 gives the nucleotide sequence encoding the coat protein of CGMMV isolate 6, with the ORF of the coat protein starting with the ATG codon at bp 523-525;

SEQ ID no.13 gives the nucleotide sequence encoding the coat protein of CGMMV isolate 7, with the ORF of the coat protein starting with the ATG codon at bp 523-525;

SEQ ID no.14 gives the nucleotide sequence encoding the coat protein of CGMMV isolate 8, with the ORF of the coat protein starting with the ATG codon at bp 523-525;

SEQ ID no.15 gives the nucleotide sequence encoding the coat protein of CGMMV isolate 9, with the ORF of the coat protein starting with the ATG codon at bp 523-525;

SEQ ID no.16 gives the nucleotide sequence encoding the coat protein of CGMMV isolate 10, with the ORF of the coat protein starting with the ATG codon at bp 523-525;

SEQ ID no.17 gives the nucleotide sequence encoding the 129 kD replicase protein of CGMMV isolate SH;

SEQ ID no.18 gives the amino acid sequence of the 129 kD replicase protein of CGMMV isolate SH;

SEQ ID no. 19 gives the nucleotide sequence encoding the 57 kD protein of CGMMV isolate SH;

SEQ ID no.20 gives tie amino acid sequence of the 57 kD replicase protein of CGMMV isolate SH, SEQ ID no.21 gives the nucleotide sequence encoding the 186 kD readthrough protein of CGMMV isolate SH;

SEQ ID no.22 gives the amino acid sequence of the 186 kD readthrough protein of CGMMV isolate SH;

SEQ ID no.23 gives the nucleotide sequence encoding the coat protein of CGMMV isolate SH;

SEQ ID's nos. 24-40 give the nucleotide sequences of the primers used in the Examples;

SEQ ID's nos. 41-44 give the nucleotide sequences used in assembling the leader sequences used in the constructs described in the Examples;

In the above sequence listings, the nucleotide sequences given are DNA sequences, as the genetic constructs of the invention described below will usually contain or consist of a DNA. As CGMMV is an RNA virus, it will be clear to the skilled person that these sequences will occur in the virus as the corresponding RNA sequence (i.e. with U replacing T). Also, it will be clear to the skilled person that the nucleotide sequences given above may be followed—both in the virus as well as in a construct of the invention—with a suitable termination codon, i.e. TAA/UAA, TAG/UAG or TGA/UGA (not shown).

Furthermore, as will be clear to the skilled person, the nucleotide sequence encoding the coat protein win usually start with an ATG codon. For example, in SEQ ID NOs 1-16, the nucleotide sequence encoding the coat protein starts at the ATG codon at base positions 523-525. (In the nucleotide sequence of SEQ ID NOs 1-16, the nucleotide sequence encoding the coat protein is preceded by another nucleotide sequence, e.g. encoding a movement protein. Accordingly, when hereinbelow reference is made to any nucleotide sequence of SEQ ID NOs 1-16, this also explicitly includes the nucleotide sequence starting at the ATG codon at base positions 523-525 of these SEQ ID's).

A particular purpose of the invention is therefore to provide a method that can provide plants with resistance against all the strains simultaneously, and more in particular a type of resistance that is agronomically useful, i.e. that can be used to generate a resistance of an extreme nature and/or that can be used to protect (crops of) plants that are cultivated under circumstances wherein the high infectivity and persistence of CGMMV can be a major problem, such as the cultivation of cucumbers in greenhouses. When generating a resistance of an extreme nature it is preferred that not even low levels of accumulation of viral RNA in the resistant plants is tolerated.

In one aspect of the present invention, this problem is solved by transforming a plant with a polynucleotide sequence (e,g. as part of a genetic construct) that is capable of including resistance against CGMMV by a mechanism that triggers sequence-specific gene silencing. Induction of PTGS (Post-transcriptional gene silencing) is a method to obtain down-regulation of gene expression of genes homologous to the inducing sequence. It has previously been employed to down regulate endogenous genes or transgenes. The present invention employs this principle for the silencing of viral genes and more in particular CGMMV genes. The natural mechanism of PTGS is not entirely understood. Plant viruses however, have evolved to overcome or suppress PTGS in order to be infective. The efficacy of PTGS against viruses has therefor not yet proven to be a wide-spread or general mechanism. The efficacy of PTGS and similar concepts will therefore largely if not mainly depend an the evolutionary development of the plant in question as well as the virus concerned. PTGS is considered to be sequence specific and it has been theorized that induction occurs by aberrant forms of RNA homologous to the genes. Aberrant form of RNA are for example extremely high levels. Of specific RNA molecules such as appear after viral infection of plant cells. Hence, it appears that sequence-specific gene silencing is induced by either high levels of transgene transcription or by the production of aberrant RNA.

One of a number of ways of inducing sequence-specific gene silencing is by expressing in a cell sense and antisense RNA molecules. These sense and antisense RNA molecules comprise nucleotide sequences respectively homologous and complementary to at least part of the nucleotide sequence of the nucleic acid of interest. In the case the nucleic acid of interest derives from a virus, the nucleotide sequence is (art of) a viral gene, for instance a gene encoding for a coat protein, a movement gene or a replicase gene.

The sense and antisense RNA molecules may be provided as one RNA molecule, for instance in the form of one or more inverted repeat sequences. Alternatively the sense and antisense RNA molecules may be provided as (a part) of two or more RNA molecules. The sense and antisense RNA may be linked by a spacer nucleotide sequence.

Without be bound thereto, the theory is that the sense and antisense RNA are capable of forming a double stranded RNA molecule (dsRNA). The dsRNA subsequently triggers a sequence-specific RNA degradation mechanism. This phenomenon has been observed in a variety of organisms, such as *C. elegans, Drosophila* and *Arabidopsis* (see or example Chuang, Z, Marcowitz, Proc. Nat acad, Sci 2000, 97, 4985-4990). Alternatively the dsRNA causes hybrid arrest of translation of co-factors required for viral replication or the hybridization of the RNA affects intra-molecular base pairing required for viral replication. At present and for the purposes of the present invention there is no preference for either theoretical mechanism. The use of gene silencing in relation to inducing virus resistance has been described previously in a number of articles such as by Waterhouse et al. in Trends in Plant Science, 1999, 4, 452-457; Kooter et al. in Trends in Plant Science, 1999, 4, 340-347; Andrew Fire in Trends In Genetics 1999, 15, 358; Muskens et al. in Plant Molecular Biology 2000, 43, 243-260.

The present invention provides a method for generating resistance in a plant or in a plant cell or against infection with CGMMV, said method comprising at least each step of transforming said plant or plant cell with one or more polynucleotide sequence that upon (at least) transformation into a plant and transcription into RNA generates resistance against infection wit CGMMV in said plant, preferably upon (at least) transformation into a plant and transcription into RNA the polynucleotide sequence does not lead to generation of (any) replicase activity in said plant; wherein the one or more polynucleotide sequence(s) comprises a first and a second DNA sequence, wherein the first DNA sequence comprises a promoter operably linked to a first DNA region capable of being transcribed into a sense RNA molecule comprising a nucleotide sequence of at least 10 consecutive nucleotides having between 75 and 100% sequence identity with at least part of the nucleotide sequence of the genome of a CGMMV virus; and preferably a further DNA region capable of controlling transcription termination and/or polyadenylation in the plant or plant cells, whereby the further DNA region is operably linked to the first DNA region. The second DNA sequence comprises a promoter operably linked to a second DNA region capable of being transcribed into an antisense RNA molecule comprising an nucleotide sequence including at least 10 consecutive nucleotides, having between about 75% to about 100% sequence identity with the complement of at least 10 consecutive nucleotides of the sense nucleotide sequence; and preferably a further DNA region capable of controlling transcription termination and polyadenylation in the plant or plant cells, The sense and antisense RNA molecules are capable of forming a double stranded RNA region by base-pairing between the regions which are complementary. Preferably, transforming the plant with the nucleotide sequence according to the invention and transcription of the nucleotide sequence into RNA does not lead to generation of (any) replicase activity in said plant. The first and second DNA sequence are either integrated separately, for instance in different loci in the nuclear gene of the transformed cell or they are linked on one recombinant DNA (i.e. one locus) such that DNAs are integrated together in the nuclear genome of the transgenic plant cells.

In order to provide resistance in the present invention, the nucleotide sequence derived from the genome of a CGMMV virus may be from a strain of the virus that in itself is not capable of infecting the plant, but which sequence is suitable for the generation of resistance against tobamoviruses in general and CGMMV and in particular.

The polynucleotide sequence according to the invention or at least apart thereof is preferably capable of forming at least one double strained RNA molecule by complementary base pairing of at least part of the sense and antisense RNA sequences. The polynucleotide according to the present invention is in general capable of virus induced gene silencing or similar mechanisms as herein described, resulting in the generation of resistance, preferably extreme resistance of the plant cells against CGMMV.

Preferably, the first and second DNA regions, encoding the sense and antisense RNA molecule, are derived from the nucleotide sequence encoding the RNA dependent RNA polymerase of CGMMV. Other nucleotide sequences derived from CGMMV are also suitable for the generation the first and second DNA regions according to the invention, based on the presently provided nucleotide sequence of CGMMV. In a preferred embodiment, a fragment derived from a nucleotide sequence encoding a RNA dependent RNA polymerase, preferably from CGMMV, is cloned in inverted repeat orientation, separated by a stuffer fragment. Transcription of the fragment in this arrangement will produce an RNA molecule that is capable of framing a hairpin structure. These constructs are evaluated in cucumber as will be further explained in the examples below. The use of dsRNA in a method for inducing virus resistance has been previously described in WO 99/53050. In this particular case, tobacco was transformed to obtain transgenic tobacco resistant against Potato Virus Y (PVY). The experiments showed that transforming plants with specifically designed constructs that contain a PVY protease sequence in only a sense orientation or only an antisense orientation resulted in virus resistance in 4 to ca. 10% of Me total number of treated plants. Improved resistance was found when the construct contained said PVY protease sequence in both a sense orientation and an antisense orientations WO 99/53050 hence teaches that in tobacco plants that are already susceptible of being rendered resistant by either a selected sense or a selected antisense sequence of said PVY protease alone, resistance may be improved by modifying the constructs to such that they express both sense and antisense RNA sequences.

Little is known at present regarding the defense mechanism against viruses in the Cucurbitaceae family. Cucumber, as an example of the Cucurbitaceae family is known to be highly susceptible to a wide variety of viruses and has, due to this susceptibility in certain cases even been used as a diagnostic tool for the detection of viruses. It has been hypothesized that his may be due to the fact that the antiviral defense mechanisms in the Cucurbitaceae family are not well developed. In the art, hence, no knowledge is available that provides guidance to the skilled man that the mechanism for conferring resistance described in the case of PVY infections in tobacco can easily be modified or transferred to other plants, especially to the Cucurbitaceae family without undue experimentation and with a reasonable expectation of success. This holds especially in the case of the Cucumber Green Mottle Mosaic Virus, of which the nucleotide sequence has only now been made available by the present applicants.

Furthermore, WO 99/53050 provides no insight or set of teachings that cat guide the skilled man in the process of selecting the parts of the sequence of CGMMV that when transformed into a plant cell are capable of conferring resistance to other viruses than Potato Virus Y in general, and to members of the Tobamovirus group of viruses in particular. Potato Virus Y is a member of the Potyvirus group, whereas CGMMV is a member of the Tobamovirus group. Although both viral groups are characterized by viral genomes consisting of one single positive RNA strand (positive mug that the single strand RNA encodes the viral proteins directly, as opposed to viral proteins being encoded by a complementary RNA molecule synthesized from the genomic RNA stand), they employ completely different replication strategies. Potyviruses encode on their RNA one single Open Reading Frame, that upon infection in plant cells is being translated into a single large polyprotein. This polyprotein is subsequently cleaved and processed into the various functional viral proteins by protease activity provided by the polyprotein itself. WO 99/53050 teaches the use of sense and antisense nucleotide sequences derived from that part of the potyvirus genome, that encodes the protease domains. Thus, sequence-specific degradation directed toward this particular part of the potyvirus genome will at least prevent the transition of peptides with this protease activity.

Tobamoviruses in general, and CGMMV in particular, do not encode proteases or protease activity. Instead, upon infection of a plant cell with these types of viruses, tile most 5' located Open Reading Frame of the viral genome will be translated into a functional RNA dependent RNA polymerase (RdRP, also termed 'replicase'), that, in turn is capable of not only replicating the entire viral genomic RNA, but that more specifically will generate subgenomic RNA molecules from the 3' part of the viral genome. These subgenomic RNA molecules encode the more 3' located viral Open Riding Frames, from which the movement proteins and coat proteins are the translated. In view of this totally different replication strategy in Tobamoviruses, the choice of the nucleotide sequences to be employed in sense and antisense gene constructs of the present invention cannot be deduced from WO 99/53050.

In a preferred embodiment of the present invention, the sense and antisense RNA molecules may be provided as one single RNA molecule, wherein preferably but not necessarily, the sense and antisense RNA sequence may be linked together through a spacer nucleotide sequence and are capable of forming a double stranded RNA molecule, also referred to as a hairpin structure. Providing the sense and antisense RNAs in a single molecule has the advantage that the ability to form a double stranded RNA molecule will become independent from the concentrations of the sense and antisense RNAs.

The spacer nucleotide sequence is preferably located between the sense and antisense nucleotide sequence. The spacer sequence is preferred for stability of the gene constructs in the process of gene cloning. In the absence of such a spacer sequence, the RNA molecule will still be able to form a double-stranded RNA, particularly if the sense and antisense nucleotide sequence are larger than about 10 nucleotides and part of the sense and/or antisense nucleotide sequence will be used to form the loop allowing tie base-pairing between the regions with sense and antisense nucleotide sequence and formation of a double stranded RNA. There are no length limits or sequence requirements associated with the spacer region, as long as these parameters do not interfere with the capability of the RNA regions with the sense and antisense nucleotide sequence to form a double stranded RNA. Hence the spacer may comprise artificial sequences that preferably are designed to aid in formation of the loop. The spacer, in a preferred embodiment, comprises an intron. In a preferred embodiment, the spacer region varies in length from 4 to about 2000 bp, preferably from 50 to 1500 bp, more preferably from 100-1250 bp. However, as previously mentioned, may be absent in which case the sense and antisense RNAs will be directly linked to each other.

In the present invention of generating resistance, preferably extreme resistance against CGMMV, it is preferred that the genetic conduct that is used for triggering the RNA degradation mechanism is formed by a sequence that comprises a promoter, operably linked to a first DNA sequence in sense direction, optionally followed by a spacer, followed by a second DNA sequence in antisense direction, optionally followed by a DNA sequence capable of controlling transcription termination or polyadenylation.

The genetic construct of the invention encode RNA molecules capable of forming more than one secondary structures such as hairpins or stem-loop sutures. Preferably, the genetic constructs of the invention are designed that hey encode an RNA molecule capable of adopting a secondary structure of the RNA that has the lowest free energy, preferably under physiological conditions (as they may occur in the cell). In accordance with the invention, the RNA molecule to be produced in the cell is designed in such a way that at least in its lowest free energy state, which it can assume under physiological conditions (within the cell), it will comprise the desired hairpin.

As used herein "hairpin RNA" refers to any self-annealing double stranded RNA molecule. In its simplest representation, a hairpin RNA consists of a double studded stem made up by the annealing RNA strands, connected by a single stranded RNA loop, and is also referred to as a "pan-handle RNA". However, the term "hairpin RNA" is also intended to encompass more complicated secondary RNA structures comprising self-annealing double stranded RNA sequences, but also internal bulges and loops. The specific secondary structure adapted will be determined by the fee energy of the RNA molecule, and can be predicted for different situations using appropriate software such as FOLDRNA (Zuker and Stiegler, 1981).

As used herein, the term "plant-expressible promoter" or "promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No 4 or No 7, or T-DNA gene promoters. It is preferred to use a promoter that has been reported active is cucumber for example, and preferred 35S.

The term "expression of a gene" refers to the process who a DNA region which is oprerably linked to appropriate regulatory regions, particularly to a promoter, is transcribed into an RNA which is biologically active i.e., which is either capable of interaction with another nucleic acid or which is capable of being translated into a polypeptide or protein. A gene is said to encode an RNA when the end product of the expression of the gene is biologically active RNA, such as e.g. an antisense RNA, a ribozyme or a replicative intermediate. A gene is said to encode a protein when the end product of the expression of the gone is a protein or polypeptide.

As used herein, "reduction of expression of the target nucleic acid" refers to the comparison of the expression of the nucleic acid of interest in the eucaryotic cell in the presence of the RNA or chimeric genes of the invention, to the expression of the nucleic acid of interest in the absence of the RNA or chimeric genes of the invention. The expansion in the presence of the chimeric RNA of the invention should thus be lower than the expression in absence thereof, preferably be only about 25%, particularly only about 10%, more particularly only about 5% of the expression of the target nucleic acid in absence of the chimeric RNA, especially the expression should be completely inhibited for all practical purposes by the presence of the chimeric RNA or the chimeric gene encoding such an RNA. The present invention preferably provides for sequence specific RNA degradation mechanism that leads to the essential annihilation of the viral genome.

A nucleic acid of interest is "capable of being expressed", when said nucleic acid, when introduced in a suitable host cell, particularly in a plant cell, can be transcribed (or replicated) to yield an RNA, and/or translated to yield a polypeptide or protein in that host cell.

As used herein "a nucleic acid of interest" or a "target nucleic acid" refers to any particular RNA molecule or DNA sequence which may be present in a eucaryotic cell, particularly a plant cell. The term "gene" means any DNA fragment comprising a DNA region (the "transcribed DNA region") that is transcribed into a RNA molecule (e. g., an mRNA) in a cell operably linked to suitable regulatory regions, e. g., a plant-expressible promoter. A gene may thus comprise several operably linked DNA fragments such as a promoter, a 5' leader sequence, a coding region, and a 3' region comprising a polyadenylation site. A plant gene endogenous to a particular plant species (endogenous plant gene) is a gene which is naturally found in that plant species or which can be introduced in that plant species by conventional breeding. A chimeric gene is any gene which is not normally found in a plant species or, alternatively, any gene in which the promoter is not associated in nature with part or all of the transcribed DNA region or with at least one other regulatory region of the gene.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983) using a window-size of 20 nucleotides, a word length of 4 nucleotides, and a gap penalty of 4. Computer-assisted analysis and interpretation of sequence data, including sequence alignment as described above, can, a. g., be conveniently performed using the programs of the Intelligentics Suite (Intelligenetics Inc., C.A.). Sequences are indicated as "essentially similar" when such sequence have a sequence identity of at leas about 75%, particularly at least about 80%, more particularly at least about 85%, quite particularly about 90%, especially about 95%, more especially about 100%, quite especially are identical. It is clear than when RNA sequences are said to be essentially similar or have a certain degree of sequence identity with DNA sequences, thymine (T) in the DNA sequence is considered equal to uracil (U) in the RNA sequence.

It is an object of the invention to provide a virus resistant plant, comprising a first and second chimeric DNA integrated in the nuclear genome of at least some of its cells, wherein the first chimeric DNA comprises a plant-expressible promoter, operably liked to a first DNA region capable of being transcribed into a sense RNA molecule comprising a nucleotide sequence of at least 10 consecutive nucleotides having between 75 and 100% sequence identity with at least part of the nucleotide sequence of the genome of a virus capable of infecting the plant, and optionally a DNA region involved in transcription termination and polyadenylation functioning in plant cells. The second chimeric DNA comprises a plant-expressible promoter, operably linked to a second DNA region capable of being transcribed into an antisense RNA molecule comprising an antisense nucleotide sequence including at least 10 consecutive nucleotides, having between about 75% to about 100% sequence identity with the complement of the at least 10 consecutive nucleotides of the sense nucleotide sequence, and optionally a DNA region involved in transcription termination and polyadenylation functioning in plant cells. Preferably the at least 10 nucleotides share sequence identity with part of the vial genome that encodes a replicase function, and more preferably the virus is a CGMMV.

The sense and antisense RNA molecules are capable of forming a double stranded RNA region by base-pairing between the regions which are complementary. The first and second chimeric DNA are integrated either in one locus or in different loci in the nuclear genome.

In a preferred embodiment of the invention, the RNA molecule transcribed from the chimeric gene, consists essentially of the hairpin RNA.

In a preferred embodiment, the order of the sense and antisense nucleotide sequence in the RNA molecule is not critical.

Thus, in other words, the chimeric DNA ha a transcribed DNA region, which when transcribed, yields a RNA molecule comprising an RNA region cable of forming an stem-loop structure, wherein one of the annealing RNA sequences of the stem-loop structure comprises a sequence, essentially similar to at least part of the nucleotide sequence of the nucleic acid of interest, and wherein the second of the annealing RNA sequences comprises a sequence essentially similar to at least part of the complement of at least part of be nucleotide sequence of the nucleic acid of interest. The RNA molecule may comprise more than one hairpin structures, which may be designed to reduce the expression of different nucleic acids of interest.

In a preferred embodiment, the nucleic acid of interest, whose expression is targeted to be reduced or whose degradation is desired, is a viral nucleic acid, particularly a viral RNA molecule, more in particular a tobamovirus, most in particular a CGMMV RNA molecule capable of infecting a eulcaryotic cell, particularly a plant cell. In a preferred embodiment, the expression to be reduced is the replication of the virus and/or the degradation of the viral DNA. It is also preferred to reduce or to remove the disease symptoms caused by the infecting virus. The reduction of expression or the degradation of other genes from CGMMV such as the genes encoding for movement proteins or coat proteins or the degradation of other viral nucleic acid sequences or the degradation of subgenomic RNAs is also explicitly included within the scope of the present invention.

Preferably, the nucleotide sequence of the target nucleic acid corresponding to the sense nucleotide sequence is part of a DNA region which is transcribed, particularly a DNA region which is transcribed and translated (in other words a coding region). It is particularly preferred that the target sequence corresponds to one or more consecutive exons, more particularly is located within a single exon of a coding region.

The length of the sense nucleotide sequence may vary from about 10 nucleotides (nt) up to a length equaling the length (in nucleotides) of the target nucleic acid. Preferably the total length of the sense nucleotide sequence is at least 10 nt, preferably 15 nt, particularly at least about 50 nt, more particularly at least about 100 nt, especially at least about 150 nt, more especially at least about 200 nt, quite especially at least about 550 nt. In principle there is no upper limit for the total length of the sense nucleotide sequence, other than the total length of the target nucleic acid. However for purely practical reason (such as e. g. stability of the chimeric genes, ease of manipulating the genetic constructs) the length of the sense nucleotide sequence should preferably not exceed 5000 nt, more preferably should not exceed 2500 nt and may preferably be limited to about 1000 nt.

It will be appreciated that the longer the total length of the sense nucleotide sequence is, the less stringent the requirements for sequence identity between the total sense nucleotide sequence and the corresponding sequence in the target gene become. Preferably, the total sense nucleotide sequence should have a sequence identity of at least about 75% with the corresponding target sequence, particularly at least about 80%, more particularly at least about 85%, quite particularly about 90%, especially about 95%, more especially about 100%, quite especially be identical to the corresponding part of the target nucleic acid. However, it is preferred that the sense nucleotide sequence always includes a sequence of about 10 consecutive nucleotides, particularly about 20 nt, more particularly about 50 nt, especially about 100 nt, quite especially about 150 nt with 100% sequence identity to the corresponding part of the target nucleic acid. Preferably, for calculating the sequence identity and designing the corresponding sense sequence, the number of gaps should be minimized, particularly for the shorter sense sequences.

The length of the antisense nucleotide sequence is largely determined by the lengths of the sense nucleotide sequence, and will preferably correspond to the length of the latter sequence. However, it is possible to use an antisense sequence which differs in length by about 10%. Similarly, the nucleotide sequence of the antisense region is largely determined by the nucleotide sequence of the sense region, and preferably is identical to the complement of the nucleotide sequence of the sense region. Particularly with longer antisense regions, it is however possible to use antisense sequences with lower sequence identity to the complement of the sense nucleotide sequence, preferably with at least about 75% sequence identity, more preferably with at least about 80%, particularly with at least about 85%, more particularly with at least about 90% sequence identity, especially with at least about 95% sequence to the complement of the sense nucleotide sequence. Nevertheless, it is preferred that the antisense nucleotide sequences always includes a sequence of about 10, preferably 15 consecutive nucleotides, particularly about 20 nt more particularly about 50 nt, especially about 100 nt, quite especially about 150 nt with at least 80%, preferably at leas 90% more preferably at least 95% and most preferred 100% sequence identity to the complement of a corresponding part of the sense nucleotide sequence. Again, preferably the number of gaps should be minimized, particularly for the shorter antisense sequences. Further, it is also preferred that the antisense sequence has between about 75% to 100% sequence identity with the complement of the target sequence.

In a preferred embodiment the hairpin RNA formed by the sense and antisense region and if appropriate the spacer region, is an hairpin RNA.

By "artificial hairpin RNA" or "artificial stem-loop RNA structure", is meant that such hairpin RNA is not naturally occurring in nature, because the sense and antisense regions as defined are not naturally occurring simultaneously in one RNA molecule, or the sense and antisense regions are separated by a spacer region which is heterologous with respect to the target gene, particularly, the nucleotide sequence of the spacer has a sequence identity of less than 75% with the nucleotide sequence of the target sequence, at the corresponding location 5' or 3' of the endpoints of the sense nucleotide sequence. A hairpin RNA can also be indicated as artificial, if it is not coded within the RNA molecule it is nay associated with. It is conceivable to use in accordance with the invention a chimeric DNA whose transcription results in a hairpin RNA structure with a naturally occurring nucleotide sequence (which otherwise meets he limits as set for i this specification) provided this hairpin RNA is devoid of the subsiding RNA sequences (not involved in the hairpin structure formation).

Although it is preferred that the RNA molecule comprising the hairpin RNA does not further comprise an intron sequence, it is clear that the chimeric DNA genes encoding such RNAs may comprise in their transcribed region one or more introns.

The transformed plant cells are preferably used for the generation of transformed plants that can be fisher used in conventional breeding schemes to provide for more plants or to introduce the desired transformation, in the present invention resistance against CGMMV, to other varieties of the same or related plant species or in hybrid plants. Seeds obtained from the transformed plants containing the chimeric genes of the invention are also encompassed within the presently claimed scope.

As herein defined, with "inverted repeat sequence" is meant a DNA or RNA sequence that contains two identical nucleotide sequences in opposite directions (i.e. sense and anti-sense). The identical nucleotide sequences may be divided by a spacer. Identical in this respect is to be seen in the terms of sequence identity as herein defined.

The RNA sequence of the viral genome that may be used in the design of a suitable construct for use in the present invention preferably comprises nucleotides sequences that are derived from nucleotides sequences of the virus of interest, in the present case and preferably CGMMV, encoding (part(s) of) the movement, coat and/or replicase proteins, of which nucleotide sequences coding for the replicase protein are most preferred. However, other nucleotide sequences that can be expressed such that resistance is conferred by virus-derived transgenes are included within the present invention. Such nucleotide sequences are sequences that are homologous, preferably functionally homologous, to the sequences of the present invention. The term homologous in terns of the present invention indicates a certain amount of sequence identity on the nucleotide level. 100% homology indicates that the sequences are 100% identical. Sequences are also considered homologous if one or more nucleotides from the sequence are deleted, added or replaced as long as a certain percentage of sequence identity remains, for instance with a most preferred limit of 99%, more preferably 95, 85, 80, preferably 75, 70 or 65%. Also percentages as low as 50 or 60% may very well be considered as homologous. Whether or not a sequence can be regarded as homologous also depend on the function of that sequence. For instance a nucleotide e sequence encoding for a protein will still be considered as homologous if the protein it encodes for is able to perform its function. Hence homology is present if the functionality is maintained, thereby allowing for well known principles as degeneracy. By the term "functionally homologous" is meant the following. A sequence (for instance a gene) is considered functionally homologous if that sequence (gene) is homologous to another sequence, hence at least one nucleotide is deleted, inserted, replaced such as inversed (in case of more than one nucleotide) or transversion or transition while the function of said sequence (gene) is substantially maintained. This may also apply to chemically modified sequences. When a sequence is functionally homologous, there may very well be a low percentage of homology, but the functionality of that sequence is substantially maintained. Such sequences, whether DNA or RNA are also included within the scope of the present invention.

In a preferred embodiment, the sequence used to design the construct of the present invention is the "nucleotide sequence encoding a defective variant of the replicase gene of CGMMV" as herein defined.

In another aspect of the present invention, this problem is solved by transforming a plant with a polynucleotide sequence (e.g. as part of a genetic construct) that can provide the plant with so-called "replicase-mediated" resistance against CGMMV. In particular, this will be a polynucleotide sequence that i) has been derived from the 129 kD sequence, the 57 kD sequence, or the 186 kD readthrough sequence of native CGMMV;

ii) upon (at least) transformation into the plant and transcription into RNA —and usually also translation into the corresponding encoded protein—can provide the plant with resistance against CGMMV; but iii) does not encode any replicase activity.

In one aspect of the invention, in case of the "replicase-mediated" resistance, a polynucleotide sequence according to the invention can encode a polypeptide or protein that is capable of providing a plant with resistance against GCMMV, but that by itself has no replicase activity, for resistance due to one or more alterations in its amino acid sequence, compared to the amino acid sequence encoded by the 129 kD sequence, 57 kD sequence, and/or 186 kD readthrough sequence of native CGMMV.

However, according to one specific embodiment of the invention, the polynucleotide sequence may also comprise, or even consist of the native 57 kD sequence.

In one aspect, the invention therefore relates to a method for generating resistance in a plant against CGMMV, said method comprising at least the step of transforming said plant with a polynucleotide encoding a defective variant of the replicase gene of CGMMV.

In a further aspect, the invention also relates to a method for providing a transgenic plant and/or plant cell that is resistant against infection with CGMMV, comprising at least the step of transforming said plant or plant cell with a polynucleotide sequence encoding a defective variant of the replicase gene of CGMMV.

In another aspect, the invention also relates to a genetic construct suitable for transforming a plant, said construct at least comprising a polynucleotide sequence encoding a defective variant of the replicase gene of CGMMV, and optionally further elements of genetic constructs known per se. The invention also relates to a plant, plant cell and/or plant material that has been transformed with a genetic construct of the invention.

The invention also relates to transgenic, plants that contain a polynucleotide sequence encoding a defective variant of the replicase gene of CGMMV, and/or that have been provided with resistance against infection with CGMMV by the method of the invention.

In the context of the invention, by the "replicase gene of CGMMV" is meant the native 129 kD sequence, the native 57 kD sequence, and/or the combined native 186 kD "readthrough" product of the native 129 kD and native 57 kD sequences.

By a "native" sequence is meant any RNA sequence that naturally occurs in CGMMV, including all isolates and strains thereof, as well as any DNA sequence that corresponds to these naturally occurring RNA sequences. Examples of such native sequences are the 129 kD nucleotide sequences given in SEQ. ID no.1 and SEQ. ID no.17, the 57 kD nucleotide sequences given in SEQ. ID no.3 and SEQ. ID no.19 and the 186 kD nucleotide sequences given in SEQ. ID no.5 and SEQ. ID no.21. It will be clear to the skilled person that there may be (further) naturally occurring variants of the RNA sequence from which the DNA sequences in the sequence listings were derived, and these (and the DNA sequences corresponding thereto) are also included within the term "native sequence".

By "a polynucleotide sequence encoding a defective variant of the replicase gene of CGMMV" in its broadest sense is meant a polynucleotide sequence that
   i) upon (at least) transformation into a plant and transcription into RNA generates resistance against infection with CGMMV in said plant; and
   ii) upon (at least) formation into a plant and transcription into RNA does not lead to generation of (any) replicase activity in said plant (or at least—when it does lead to expression of some replicase activity—leads to expression of a replicase activity that is severely reduced compared to expression of the native gene encoding CGMMV replicase).

Herein, the terms "plant", "transformed plant" and/or "transgenic plant" include all parts or tissues of such a plant, including but not limited to individual cells of such a plant. These terms also includes material of or for such a plant, such as material that can be regenerated into a (mature) plant, including but not limited to protoplasts and/or callus tissue, or material that can be cultivated into a mature plant, such as cultivation material.

The plant is preferably a pit that is susceptible to infection with CGMMV, more preferably a plant belonging to the Cucurbiteceae family, such as melon (*Cucumis melo*), cucumber (*C. sativus*), watermelon (*Citrullus vulgaris*) and bottlegourd (*Lagenaria siceraria*).

Included within the term "CGMMV" are all known strains thereof, including those prevalent in Europe and Asia. In particular, the method of the invention can be used to protect plants against strains of CCMMV prevalent in Europe (including Israel), such as those which are a problem in the cultivation of melons and in particular cucumbers in greenhouses, although the invention is not limited thereto.

In doing so, a major advantage of the invention is that it can provide protection against several and preferably all, (such) strains of CGMMV simultaneously. Another advantage of the invention is that it provides "absolute" protection against CGMMV, which means that— upon expression of a polynucleotide sequence encoding a defective replicase in a plant— essentially no viral particles can be detected in the transformed plant (material). The method of the invention therefore does not lead to a deferral or slowing down of the onset of symptoms, as may occur when so-called "coat protein-mediated" resistance is used. Also, the method of the invention leads to a high level of resistance, and may also have the advantage of a favorable temperature effect. Usually, the "nucleotide sequence encoding a defective variant of the replicase gene of CGMVV" will be a nucleotide sequence in which—compared to a nucleotide sequence encoding the corresponding native replicase of CGMMV—one or more nucleotides have been added, replaced and/or removed. In particular, the "nucleotide sequence encoding a defective variant of the replicase gene of CGMMV may be a nucleotide sequence that comprises, and preferably consists of:
   a nucleotide sequence corresponding to the native 129 kD sequence in which—compared to said native sequence—one or more nucleotides have been added, replaced and/or removed;
   a nucleotide sequence corresponding to the native 186 kD sequence in which—compared to said native sequence—one or more nucleotides have been added, replaced and/or removed, e.g. in the part of the native 186 kD sequence corresponding to the 129 kD sequence, to the 57 kD sequence, or both;
   a nucleotide sequence corresponding to the native 57 kD sequence;
   a nucleotide sequence corresponding to the native 57 kD sequence in which—compared to said native nucleotide—one or more nucleotides have been added, replaced and/or removed;
   such that said nucleotide sequence is capable—upon (at least) transformation into a plant and transcription into RNA—to confer to said plant resistance against infection with CGMMV, and such that said nucleotide sequence—upon (at least) transformation into a plant and transcription into RNA—is not capable of generating of (any) replicase activity in said plant.

Usually, the "nucleotide sequence encoding the defective variant of the replicase gene of CGMWV" will encode a protein or polypeptide, more specifically a protein or polypeptide that:
   1) upon being expressed in a plant is capable of generating resistance against CGMMV in said plant; and
   2) upon being expressed in a plant has no replicase activity (or —when it has some replicase activity—has severely reduced replicase activity compared to the native CGMMV replicase).

Such a protein or polypeptide will be generally referred to hereinbelow as "defective replicase"; and a polynucleotide sequence encoding such a protein or polypeptide will be referred to as a "polynucleotide sequence encoding a defective replicase".

Usually, the defective replicase will be a derivative—such as an analog, homolog, variant, mutant, part fragment or combination of two or more such parts or fragments, etc.—of the amino acid sequence encoded by the native 129 kD sequence, the native 186 kD sequence and/or the native 57 kD sequence, in which—compared to the amino acid sequence encoded by the corresponding native sequence—one or more amino acids have been added, replaced or removed, preferably replaced or removed, more preferably removed, leading to loss of replicase activity (or at least an inability to generate replicase activity when expressed in the plant).

In particular, the defective replicase may be a protein or polypeptide that comprises, and preferably consists of:
   an amino acid sequence corresponding to the amino acid sequence encoded by the native 129 kD sequence, in which—compared to said native sequence —one or more amino acids have been added, replaced or removed, preferably replaced or removed, more preferably removed;
   an amino acid sequence corresponding to the amino acid sequence encoded by the native 186 D sequence, in which—compared to said native sequence —one or more amino acids have been added, replaced or removed, preferably replaced or removed, more preferably removed, leading to loss of replicase activity;
   an amino acid sequence corresponding to the ammo acid sequence encoded by native 57 kD sequence;
   an amino acid sequence corresponding to the amino acid sequence encoded by the native 57 kD sequence, in which—compared to said native sequence—one or more amino acids have been added, replaced or removed, preferably replaced or removed, more preferably removed;
   or any combination thereof, provided that the resulting protein or polypeptide shows no replicase activity, but is still capable—upon expression in a plant—to generate resistance against CGMMV in said plant.

More in particular, the defective replicase may be a protein or polypeptide that comprises, and preferably consists of:

- an amino acid sequence corresponding to a part or fragment of the amino acid sequence encoded by the native 129 kD sequence, or to a combination of two or more such parts or fragments;
- an amino acid sequence corresponding to a part or fragment of the amino acid sequence encoded by the native 186 kD sequence, or to a combination of two or more such parts or fragments; or
- an amino acid sequence corresponding to the amino acid sequence encoded by the native 57 kD sequence.

such that the resulting protein or polypeptide shows no replicase activity, but is still capable—upon expression in a plant—to generate resistance against CGMMV in said plant.

An amino acid sequence "corresponding to apart or fragment of the amino acid sequence encoded by the native 186 kD sequence, or to a combination of two or more such parts or fragments" may for instance comprise: i) at least one part or fragment of the amino acid sequence encoded by the native 129 kD sequence combined with at least one part or fragment of the amino acid sequence encoded by the native 57 kD sequence (which combination of parts or fragments may or may not correspond to a contiguous amino acid sequence encoded by the native 186 kD sequence); ii) at least one part or fragment of the amino acid sequence encoded by the native 129 kD sequence combined with the full amino acid sequence encoded by the native 57 kD sequence, and/or iii) at least one part or fragment of the amino acid sequence encoded by the fill native 129 kD sequence combined with at least one part or fragment of the amino acid sequence encoded by he native 57 kD sequences.

It is know however, that expression in a plant of a nucleotide sequence encoding the full 129 kD sequence of the native replicase usually does not provide resistance against infection with CGMMV, but may even—upon infection of the plant—promote or facilitate multiplication of the virus. Therefore, in one embodiment the invention does not comprise the expression in a plant of said replicase, nor the use of a polynucleotide sequence encoding such a replicase.

Even more preferably, the defective replicase is a protein or polypeptide that consists of;

- an amino acid sequence corresponding to a part or fragment of the amino acid sequence encoded by the native 129 kD sequence, or a combination of two or more such parts or fragments; such that the resulting protein or polypeptide shows no replicase activity, but is still capable, upon expression in a plant, to generate resistance against CGMMV in said plant, or
- an amino acid sequence corresponding to the amino acid sequence encoded by the native 57 kD sequence.

Any such parts or fragments may also contain one or more further amino acid substitutions, insertions or deletions compared to the native sequence, but this is not preferred.

Most preferably, the defective replicase is a so-called "truncated replicase", i.e. an amino add sequence corresponding to the amino acid sequence encoded either by the 129 kD sequence and/or by the 186 kD sequence, from which—compared to the native amino acid sequence—one or more amino acid residues are lacing at the carboxyl-terminus, such that the resulting protein or polypeptide shows no replicase activity, but is still capable—upon expression in a plant—to generate resistance against CGMMV in said plant. (In case of a truncated replicase based upon the 186 kD sequence, this usually means that the resulting protein will contain the fill acid sequence of the 129 kD sequence, as well as part of the amino acid sequence of the 57 kD sequence (i.e. that is contiguous to the 129 kD sequence in the amino acid sequence encoded by native 186 kD sequence), with one or more amino acids lacking at the carboxy-terminus of the 57 kD part, although the invention in its broadest sense is not limited thereto).

The polynucleotide sequence that encode such a truncated replicase may either comprise, or preferably consist of, the full native 129 kD sequence or 186 kD sequence, respectively, in which a stopcodon has been introduced at a desired site, or a polynucleotide sequence from which—compared to the full native 129 kD sequence or 186 kD sequence, respectively—one or more codons coding for the carboxy-terminal amino acid residues have been removed, i.e. starting from the 3' end of the native sequence(s).

As mentioned below, preferably a stopcodon is introduced in to the native sequence, in particular in the so-called GDD motive or in the P-loop. Examples thereof are the polynucleotide sequences comprised in the vectors shown in FIGS. 3-8, and as described in the Experimental Part.

Again, any such truncated replicase may also contain one or more amino acid substitutions, insertions or deletions compared to the native sequence, but this is not preferred.

As mentioned above, (the polynucleotide sequence encoding) the defective replicase is such that—after expression in a plant or plant cell—it is still capable of generating resistance against CGMMV in said plant. Usually, this means that the defective replicase will have at least one biological function that allows the defective replicase to protect the plant against CGMMV infection, such as for example down-regulation of viral replication or interference with the replication of the wild-type CGMMV, for instance by competing with wild-type virus for the replication machinery in the plant (cell). It will be clear that in order to achieve such a biological function, the defective replicase must usually have a certain minimal level of amino acid similarity wit the amino acid sequences encoded by the native 129 kD, 186 kD and/or 57 kD sequences. In so far as the defective replicase is similar to the corresponding native amino acid sequence, this may be because it contains—on the corresponding amino acid positions—the same amino acid residues as the native amino acid sequence, or amino acid residues comparable thereto. The latter will usually comprise so-called "conservative" amino acid substitutions, for instance involving replacing a given acidic or basic amino acid residue by another acidic or basic amino acid residue.

However, there will also be dies in amino acid sequence between the defective replicase and the native replicase (i.e. the 129 kD, 186 kD or 57 kD protein), such it the defective replicase will no longer provide replicase activity. The skilled person will be able to select appropriate alterations to the amino acid sequence of the native replicase. As will be clear to the skilled person, a single (amino acid or nucleotide) alteration may be sufficient, or two or more such alterations may be required, dependant upon the position and nature of the alteration(s) compared to the ammo acid sequence of the native replicase.

Whether a given polynucleotide sequence encodes a defective replicase according to the invention—or at least is capable of protecting a plant against infection with CGMMV—can simply be tested by transforming a plant, plant cell or plant material with a construct containing said polynucleotide sequence, and then exposing the plant, plant cell, plant material, and/or a mature plant generated therefore, to CGMMV under conditions such that infection may occur. It can then be easily determined whether the polynucleotide sequence/construct is capable of protecting the plant, i.e. by suitably determining the presence of the virus, or simply by the presence or absence of symptoms of CGMMV-infection.

In general, as a minimum, when the defective replicase contains my amino acid substitutions or insertions, it will have amino acid homology (i.e. identity on corresponding position) with the corresponding native replicase protein of at least 80%, preferably at least 90%, more preferably at least 95%, with amino acid deletions not being taken into account, and a single amino acid insertion being counted as a single alteration.

In general, as a minimum, when the defective replicase contains one or more amino acid deletions, it will usually contain at least 30%, preferably at least 50%, more preferably at least 70%, and usually 80-90%, and may even contain as much as 95-99%, of the amino acid sequence of the corresponding native replicase protein, with any amino acid insertions or substitutions not being taken into account.

A truncated replicase based upon the 129 kD sequence will usually contain at least 50%, preferably at least 70%, and may contain as much as 80-95%, of the amino acid sequence of the native replicase. A truncated replicase based upon the 186 kD sequence may contain the full 129 kD protein followed by one or more amino acids from the 57 kD sequence, and usually contains the full 129 kD sequence followed by 1-95%, preferably 5-50%, of the 57 kD sequence.

The differences in acid sequence mentioned above can be differences compared to any of tie amino acid sequences given in SEQ ID's 2, 4, 6 and/or 18, 20, 22, and/or compared to any naturally occurring variant of these amino acid sequences. These differences are at least such that the resulting protein does not correspond to a naturally occurring/native protein (including those given in SEQ ID's 2, 4, 6 and/or 18, 20, 22).

The polynucleotide sequences used in the invention am such that they encode the above defective replicases. For this purpose, they may contain the same codons as in the corresponding positions on the native 129 kD, 186 kD and/or 57 kD sequence, or codons equivalent thereto due to the degeneracy of the genetic code.

The polynucleotide sequence encoding the defective replicase can be provided in a manner known per se, for instance starting from the known sequence of the native 129 kD, 57 kD and/or 186 kD sequences, and/or from a nucleic acid that encodes said sequences. Usually, this will involve introducing one or more deletions, substitutions and/or insertions of one or more nucleotides, or even of one or more codons into, or compared to, the native sequence. Such deletions, substitutions and/or insertions will be collectively referred to hereinbelow as "alterations".

Accordingly, the polynucleotide sequence encoding the defective replicase may be a sequence that contain one or more such alterations compared to any of the nucleotide sequences given in SEQ ID's 1, 3, 5 and/or 17, 19, 21, and/or compared to any naturally occurring variant of these nucleotide sequences (including DNA sequences corresponding to the RNA sequences as present in the virus). These differences are at least such that the protein encoded by the polynucleotide sequence does not correspond to a naturally occurring/native protein (including those given in SEQ ID's 2, 4, 6 and/or 16, 18, 22).

Furthermore, besides the alterations mentioned above, and compared to nucleotide sequences given in SEQ ID's 1, 3, 5 and/or 17, 19, 21 and/or compared to any naturally occurring variant of these nucleic acid sequences (including DNA sequences corresponding to the RNA sequences as present in the virus), the polynucleotide sequences may ether contain one or more alterations that lead to a codon that encodes the same amino acid as the codon given for the corresponding position in SEQ ID's 1, 3, 5 and/or 17, 19, 21, and this may even lead to a fully or totally artificial and/or synthetic sequence. Also, compared to nucleotide sequences given in SEQ ID's 1, 3, 5 and/or 17, 19, 21 and/or compared to any naturally occurring variant of these nucleic acid sequences (include DNA sequences corresponding to the RNA sequences as present in the virus), the polynucleotide sequences may further contain one or more alterations that lead to a conservative amino acid substitution, i.e. as mentioned above.

Providing a polynucleotide sequence that contain the desired alterations will be within the skill of the artisan and can involve techniques such as nucleic acid synthesis using an automated nucleic acid synthesis technique; introduction of (point)mutations into a nucleic acid that comprises the native 129 kD, 57 kD, and/or 186 kD sequences; and/or using or suitably combining parts or gents of the 129 kD, 57 kD and/or 186 kD sequences, or any combination thereof. Also, in providing such a polynucleotide sequence, the skilled person may take into account the degeneracy of the genetic code and/or conservative amino acid substitutions, as mentioned above.

In order to provide a polynucleotide sequence that encodes a truncated replicase as defined above, a technique involving the introduction of a stopcodon into the native sequence is particularly preferred.

A particularly preferred technique of introducing the above alterations—including stopcodons—involves the use of a PCR reaction, in which the desired alterations are introduced into the amplified sequence(s) by the use of modified primers, i.e. primers that contain a suitable "mismatch" compared to the template sequence, leading to the desired alteration in the amplified sequence. This PCR-based technique may also be used to introduce one or more restriction sites into the amplified sequence in order to facilitate the cloning of the amplification products into the desired transformation on vectors.

As further described in the Experimental Part, this may involve a single PCR-reaction, but may also involve two or more PCR, reactions, each leading to a pat of intended final sequence encoding the defective replicase in which the priers (e.g. with the desired alteration) form the ends of the fragments. These fragments may then be combined, for instance to provide a polynucleotide sequence that comprises a combination of such fragments, and/or to reconstitute the full 129 kD, 57 kD and/or 186 kD sequence, now containing the desired alteration compared to the native sequence, such as a stopcodon.

The PCR-reactions and the further steps following amplification, such as combining/joining the amplified sequences, can be carried out in a manner known per se, for instance as described in the Experimental Part and/or using the techniques described in U.S. Pat. No. 4,683,202; Saiki et al., Science 239 (1988), 487-491 or PCR Protocols, 1990, Academic Press, San Diego, Calif., USA.

As the template for the PCR-reaction a nucleic sequence encoding the native 129 kD, 57 kD and/or 186 kD sequence can be used, such as a cDNA derived from the native RNA sequence, or a plasmid containing such a sequence, including those described in the Experimental Part. The template used may itself already contain one or more alterations, compared to the corresponding native sequence.

As mentioned above, a preferred alteration involves the introduction of a stopcodon into the native 129 kD or 186 kD sequence, such that—upon transformation into a plant—the polynucleotide sequence thus obtained causes expression of a truncated replicase. In particular, such a stopcodon may be introduced into a sequence corresponding to the native 129 kD sequence, more in particular to that part of the native sequence that corresponds to the so-called GDD-motivee or to the so-called P-loop.

The polynucleotide sequence encoding the defective replicase is preferably in the form of—e.g. forms part of and/or is incorporated within—a genetic construct. The genetic construct is preferably a construct suitable for the transformation of a plant, plant cell and/or plant material, such as a plasmid, cosmid or vector, including co-integration vectors or binary vectors. The genetic construct may be DNA or RNA, and is preferably dsDNA.

Preferably the genetic construct comprising the polynucleotide sequence encoding for the defective replicase is combined with the genetic construct comprising the polynucleotide sequence encoding for the hairpin sequence. By providing plants with these omnipotent constructs resistance can be generated against different strains of a virus, preferably the CGMMV virus, depending on the vulnerability of a strain for a particular method of generating resistance.

Such a construct may further contain all known elements for genetic constructs, and in particular for genetic constructs intended for the transformation of plants, as long as the presence thereof does rot interfere with the CGMMV resistance to be provided by the polynucleotide sequence encoding the defective replicase. Some non-limiting examples of such elements include leader sequences, terminators, enhancers, integration factors, selection markers, reporter genes, etc., and suitable elements will be clear to the skilled person.

These further elements may or may not be derived from plants, and may or may not be homologous to the plant that is to be transformed with the conduct of the invention (hereinbelow referred to as the “target plant”). For instance, the after elements may also have been derived from micro-organisms, viruses, etc., and may also be elements that are natively associated with the CGMMV sequence, such as the native CGMMV leader sequence (5'-UTR sequence).

The nucleotide sequences encoding these further elements may have been isolated and/or derived from a naturally occurring source—for instance as cDNA—and/or from known available sources (such as available plasmids, etc.), and/or may have been provided synthetically using known DNA synthesis techniques.

For instance, a construct of the invention will usually contain a suitable promoter operatively linked to the polynucleotide sequence encoding the defective replicase or the hairpin, e.g. such that it is capable of directing the expression of the polynucleotide sequence. Suitable promoters can be chosen from all known constitutive, inducible, tissue specific or other promoters that can direct expression of a desired nucleotide sequence in a plant and/or in part of a plant, including specific tissues and/or individual cells of the plant. In particular, promoters are used that are suitable for use in species of the Cucurbitaceae family, such as cucumber.

A specifically preferred promoter is the plastocyanine-promoter. Use of the 35S promoter is less preferred, as it may be less reliable in cucumber.

The terminator can be any terminator that is effective in plants. A particularly preferred terminator is the nos-3' terminator.

The selection marker can be any gene that can be used to select—under suitable conditions such as the use of a suitable selection medium—plants, plant material and plant cells that contain—e.g., as the result of a successful transformation—the genetic construct containing the marker. A particularly premed selection marker is the nptII-gene, which can be selected for using kanamycin.

The construct of the invention further preferably contains a leader sequence. Any suitable leader sequence, including those of viral origin, can be used. Preferably, a leader sequence essentially identical to the 5' untranslated (5'-UTR) region of the CGMMV genome is used. This may be derived from the viral RNA, or may be provided synthetically, e.g. as described in the Experimental Part.

Although not preferred, the invention also encompasses constructs that encode a fusion of a defective replicase as mentioned above, and at least one further amino acid sequence, such as a protein or polypeptide, or a part or fragment thereof, Preferably, expression of a defective replicase as (part of) such a fusion does not detract from the desired biological activity (i.e. protection against infection with CGMMV).

The construct of the invention can be provided in a manner known per se, which generally involves techniques such as restricting and linking nucleic acids/nucleic acid sequences, for which reference is made to the standard handbooks, such as Sambrook et al, “Molecular Cloning: A Laboratory Manual” (2nd ed.), Vols. 1-3, Cold Spring Harbor Laboratory (1989) of F. Ausubel et al, eds., “Current protocols in molecular biology”, Green Publishing and Wiley Interscience, New York (1987).

According to one embodiment, the genetic construct is preferably (also) in a form that can be maintained stable or inherited in a micro-organism, in particular a bacterium, more in particular a bacterium that can be used to transform a plant or plant material, such as *Agrobacterium*. In a further aspect, the invention also relates to such a micro-organism, in particular a bacterium, more in particular a bacterium that can be used to transform a plant, such as *Agrobacterium*, that contains a genetic construct according to the invention.

The genetic construct can be transformed into the target plant, plant cell or plant material by any suitable transformation technique known per se, including transformation with *Agrobacterium*, transformation with “denuded” DNA, for instance through particle bombardment or transformation of protoplast through electroporation or treatment with PEG.

Examples of suitable vectors systems for use with *Agrobacterium* are for instance binary vectors such as pBI121 and derivatives thereof co-integration vectors such as pGV1500 and derivatives of pB322. Suitable systems for transformation with denuded DNA include *E. coli*-vectors with high copy number, such as pUC-vectors and pBluescript II (SK+) vectors.

Upon transformation, the construct may for instance be incorporated into the genomic DNA of the plant, or it may be maintained/inherited independently in the plant (cell).

In a further aspect, the invention therefore comprises a method in which a plant, plant cell or plant material is transformed with a genetic construct as described above.

This method may also comprise cultivating the transformed plant cell or plant material into a mature plant, and may also comprise sexually or asexually reproducing or multiplying the transformed plant (and/or the mature plant obtained from the transformed plant cell or plant material).

The invention therefore also relates to a plant, plant cell or plant material, that has been transformed with—or more generally contains—a genetic construct as described above. Preferably, such a plant, plant cell or such plant material is resistant against infection with CGMMV as described herein.

The invention furthermore relates to cultivation material such as seed, tubers, roots, stalks, seedlings etc. for such a plant, as well as descendants of such a plant, obtained through sexual or asexual reproduction techniques. Such cultivation material and/or descendants most preferably still contain or have inherited the genetic construct of the invention, and more preferably also are resistant against infection with CGMMV as described herein.

The invention will now be illustrate by means of the following non-limiting Experimental Part and by means of the Figures.

Figure 1:
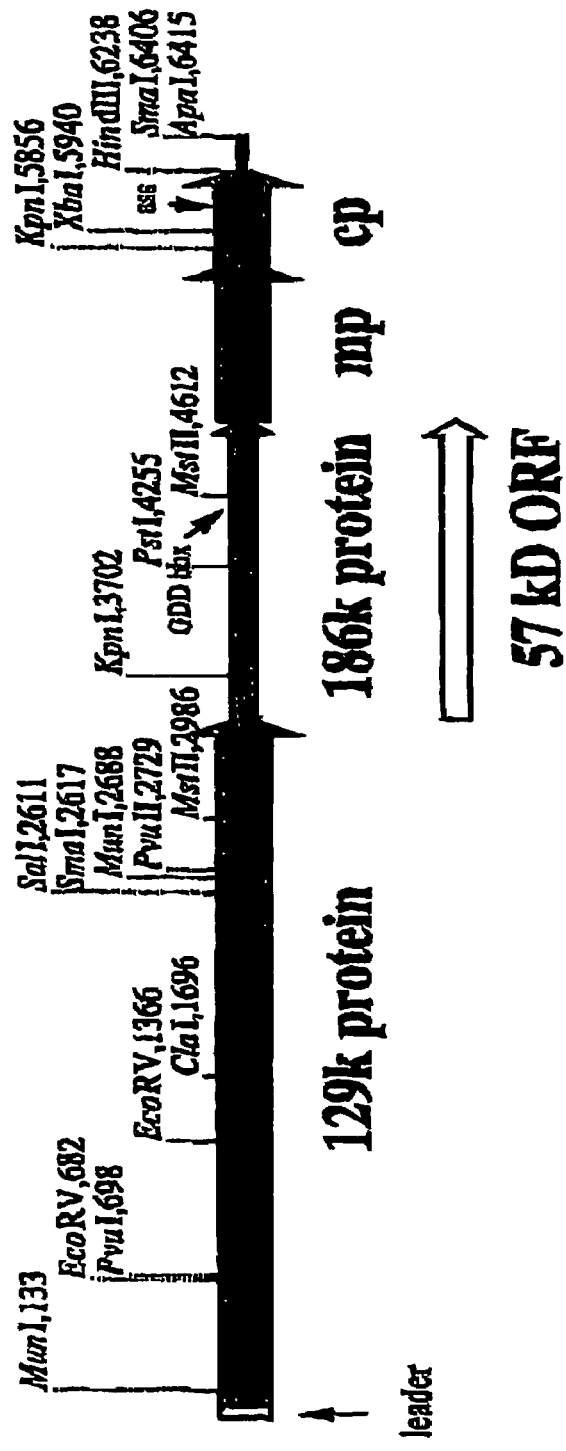
FIG. 1 is a schematic representation of the genome of CGMMV.
Figure 2:
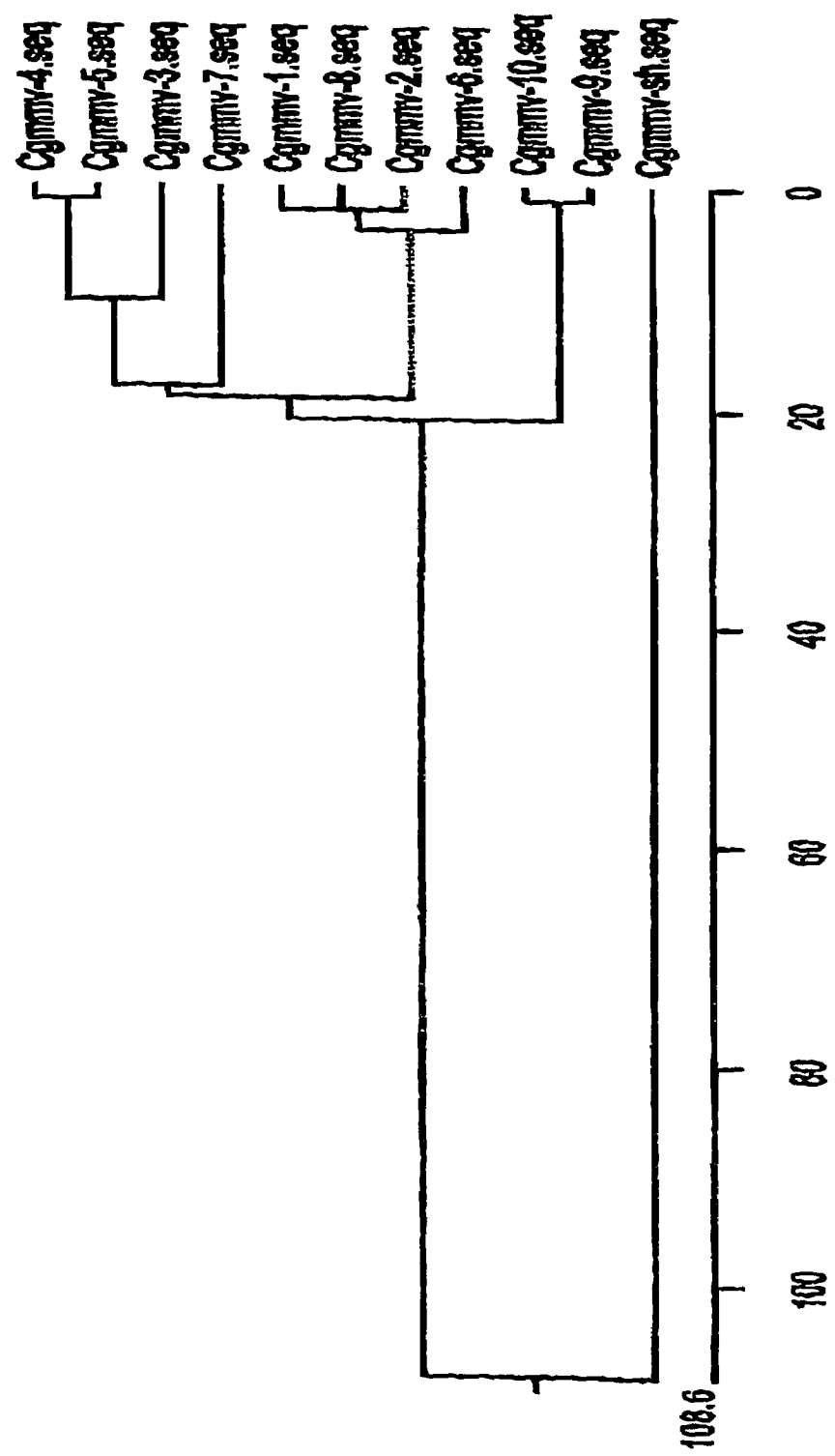
FIG. 2 gives a phylogenetic tree of CGMMV-coat protein (cp) for CGMMV-SH and the ten European isolates, using the method of J. Hein with weighed residue table.
Figure 3:
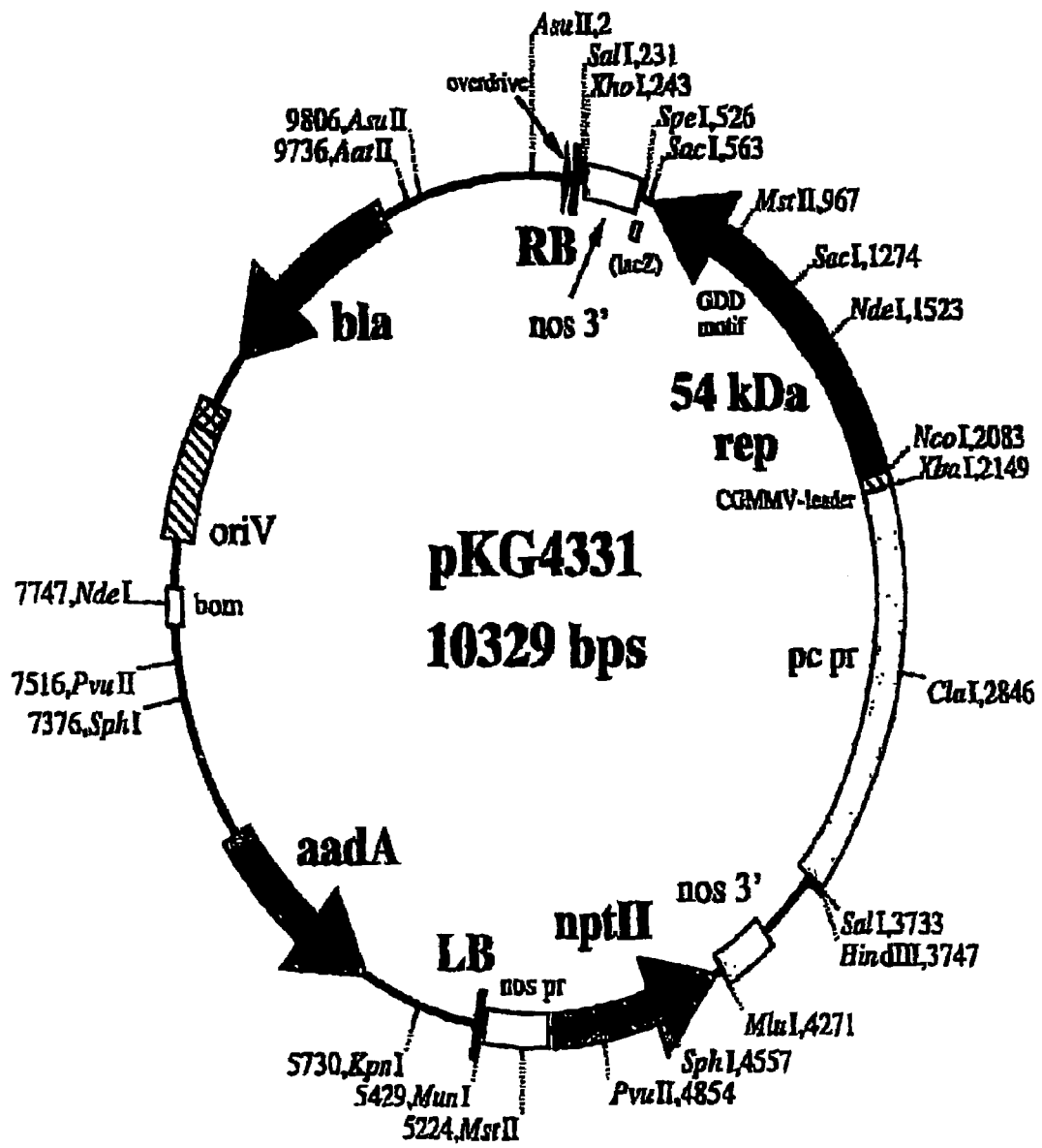
FIG. 3 shows the genetic construct pKG433 1.
Figure 4:
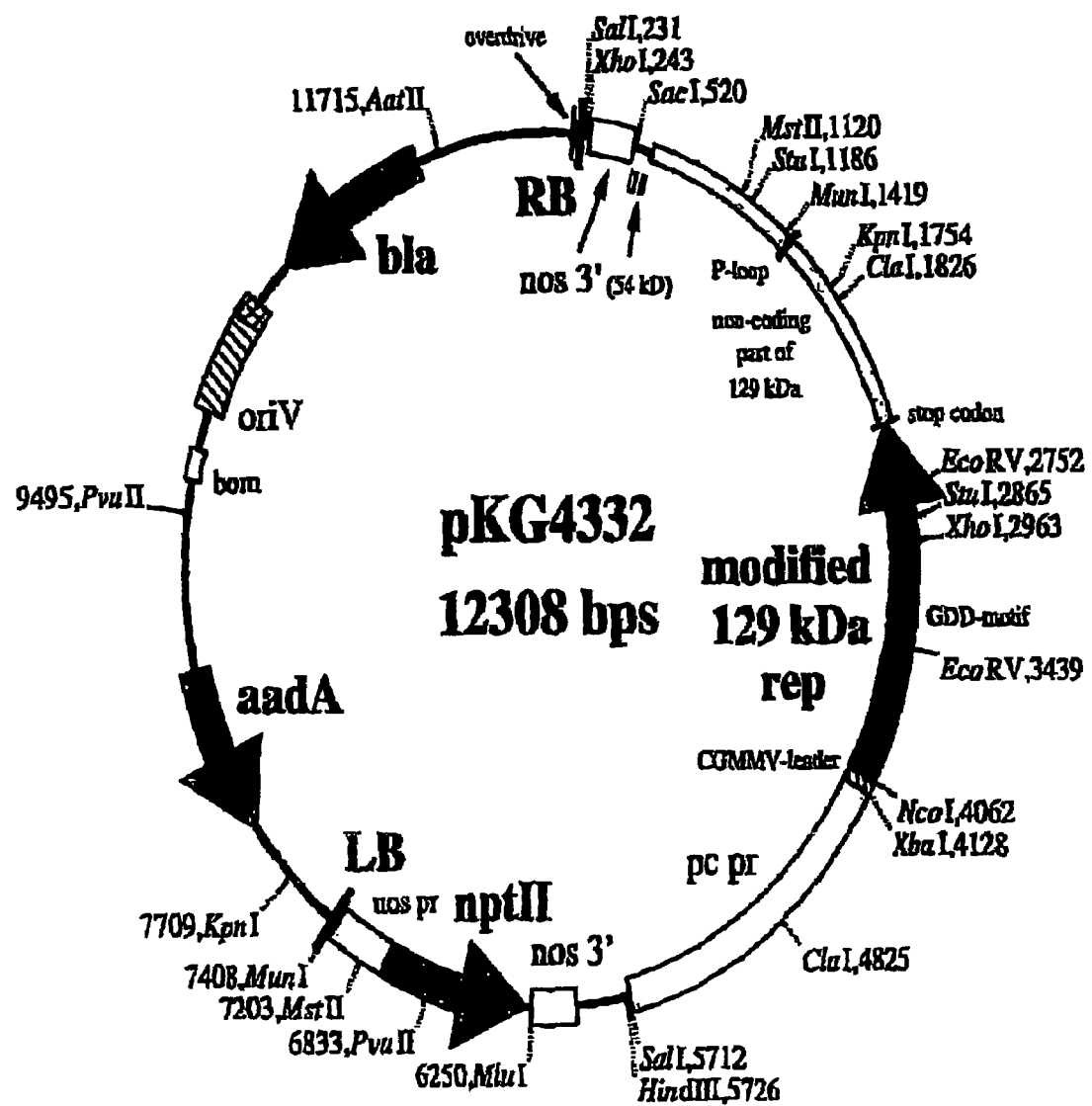
FIG. 4 shows the genetic construct pKG4332.
Figure 5:
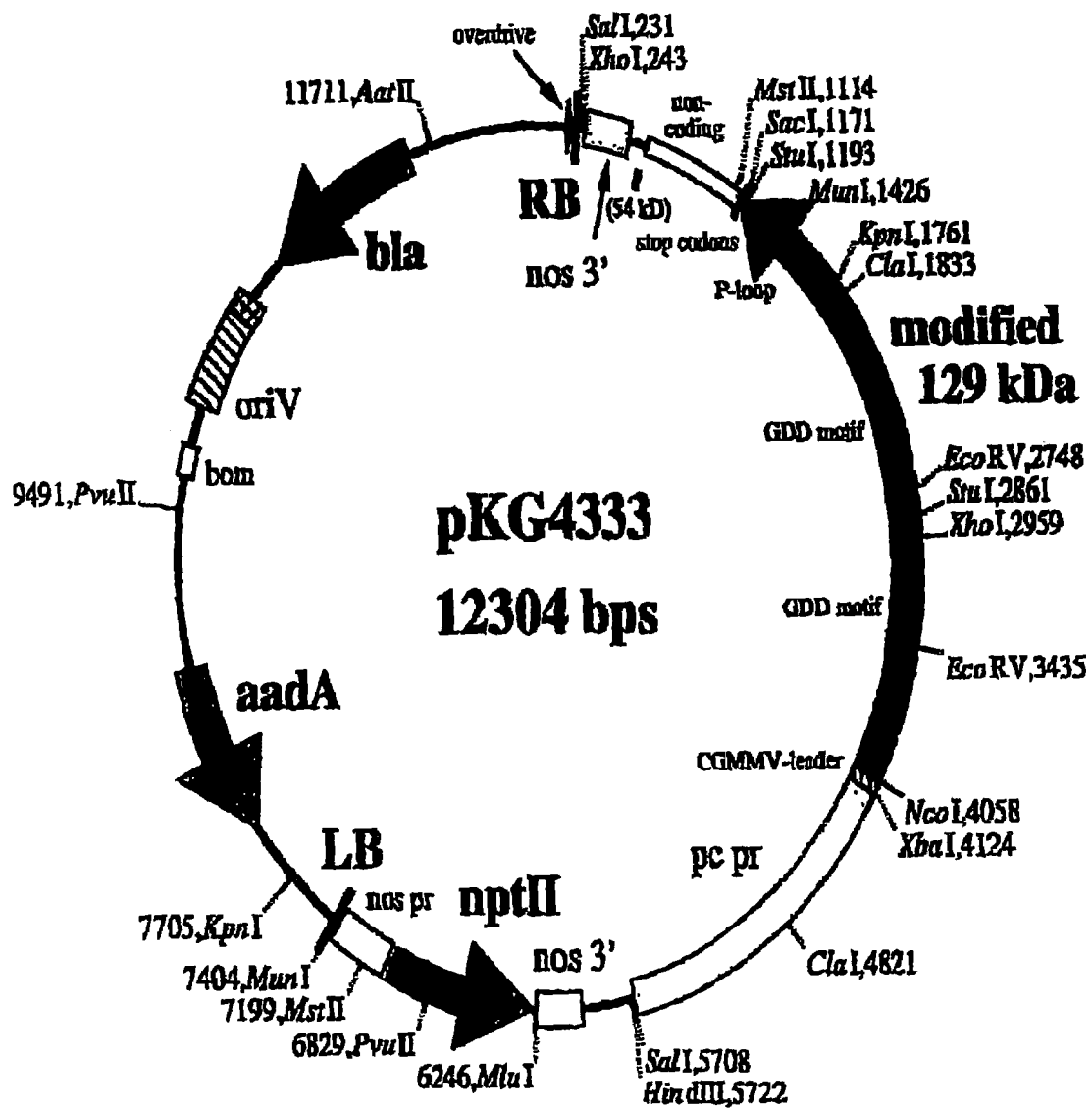
FIG. 5 shows the genetic construct pKG43 3 3.
Figure 6:
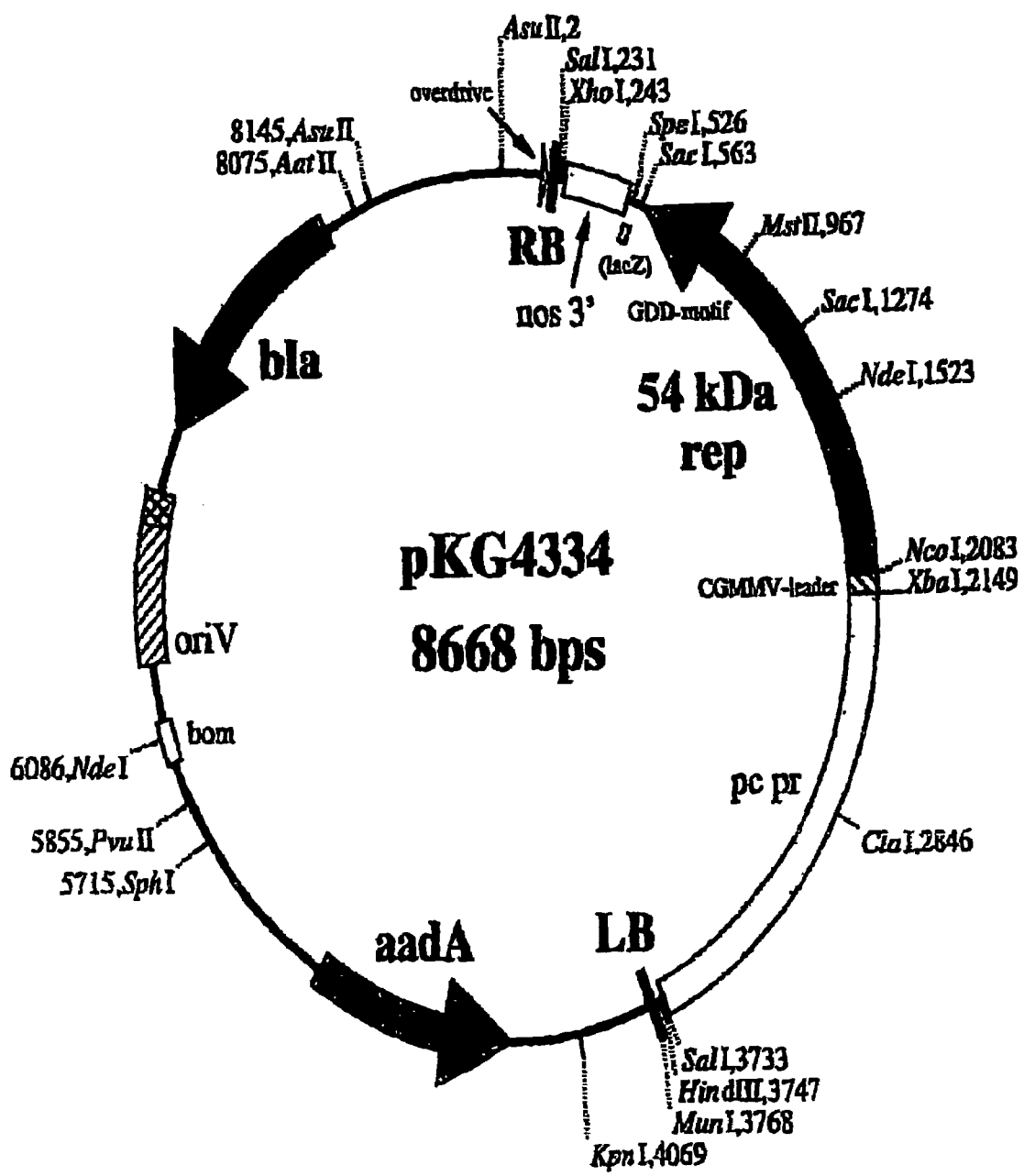
FIG. 6 shows the genetic construct pKG4334.
Figure 7:
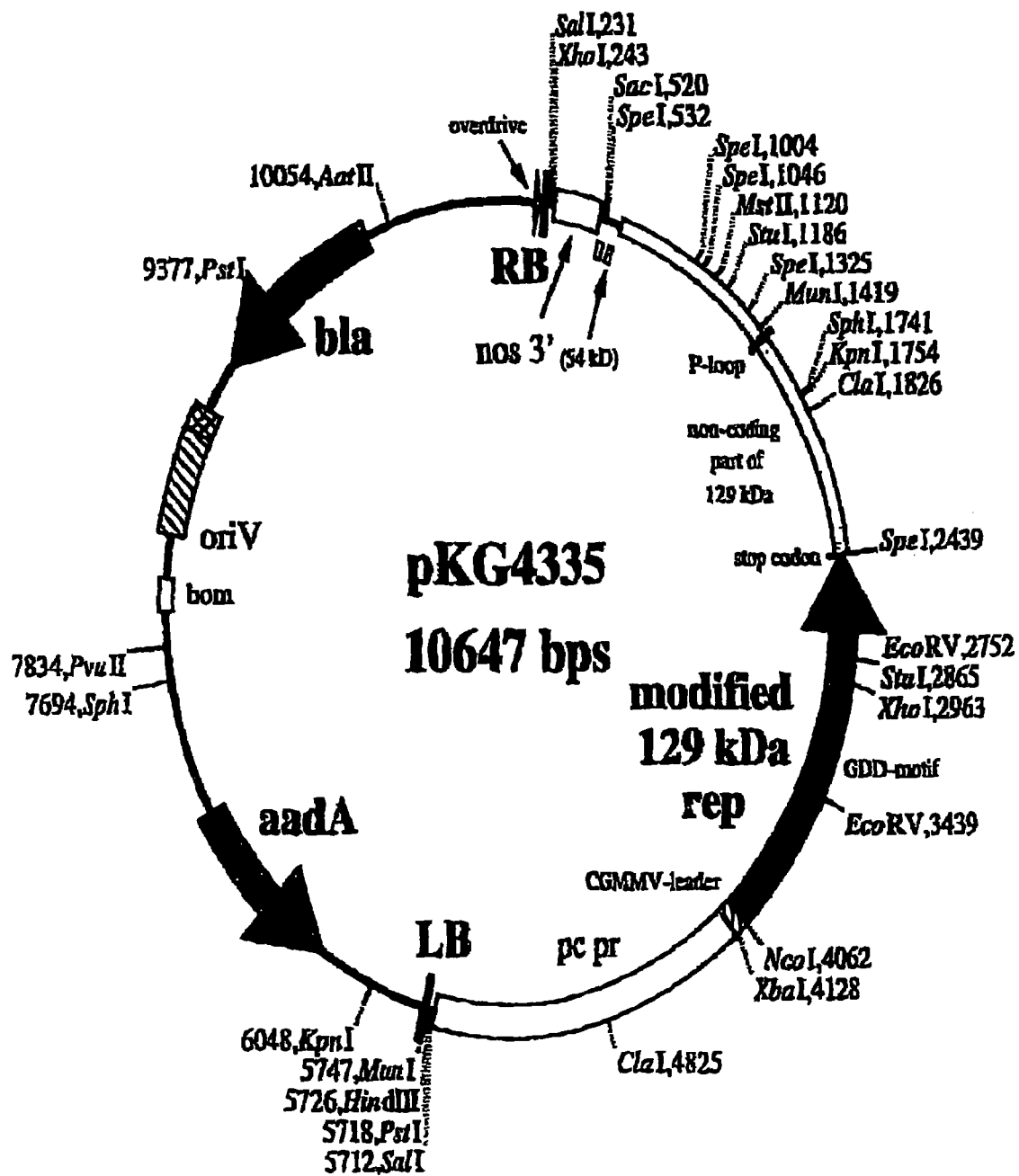
FIG. 7 shows the genetic construct pKG4335.
Figure 8:
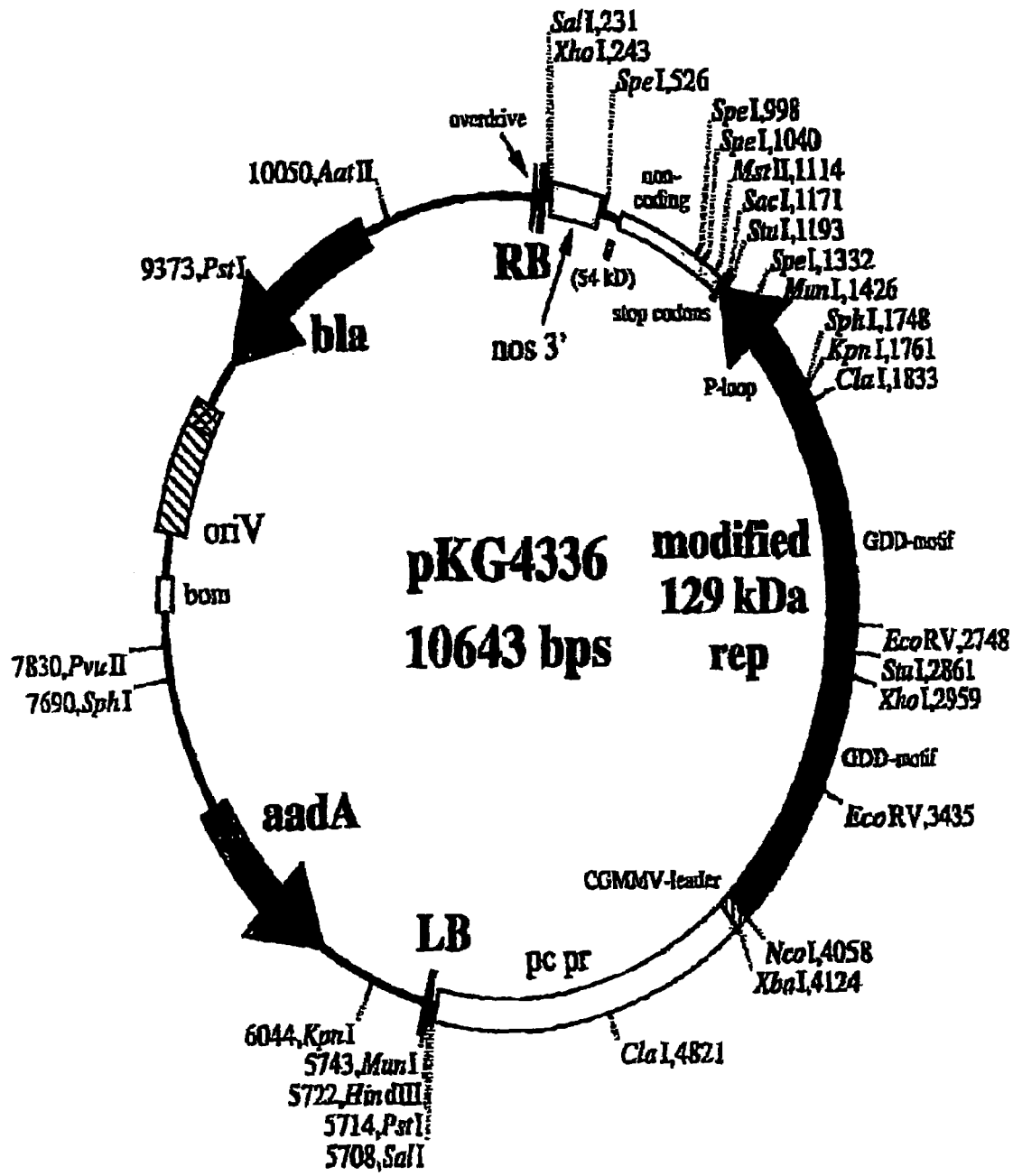
FIG. 8 shows the genetic construct pKG4336.

Also, in the Experimental Part hereinbelow, enzymes, kits, etc. were usually used according to the instructions of the manufacturer and/or using well-established protocols, unless indicated otherwise.

Experimental Part

EXAMPLE I

Cloning of the Coat Protein Genes of 10 CGMMV-Isolates

1. Collecting CGMMV Isolate

To make use of coat protein-mediated protection (CPMP) strategy against CGMMV, it is necessary to clone the coat protein cistrons of the isolates, that are economically important As the only sequence information available for CGMMV is derived from watermelon strains from the Far East, it was first decided to collect CGMMV isolates of important cucumber culture areas in Europe and the Mediterranean area. Table 1 lists the isolates collected from various geographical areas. All isolates were propagated on cucumber, and infected leaf material was stored at −80° C. The symptoms obtained after infection of cucumber cv. Hokus are listed in Table 1.

2. Design of PCR Primers

The possibility of sequence divergence among the various collected isolates, and between the isolates and the published sequences of CGMMV-SH and CGMMV-W exists. In order to identify nucleotide regions with a high degree of sequence conservation, that could serve as a basis of PCR primer design, an alignment study was carried out on corresponding sequences of CGMMV-SH, CGMMV-W and of some other related members of the tobamovirus group: Sunn-Hemp Mosaic Virus (SHMV, a variant of TMV) and Pepper Mild Mottle Virus (PMMV). For this purposes a region of 800 nucleotides just 5' of the coat protein cistron and a region of 170 nucleotides forming the far 3' of the viral genome were compared. In this sequence alignment, region with sufficient sequence homology among all compared viruses were identified. Based on these sequences, sets of PCR primers were designed, which are listed in Table 2.

TABLE 2

Design of primers for the RT-PCR amplification of coat protein sequences of CGMMV-isolates.

| Primers | Sequence | position on CGMMV-SH sequence |
|---|---|---|
| 5' primers | | |
| 97G01 | AGGTGTCAGTGGAGAACTCATTGA SEQ ID NO:24 | 5004 |
| 97G02 | GGCGTTGTGGTTTGTGG SEQ ID NO:25 | 5210 |
| 97G03 | CTGTAGGGGTGGTGCTACTGT SEQ ID NO:26 | 5248 |
| 3' primer | | |
| 97G18 | GCCCATAGAAACTTCAACGTC SEQ ID NO:27 | 6370 |

3. Amplification of the Coat Protein Regions

From leaf meal of cucumber plants infected with each of the 11 isolate described in Table 1, a total RNA extraction was prepared. Using each of the 5' primers listed in Table 2 in combination with 3' primer 97G18, reverse transcription of RNA and PCR amplification of cDNA with an annealing temperature of 55° C. was established using a kit manufactured by Perkin Elmer Cetus. Especially in the reactions with the 5' primer 97G03 amplification products of the correct size were obtained for each of the 11 RNA samples The PCR amplification products were directly cloned in T/A cloning vector pCR2.1 and introduced in *E. coli* stain INVαF'. For each of the RNA samples, the correct size of the cloned product (1.12 kb) was verified, and the clones were stored at −80° C. The amplification products of CGMMV-isolates 1 to 10 cloned in pCR2.1 were designated pKG4301 to pKG4301, and the one of CGMMV-SH cloned in pCR2.1 was designated pKG4311.

4. Nucleotide Sequence Analysis of the Coat Protein Cistrons

The sequences of the complete inserts of the plasmids pKG4301 to pKG4310 were determined by reading in both directions using m13 forward en m13 reverse sequencing primers. The sequence of the insert of pKG4311 was already known, as this plasmid contains a cDNA fragment of CGMMV-SH.

Sequence analysis confirmed, that in each case indeed the correct cDNA fragment of CGMMV had been obtained and cloned. With one exception, each amplified and cloned cDNA fragment consisted of 1123 base pairs, containing the CGMMV coat protein in and a large part of the CGMMV movement protein cistron.

The cloned sequences of all collected European isolates (isolates 1 to 10) are approximately 97% homologous among each other, but differ on average by 10% from the published sequence of CGMMV-SH. Comparison of each individual sequence revealed, that isolates 1 and 2, both from Eastern Europe are extremely alike. The same very high degree of identity was found between both isolates from cucumber greenhouses in the Netherlands (isolates 4 and 5) and between both isolates obtained from the Almeria area in Spain (isolates 9 and 10). None of the cDNA sequences was 100% identical to any of the other ones, but the differences in sequence are no more than a few nucleotides, and sometimes only one nucleotide in the coding region of the coat protein cistron. The Japanese isolate CGMMV-SH is clearly different from any of the European isolates.

5. Coat Protein Amino Acid Sequence Analysis

Based on the nucleotide sequences of the Open Reading Frames (ORF) of the coat protein cistrons of the 10 isolates, the to acid sequence could be deduced. In each of the analyzed sequences, the ORF consisted of a region of 486 nucleotides, coding for a protein of 161 amino acid residues. The predicted molecular mass of this proton is 17.3 kD, corresponding to earlier published results. The homology among the predicted protein sequences of the various isolates is as high as 98.1%. The only deviations are found for amino acid residue 19 (usually valine), residue 65 (mostly serine) and residue 84 (mostly leucine).

The sequence of the coat protein of the Japanese isolate CGMMV-SH only differs by 1 amino acid (residue 65) from the consensus sequence.

EXAMPLE II

Cloning of the Replicase Gene of CGMMV

1. Strategy for Replicase-Mediated Protection

By way of example, two approaches to replicase-mediated protection (RMP) against virus infections in plants were investigated.

One approach makes use of defective replicase genes in the form of truncated Open Reading Frames (ORF), in which the sequence downstream from the GDD motif had been truncated or altered through mutation.

The other approach makes use of the expression of the 'read-through' part of the replicase gene, i,e. the 57 kD sequence. It is thought that this ORF is not translated in the plant cell, but forms part of a larger 'read-through' ORF combining the coding regions of both the 129 kD replicase gene and the putative 57 kD protein gene, resulting a protein of 189 kD. However, expressing merely the 57 kD protein ORF in plant cells may result in a extremely strong resistance to infection by both virus particles and viral RNA which also would be capable of resisting high temperatures, as well as high inoculum concentrations.

For either of these approaches, either the full-length CGMMV replicase gene must be cloned, or both constituting parts must be cloned separately.

2. Design of Primers

Because of the high sequence homology of the coat protein genes of 11 CGMMV isolates it was assumed, that the sequences of the replicase genes of the various isolates would be also highly conserved. Based on the complete sequence of the CGMMV-SH isolate, primers were designed for the PCR amplification of the 57 kD ORF and of the 129 kD ORF (Tables 3 and 4). The primers were designed such, that they contain restriction sites for the future cloning of the amplification products. The 5' primers contain an NcoI-site positioned such, that it will coincide with the ATG start codon of the amplified ORF. The 3' primers contain a SacI-site downstream from the stop codon.

TABLE 3

Design of primers for the LR-RT-PCR amplification of the 57 kD replicase sequence of CGMMV.

| Primers | sequence | position on CGMMV-SH sequence |
|---|---|---|
| 5' primer | | |
| 98A88 | CCATGGAGAATTCGCTGTATGTCC SEQ ID NO:28 | 3497 |
| 3' primer | | |
| 98A86 | CGAGCTCTCGACTGACACCTTAC SEQ ID NO:29 | 5001 |

TABLE 4

Design of primers for the LR-RT-PCR amplification of the 129 kD replicase gene sequence of CGMMV.

| Primers | sequence | position on CGMMV-SH sequence |
|---|---|---|
| 5' primers | | |
| 98A84 | CCATGGCAAACATTAATGAAC SEQ ID NO:30 | 59 |
| 98A85 | CAACCATGGCAAACATTAATG SEQ ID NO:31 | 56 |
| 3' primer | | |
| 98G63 | TAACAGGGAGGAAAATATTACG SEQ ID NO:32 | |

3. Long-Range Reverse Transcriptase Polymerase Chain Reactions

From the known sequence of CGMMV-SH it was derived that the size of the 57 kD protein gene is 1.5 kb. Such a size is at the limit of the size image that can be amplified in a PCR with standard Taq polymerase. For the amplification of this cDNA fragment, and certainly for the amplification of the cDNA fragment for the 129 kD replicase gene, a different polymerase suitable for long range amplifications must be used. In these experiments, rTth DNA polymerase was used.

For direct amplification of cDNA fragments from total RNA extractions a RT-PCR kit is normally employed, combining in one reaction the activity of the Reverse Transcriptase (RT), producing a single cDNA strand complementary to the RNA template strand beginning at one primer annealed to the 3' end of the RNA molecules, and the activity of the Polymerase, amplifying the thus produced single stranded cDNA molecule in a normal PCR fashion.

Because of the need to use long range polymerase, it was attempted to combine the RT with the long range polymerase to produce in one reaction large-size amplification products directly from total RNA extracts. This type of reaction was called a Long Range Reverse Transcriptase Polymerase Chain Reaction (LR-RT-PCR).

4. LR-RT-PCR Amplification and Cloning of the 57 kD Protein Gene

Using the primers listed in Table 3 and the LR-RT-PCR described above, a specific 1.5 kb amplification product was obtained from total RNA extracts of cucumber leaves infected with CGMMV-4. This isolate was chosen, as it originated from the Dutch cucumber greenhouse cultures, and would thus represent an economically important isolate. Because long range polymerases contain a 'proof reading' activity and do not leave A-additions on the amplification products, as does the Taq polymerase normally employed in PCR, direct cloning of the amplification products in a TA vector accommodating the A-additions was not possible. Therefore, the amplification products were briefly treated with Taq polymerase, resulting in the addition of A-overhangs on the amplified DNA molecules. These molecules could then sly be cloned in the TA vector pCR2.1, and transformed to E. coli MC1061. Clones with the correct insert size of 1.5 kb were stored at −80° C. and are known as pKG4321.

5. Sequence Analysis of the 57 kD Protein Gene

The nucleotide sequence of the cloned insert of pKG4321 was determined by double-stranded sequencing using m13 forward en m13 reverse primers and subsequent primer walking steps. The ORF coding for a putative 57 kD protein gene (SEQ ID no 3) showed 90% homology at the nucleotide level to the corresponding sequence of the Japanese isolate CGMMV-SH (SEQ ID no 19). The predicted amino acid sequence (SEQ ED no 4) shows a 98.2% homology to the one predicted by the CGMMV-SH sequence (SEQ ID no 20).

The GDD motif characteristic for viral replicase genes resides at amino acid residues 364-366.

6. LR-RT-PCR Amplification and Cloning of the 129 kD Replicase Gene

Using the primers listed in Table 4 in a Long Rage Reverse Transcriptase Polymerase Chain Reaction as described under 3, one specific amplification product of 3.5 kb representing the viral 129 kD replicase gene was obtained from total RNA of cucumber leaves infected with CGMMV isolate 4 (Table 1). Because long range polymerases contain a 'proof reading' activity and do not leave A-additions on the amplification products, as does the Taq polymerase normally employed in PCR, direct cloning of the amplification products in a TA vector accommodating the A-additions was not possible. Therefore, the amplification products were briefly treated with Taq polymerase, resulting in the addition of A-overhangs on the amplified DNA molecules. These molecules could easily be cloned in the TA vector pCR2.1, and transformed to E. coli MC1061. Clones with the correct insert size of 3.5 kb were stored at −80° C. and are known as pKG4322.

7. Sequence Analysis of the 129 kD Protein Gene

The nucleotide sequence of the amplification product cloned in pKG4322 was determined by double-sided sequencing using m13 forward en m13 reverse primers, and a primer walking strategy. The ORF coding for the 129 kD replicase gene (SEQ ID no 1) showed 88% homology at the nucleotide level to the corresponding sequence of the Japanese isolate CGMMV-SH (SEQ ID no 17). The ORF of the Dutch cucumber greenhouse isolate codes for a replicase protein of 1144 amino acids, which is one amino acid in extra in comparison to the CGMMV-SH strain. The predicted amino acid sequence (SEQ ID no. 2) shows a 97.1% homology to the one predicted by the CGMMV-SH sequence (SEQ ID no 18).

Two GDD motifs are found at amino acid residues 256258 and 540-542.

8. Site-Directed Mutagenesis of the 129 kD ORF

As explained above, one approach to obtain RMP in plant cells was to make use of replicase genes truncated either in the GDD motif, or truncated in the P-loop of the helicase domain. In order to create gene compression cassettes carrying such truncated genes, a site-directed mutagenesis approach was followed to introduce stop codons at the required positions in the ORF. To this end, several parts of the 129 kD replicase ORF were re-amplified from pKG4322 as a template using specifically designed primers that included unique restriction sites for future re-assembling of the thus amplified products, as well as the required mutations in the form of stop codons (Table 5). These stop codons should ensure the proper truncation of the translation of the protein. Several stop codons were designed one after the other in the three reading frames in these primers, thus ensuring an effective translation-deficient mutation.

TABLE 5

Design of primers for the site-directed mutagenesis of the 129 kD replicase gene of CGMMV.

| Primers | sequence |
|---------|----------|
| 98L99   | GAGCTCGGATCCACTAGTAACGGC<br>SEQ ID NO:33 |
| 98L107  | TAGAGCTCTTGAAGCTAAGCAAATTCCG<br>SEQ ID NO:34 |
| 98L108  | TTCAAGAGCTCTAATCACCGAAGACAAAGGC<br>SEQ ID NO:35 |
| 98L102  | GAATTATATCGATTATCTATCGGC<br>SEQ ID NO:36 |
| 98L103  | GATAATCGATATAATTCTTCATCTGCC<br>SEQ ID NO:37 |
| 98L104  | AACTAGTAATTGATGATCTGTTCAAGAAG<br>SEQ ID NO:38 |
| 98L105  | AATTACTAGTTTCCGGAAGCAAGCAGCTCAG<br>SEQ ID NO:39 |
| 98L106  | GCCCTCTAGATGCATGCTCGAG<br>SEQ ID NO:40 |

Using primers 98L103 and 98L104, a fragment from the downstream half of the 129 kD gene from the GDD motif up to the ClaI-site was amplified, while simultaneously stop codons were introduced at the site of the GDD motif. This fragment cloned in TA vector pCR2.1 was called pKG4325.

Using primers 98L105 and 98L106, a fragment corresponding to the 5' half of the 129 kD gene up to the GDD motif was amplified, while simultaneously a stop codon was introduced at the site of the GDD motif. This fragment cloned in T/A vector pCR2.1 was called pKG4326.

Replacing an XbaI-ClaI fragment of pKG4322 with the combined amplified products of pKG4325 and pKG4326 reconstitutes the full-length 129 kD replicase ORF of pKG4322 with stop codons introduced at the site of the GDD motif. This construct is named pKG 4329.

Using primers 98L99 and 98L107, a fragment at the far downstream end of the 129 kD gene from the P-loop to the end of the ORF was amplified, while simultaneously stop codons were introduced at the site of the P-loop. This fragment cloned in T/A vector pCR2.1 was called pKG4327.

Using priers 98L108 and 98L102, a fragment corresponding to a central part of the 129 kD gene from the GDD motif up to the P-loop was amplified, while simultaneously a stop codon was introduced at the site of the P-loop. This fragment cloned in T/A vector pCR2.1 was called pKG4328.

Replacing an BamHI-ClaI fragment of pKG4322 with the combined amplified products of pKG4327 and pKG4328 reconstitutes the full-length 129 kD replicase ORF of pKG4322 with stop codons introduced at the site of the P-loop. This construct is named pKG4330.

EXAMPLE III

Transformation of Cucumber

1. Construction of a CGMMV-Leader Sequence

For optimal expression and stability of the replicase gene transcripts in plant cells, it was thought necessary to add a sequence identical to the 5' untranslated (5' UTR) region of the CGMMV genome upstream from the ORF sequence in the plant expression cassette. Because the 5' UTR of viral genomes contain highly repetitive RNA, this sequence could not be obtained by RT-PCR amplification, as no specific primers could be designed. Instead, a synthetic region identical to the 5' UTR of CGMMV-SH was assembled from the four oligonucleotide sequences:

```
97G40    (CTAGAGTTTTAATTTTTATAATTAAACAAA),
         SEQ ID NO:41,

97G41    (TCAAAATTAAAAATATTAATTTGTTTGTTGTTGTTG),
         SEQ ID NO:42,

97G42    (CAACAACAACAACAACAAACAATTTTAAAACAACAC)
         SEQ ID NO:43 and

97G43    (TTGTTGTTTGTTAAAATTTTGTTGTGGTAC)
         SEQ ID NO:44.
```

These oligonucleotides were designed such, that outside the sequence corresponding to the 5' UTR they contain restriction sites for XbaI and NcoI, thus facilitating further cloning. Adding the four oligonucleotides together will cause spontaneous assembling due to the design of extensive regions of overhang. Using these restriction sites, the assembled mixture was cloned in a plant expression vector containing an *Arabidopsis thaliana* plastocyanine promoter (Vorst et al, 1993) and a *Agrobacterium tumefaciens* nopaline synthase terminator sequence (Depicker et al., 1982) in a pUC19-derived plasmid. This expression cassette was called pKG1315. The complete expression cassette consisting of the plastocyanine promoter, the CGMMV leader sequence and the nos terminator was subsequently removed from pKG1315 using HindIII and EcoRI as restriction enzymes, and recloned in the corresponding restriction sites of:

1) an intermediate type *Agrobacterium* transformation vector for cointegrate type vector systems containing an nptII selectable marker gene cassette to create pKG1575, and
2) an intermediate type *Agrobacterium* transformation vector for cointegrate type vector systems containing no selectable marker gene to create pKG1110.

2. Construction of Transformation Vectors

The three cloned and modified replicase constructs of pKG4321, pKG4329 and pKG4330 were isolated from the plasmids by restriction with BamHI (filled in with Klenow) and NcoI and ligated into the SacI (filled in with Klenow) and NcoI sites of each of the two transformation vectors pKG1575 and pKG1110, resulting in a total of six transformation vectors, listed in Table 6.

TABLE 6

List of six transformation vectors for the expression in plants of parts of the CGMMV-replicase gene.

| Vector | vector type | modified CGMMV-replicase gene |
|---|---|---|
| PKG4331 | Intermediate type with nptII | 57 kD ORF |
| PKG4332 | intermediate type with nptII | 129 kD ORF with stopcodon in GDD motif |
| PKG4333 | intermedinte type with nptII | 129 kD ORF with stopcodon in P-loop |
| PKG4334 | intermediate type | 57 kD ORF |
| PKG4335 | intermediate type | 129 kD ORF with stopcodon in GDD motif |
| PKG4336 | intermediate type | 129 kD ORF with stopcodon in P-loop |

3. Transformation of Cucumber

The intermediate type transformation vectors pKG4331 and pKG4333 were introduced into *Agrobacterium tumefaciens* strain GV2260 by tri-parental mating. Transconjugants which had incorporated the intermediate type vector into their Ti-plasmids through homologous recombination were selected on the basis of streptomycin and spectinomycin resistance and analyzed for the correct insertion of the vector.

Cucumber plants were transformed with these two strains of *Agrobacterium,* as well as wit an *Agrobacterium* strain harbouring only the nptII selection marker, using published procedures. A number of transgenic cucumber plant were obtained. The plants were transferred to a greenhouse to flower and set seed, The seedlings germinating from these R1 seed were mechanically infected with CGMMV isolate 1-3 weeks post-inoculation, the plants were scored for symptoms of virus infection, as described in the assay for tolerance to virus infection set out in under 4, below.

4. Assay for Tolerance to Virus Infection

The seedlings of transgenic cucumber germinating from these R1 seed were mechanically infected with CGMMV isolate 1. Fresh inoculum was prepared from a crude leaf extract of susceptible non-transgenic cucumber plants cv. Hokus pre-infected with this same isolate 3 weeks previously. Seedlings of non-transformed cucumber plants were used as controls in the assay. During 21 days post-inoculation the appearance of viral symptoms was scored visually every 2 days. In this assay, individual plants are scored as being tolerant when they remain free of visible symptoms for at least 7 days, and preferably more than 14 days, and more preferably more than 21 days post-inoculation.

Sixty-four independent transgenic lines were assayed, with 14 to 20 seedlings for each line. Control seedlings all became diseased within 9 days post-inoculation. A number of seedlings in seventeen of the transgenic lines showed clear absence of symptoms for a prolonged period of time, and remained free of symptoms after 21 days post-inoculation. Of some transgenic lines, the number of symptom-fee plants corresponded to Mendelian segregation of a transgene present in a single locus. In one particular transgenic cucumber line 4 out of 14 seedlings remained symptom-free during the assay period, which may indicate that the tolerant phenotype corresponds to the homozygous state of a transgene present in one single locus, although, as mentioned above, the invention is not limited to a specific mechanism.

EXAMPLE IV

1. Construction of Hairpin RNA Construct
1.1. Genome Organization of CGMMV

The genome of CGMMV consists of a single-stranded RNA molecule coding for a 129 kD protein with replicase function (RNA dependent RNA polymerase), a putative 54 kD protein, a 29 kD movement protein and a 17.3 kD coat protein The presence of the 54 kD protein has not been detected in infected plants. However, a 186 kD protein has been found instead, being the product of a read-through translation of the 129 kD and the 54 kD Open Reading Frames. The 186 kD protein is also thought to play a role in virus replication. The genome structure of CGMMV is thus very similar to those of other members of the tobamovirus group.

The complete sequence of only one isolate of CGMMV has been determined (Ugaki et al., 1991; Genbank accession numbers D12505 and D01188). This isolate "SH" had been found infected watermelon plants in East Asia. Furthermore, the sequence of the coat protein gene of one other isolate ("W") obtained from infected watermelon is known (Meshi et al., 1983; Genbank accession numbers V01551 and J02054), as well as the sequence of the 29 kD movement protein gene of a watermelon strain (Saito et al, 1988; Genbank accession number J04332). The nucleotide sequence of the CGMMV-SH isolate shows 55 to 56% identity with tobacco mosaic virus (TMV) and tobacco mild green mosaic virus (TMGMV), both other members of the tobamovirus group (Ugaki et al., 1991).

1.2. Cloning of the RdRp Gene of CGMMV

In the present example of the invention, the sequence elected for constructing the constructs is the RNA dependent RNA polymerase of CGMMV.

a. Primer Design

Because of the high sequence homology of the coat protein genes of 11 CGMMV isolates it was assumed, that the sequences of the replicase genes of the various isolates would be also highly conserved. Based on the complete sequence of the CGMMV-SH isolate, primers were designed for the PCR amplification of the 54 kD ORF and of the 129 kD ORF (Tables 7 and 8). The primers were designed such, that they contain restriction sites for the future cloning of the amplification products. The 5' primers contain an NcoI-site positioned such, that it will coincide with the ATG start codon of the amplified ORF. The 3' primers contain a SacI-site downstream from the stop codon.

TABLE 7

Design of primers for the LR-RT-PCR amplification of the 54 kD replicase sequence of CGMMV.

| primers | sequence | position on CGMMV-SH sequence |
|---|---|---|
| 5' primer | | |
| 98A88 | CCATGGAGAATTCGCTGTATGTCC SEQ ID NO:28 | 3497 |
| 3' primer | | |
| 98A86 | CGAGCTCTCGACTGACACCTTAC SEQ ID NO:29 | 5001 |

TABLE 8

Design of primers for the LR-RT-PCR amplification of the 129 kD replicase gene sequence of CGMMV.

| primers | sequence | position on CGMMV-SH sequence |
|---|---|---|
| 5' primers | | |
| 98A84 | CCATGGCAAACATTAATGAAC SEQ ID NO:30 | 59 |
| 98A85 | CAACCATGGCAAACATTAATG SEQ ID NO:31 | 56 |
| 3' primer | | |
| 98G63 | TAACAGGGAGGAAAATATTAC SEQ ID NO:32 | | b. Long-Range Reverse Transcriptase Polymerase Chain Reactions

From the known sequence of CGMMV-SH it was clear, that the size of the 54 kD protein gene is 1.5 kb. Such a size is at the limit of the size range that can be amplified in a PCR with standard Taq polymerase. For the amplification of this cDNA fragment, and certainly for the amplification of the cDNA fragment for the 129 kD replicase gene, a different polymerase suitable for long range amplifications must be used. In these experiments, a long-range polymerase was used.

For direct amplification of cDNA fragments from total RNA extractions a RT-PCR kit is normally employed, combining one reaction the activity of the Reverse Transcriptase (RT), producing a single cDNA strand complementary to the RNA template strand beginning at one primer annealed to the 3' end of the RNA molecules, and the activity of the Polymerase, amplifying the thus produced single stranded cDNA molecule in a normal PCR fashion.

Because of the need to use long range polymerase, it was attempted to combine the RT with the long range polymerase to produce in one reaction large-size amplification products directly from total RNA extracts. This type of reaction was called a Long Range Reverse Transcriptase Polymerase Chain Reaction LR-RT-PCR).

c. LR-RT-PCR Amplification and Cloning of the 54 kD Protein Gene Using the primers listed in Table 1 and the LR-RT-PCR described above, a specific 1.5 kb amplification product was obtained from total RNA extracts of cucumber leaves infected with CGMMV-4. This isolate was chosen, as it originated from the Dutch cucumber greenhouse cultures, and would thus represent an economically important isolate. Because long range polymerases contain a 'proof reading' activity and do not leave A-additions on the amplification products, as does the Taq polymerase normally employed in PCR, direct cloning of the amplification products in a T/A vector accommodating the A-additions was not possible. Therefore, the amplification products were briefly treated with Taq polymerase, resulting in the addition of A-overhangs on the amplified DNA molecules. These molecules could then easily be cloned in the T/A vector pCR2.1, and transformed to *E. coli* MC1061. Clones with the correct insert size of 1.5 kb were stored at −80° C. and are known as pKG4321.

d. Sequence Analysis of the 54 kD Protein Gene

The nucleotide sequence of the cloned insert of pKG4321 was determined by double-stranded sequencing using m13 forward en m13 reverse primers. The ORF coding for a putative 54 kD protein gene showed 90% homology at the nucleotide level to the corresponding sequence of the Japanese isolate CGMMV-SH. The predicted amino acid sequence shows a 98.2% homology to the one predicted by the CGMMV-SH sequence.

The GDD motif characteristic for viral replicase genes resides at amino acid residues 364-366.

e. LR-RT-PCR Amplification and Cloning of the 129 kD Replicase Gene

Using the primers listed in Table 9 in a Long Range Reverse Transcriptase Polymerase Chain Reaction as described in 6.2.3, one specific amplification product of 3.5 kb representing the viral 129 kD replicase gene was obtained from total RNA of cucumber leaves infected with CGMMV isolate 4 (Table 1). Because long range polymerases contain a 'proof reading' activity and do not leave A-additions on the amplification products, as does the Taq polymerase normally employed in PCR, direct cloning of the amplification products in a T/A vector accommodating the A-additions was not possible. Therefore, the amplification products were briefly treated with Taq polymerase, resulting in the addition of A-overhangs on the amplified DNA molecules. These molecules could easily be cloned in the T/A vector pCR2.1, and transformed to *E. coli* MC1061. Clones with the correct insert size of 3.5 kb were stored at −80° C. and are known as pKG4322.

TABLE 9

Design of primers for the PCR amplification of CGMMV target sequences and plant intron sequences, to be assembled in hairpin encoding gene constructs.

| Primer | target | restriction site added | sequence |
| --- | --- | --- | --- |
| primer 1 | 5' RdRp | SacI | CGAGCTCATCTCGTTAGTCAGC SEQ ID NO:45 |
| primer 2 | 3' RdRp | BamHI | GGGATCCACGTCTGGACAGG SEQ ID NO:46 |
| primer 3 | 5' RdRp | XbaI | CTCTAGAATCTCGTTAGTCAGC SEQ ID NO:47 |
| primer 4 | 3' RdRp | BamHI | AGGATCCTACACGAACCTATC SEQ ID NO:48 |
| primer 5 | 5' AO3 | BamHI | AGGATCCATTGCGGTAACACAAC SEQ ID NO:49 |
| primer 6 | 5' AO3 | BglII | TAGATCTATTGCGGTAACACAAC SEQ ID NO:50 |
| primer 7 | 3' AO3 | BglII | TAGATCTGTGTGATTCTGG SEQ ID NO:51 |
| primer 8 | 3' AO3 | BamHI | AGGATCCGTGTGATTCTGG SEQ ID NO:52 |
| primer 9 | 5' IV2 | BamHI | AGGATCCGTGTACGTAAGTTTC SEQ ID NO:53 |
| primer 10 | 5' IV2 | BglII | TAGATCTGTGTACGTAAGTTTC SEQ ID NO:54 |
| primer 11 | 3' IV2 | BglII | TAGATCTGTGATACCTGCAG SEQ ID NO:55 |
| primer 12 | 3' IV2 | BamHI | AGGATCCGTGATACCTGCAG SEQ ID NO:56 |
| primer 13 | 5' RdRp | SacI | CGAGCTCATCTCGTTAGTCAGCTAGC SEQ ID NO:57 |

TABLE 9-continued

Design of primers for the PCR amplification of CGMMV target sequences and plant intron sequences, to be assembled in hairpin encoding gene constructs.

| Primer | target | restriction site added | sequence |
|---|---|---|---|
| primer 14 | 3' RdRp | BamHI | AGGATCCTTTGTGCCTCTGTACATG SEQ ID NO:58 |
| primer 15 | 5' RdRp | XbaI | CTCTAGAATCTCGTTAGTCAGCTAGC SEQ ID NO:59 |
| primer 16 | 3' RdRp | BamHI | AGGATCCATCAACCCTAAATTGAGCC SEQ ID NO:60 |
| primer 17 | 5' RdRp | BamHI | AGGATCCAGCAGGGAAATAAGTACGC SEQ ID NO:61 |
| primer 18 | 3' RdRp | BamHI | AGGATCCGGTATGGACAAAATCAGC SEQ ID NO:62 |
| primer 19 | 5' AO3 | BamHI | AGGATCCATTGCGGTAACACAACCTCTC SEQ ID NO:63 |
| primer 20 | 3' AO3 | BglII | TAGATCTGTGTGATTCTGGAAAAG SEQ ID NO:64 |
| primer 21 | 3' IV2 | BglII | TAGATCTGTGATACCTGCACATCAAC SEQ ID NO:65 |
| primer 22 | 5' IV2 | BamHI | AGGATCCGTGTACGTAAGTTTCTGCTTC SEQ ID NO:66 |
| primer 23 | 5' RdRp | XbaI | CTCTAGAATCTCGTTAGTCAGCTAGC SEQ ID NO:67 |
| primer 24 | 3' RdRp | BamHI | AGGATCCAGCAGGGAAATAAGTACGC SEQ ID NO:68 | f. Sequence Analysis of the 129 kD Protein Gene

The nucleotide sequence of the amplification product cloned in pKG4322 was determined by double-stranded sequencing using m13 forward en m13 reverse primers, and a primer walking strategy. The ORF coding for the 129 kD replicase gene showed 88% homology at the nucleotide level to the corresponding sequence of the Japanese isolate CGMMV-SH. The ORF of the Dutch cucumber greenhouse isolate codes for a replicase protein of 1144 amino acids, which is one amino acid in extra in comparison to the CGMMV-SH strain The predicted amino acid sequence shows a 97.1% homology to the one predicted by the CGMMV-SH sequence.

1.3. Cloning of Target Sequences

In one particular example of the invention, a fragment of 489 nt of the 5' end of RdRP gene of CGMMV was chosen as a target sequence for the construction of sense and antisense sequences separated by a stuufer fragment. These fragments were isolated from the cloned 129 kD ORF of pKG4322 (described above) by PCR amplification PCR primers were designed a corresponded to the 5' and 3' parts of the chosen target sequence, and included in the 5' part of the primer sequences, an additional restriction site to facilitate the cloning of the amplification products.

One primer set (primer 1 and primer 2, Table 9) was designed to amplified the chosen target fragment of 489 bp from pKG4322, whereby restriction sites for SacI (primer 1) and BamHI (primer 2) were introduced by the PCR process at either end of the fragment.

A second primer set (prier 3 and primer 4, Table 9) was designed to amplify from pKG4322 the same target sequence of 489 bp from pKG4322 plus an additional sequence of 332 bp downstream of the target sequence in the CGMMV RdRP gene. Primer 4 and primer 5 added restriction sites for XbaI and BamHI, respectively, at either end of the amplified fragment. Details of the priers are given in Table 9. The PCR products obtained by amplification of the target sequences using the respective primers were cloned in T/A cloning vector pCR2.1, resulting in pCG1 (489 bp target sequence) and pCG2 (821 bp fragment). The ligation product was transformed to *E. coli* MC1061 and stored at −80° C. The sequences of the cloned PCR products in pCG1 and pCG2 were verified by sequence analysis and found to correspond exactly to the sequence of the template DNA of pKG4322.

In a similar way, one fragment of the target sequence was obtained by PCR on template pKG4322 DNA using primers 13 and 14, which resulted in a 398 bp amplification product with restriction sites for BamHI and SacI on either end. The second fragment of the target sequence was obtained on pKG4322 DNA as template with primers 15 and 16, resulting in an amplification product of 698 bp, of which the first 398 bp were identical to the fragment obtained with primers 13 and 14 and which extended another 300 bp in the 3' direction. This product contained restriction sites for BamHI and XbaI on either end. Both fragments were cloned in T/A cloning vector pCR2.1 to create plasmids pKG4347 and pKG4349, respectively.

Yet another set of amplification reactions was designed to obtain larger fragments of the target sequence. In a similar way as described above, one 805 bp PCR product of the target sequence was obtained with primers 13 and 17 with restriction sites fob SacI and BamHI on either end, and a second 1102 bp product was obtained with primers 15 and 18 and contained restriction sites for BamHI and XbaI on either end. The sequence of the first 805 bp of the second PCR product was identical to the sequence of the first PCR product, while the second product extended for another 297 bp in the 3' direction. Both fragments were cloned in T/A cloning vector pCR2.1 to create plasmids pKG4351 and pKG4346, respectively.

1.4. Construction of Hairpin RNA Encoding Transformation Vectors

Figure 9A:
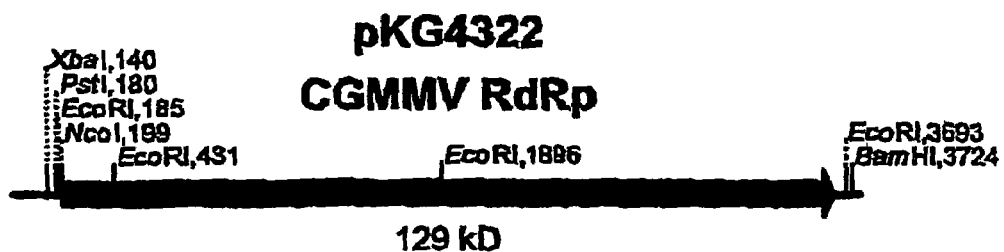
FIG. 9a shows the construct pKG4322.
Figure 9B:
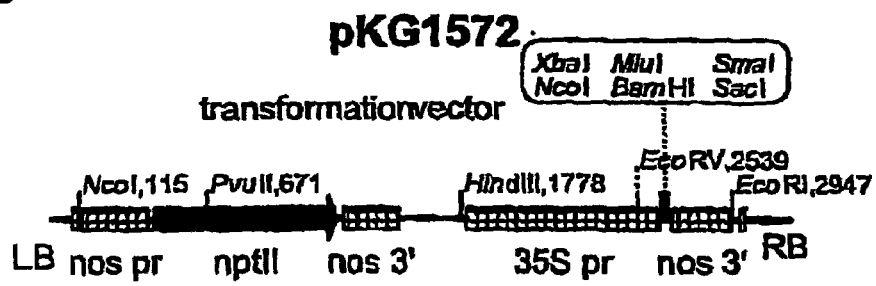
FIG. 9b shows the construct pKG1572.
Figure 9C:
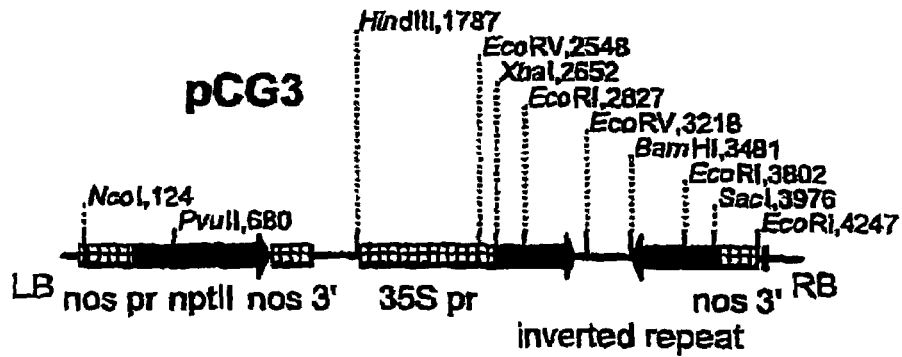
FIG. 9c shows the construct pCG3.
Figure 10A:
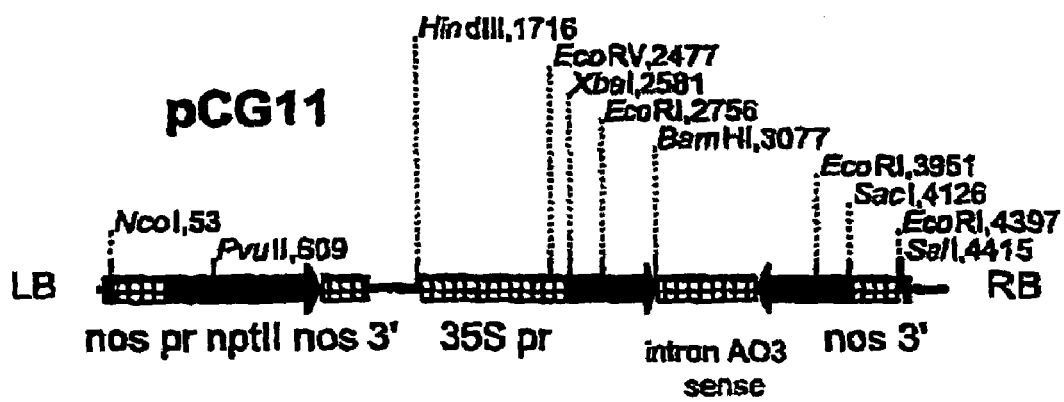
FIG. 10a shows the construct pCG11.
Figure 10B:
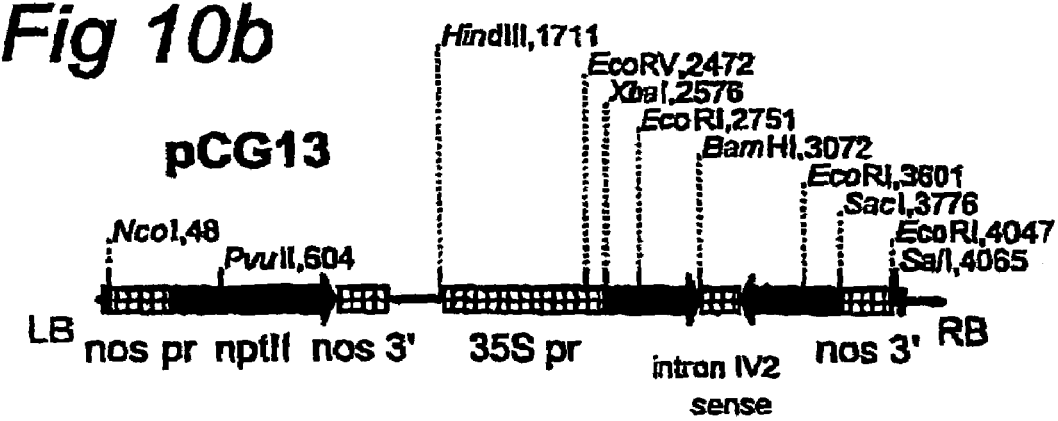
FIG. 10b shows the construct pCG13.

The restriction sites on the ends of the amplified target sequences allowed the simultaneous cloning of both fragments by a three-way ligation in a suitable transformation vector such as pKG1572. This information vector is a cointegrate type T-DNA vector for Agrobacterium—mediated transformation of plants, carrying between the T-DNA borders a) the plant selectable marker gene nptII driven by a nos promoter, b) a CaMV 35S promoter for constitutive expression in plants, c) a multiple cloning site, and d) the nos polyadenylation sequence (FIG. 9). Furthermore, this vector contain a backbone sequence homologous to pBR322, including tie ColE1 origin of replication for maintenance in E. coli, and the aadA selectable marker gene for bacterial resistance to streptomycin and spectinomycin.

The presence of the restriction sites for BamHI at both 3' ends of the PCR products allowed the insertion of both fragments in reverse orientation to each other in the cloning vector. Thus, a construct was created, that included the target sequence of 489 bp in reverse orientation, separated by a 'stuffer' fragment of 332 bp, that was included in the amplification product generated with primers 3 and 4, This 'stuffer' fragment is included to guarantee stability of the inverted repeat sequences in E. coli. The construct obtained by the three-way ligation was named pCG3 and was transformed to E. coli MC1061 and stored at −80° C. The pCG3 can construct was verified by sequence analysis.

Figure 11:
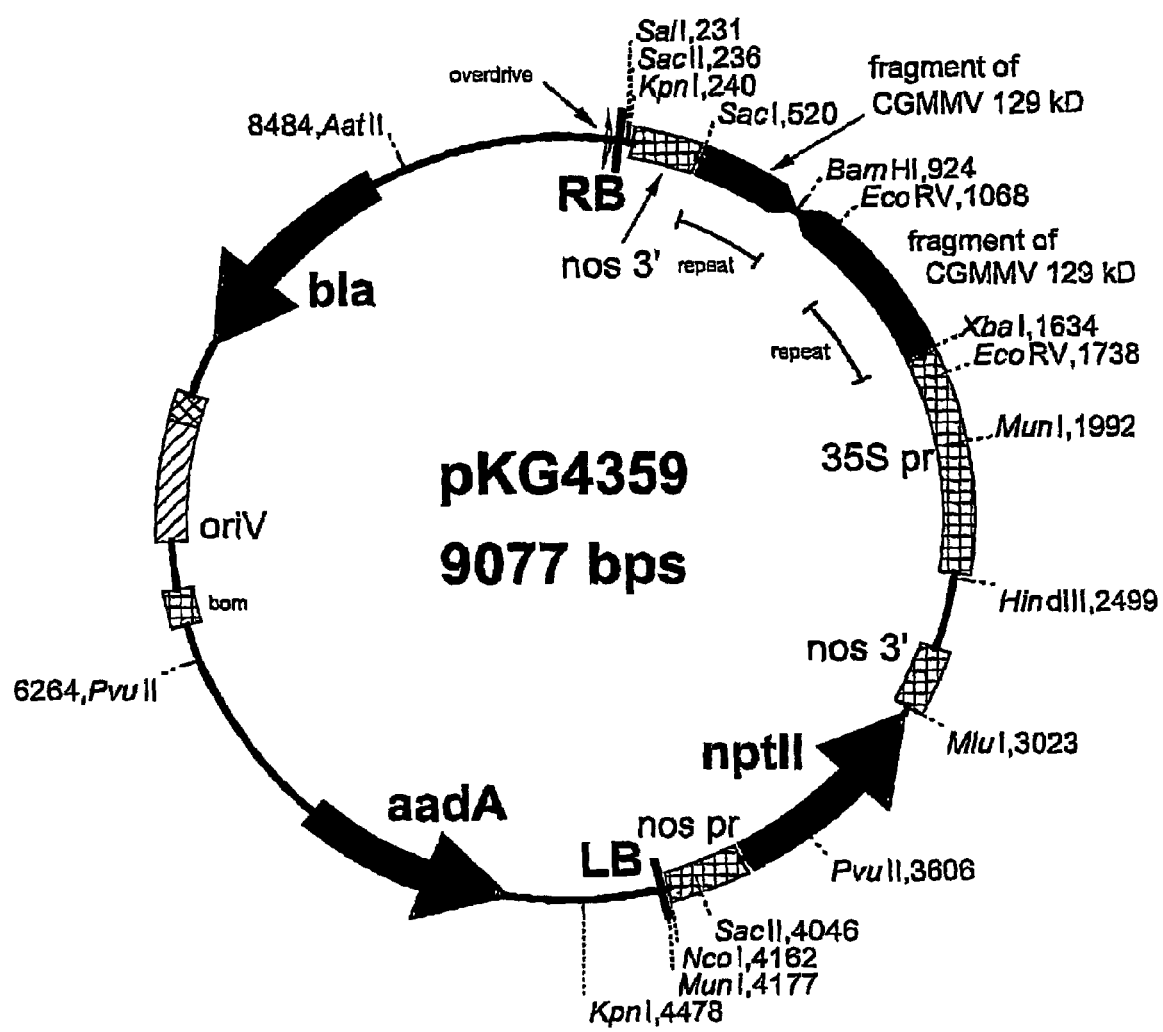
FIG. 11 shows the plasmid construct pKG4359.

In a similar way, the cloned PCR products of pKG4347 and pKG4349 were inserted in transformation vector pKG1572 in a 3-way ligation, resulting in inverted repeat orientation of the 398 bp identical parts of the products, separated by a 300 bp 'stuffer' sequence. The resulting transformation vector was named pKG4359 (FIG. 11).

Figure 12:
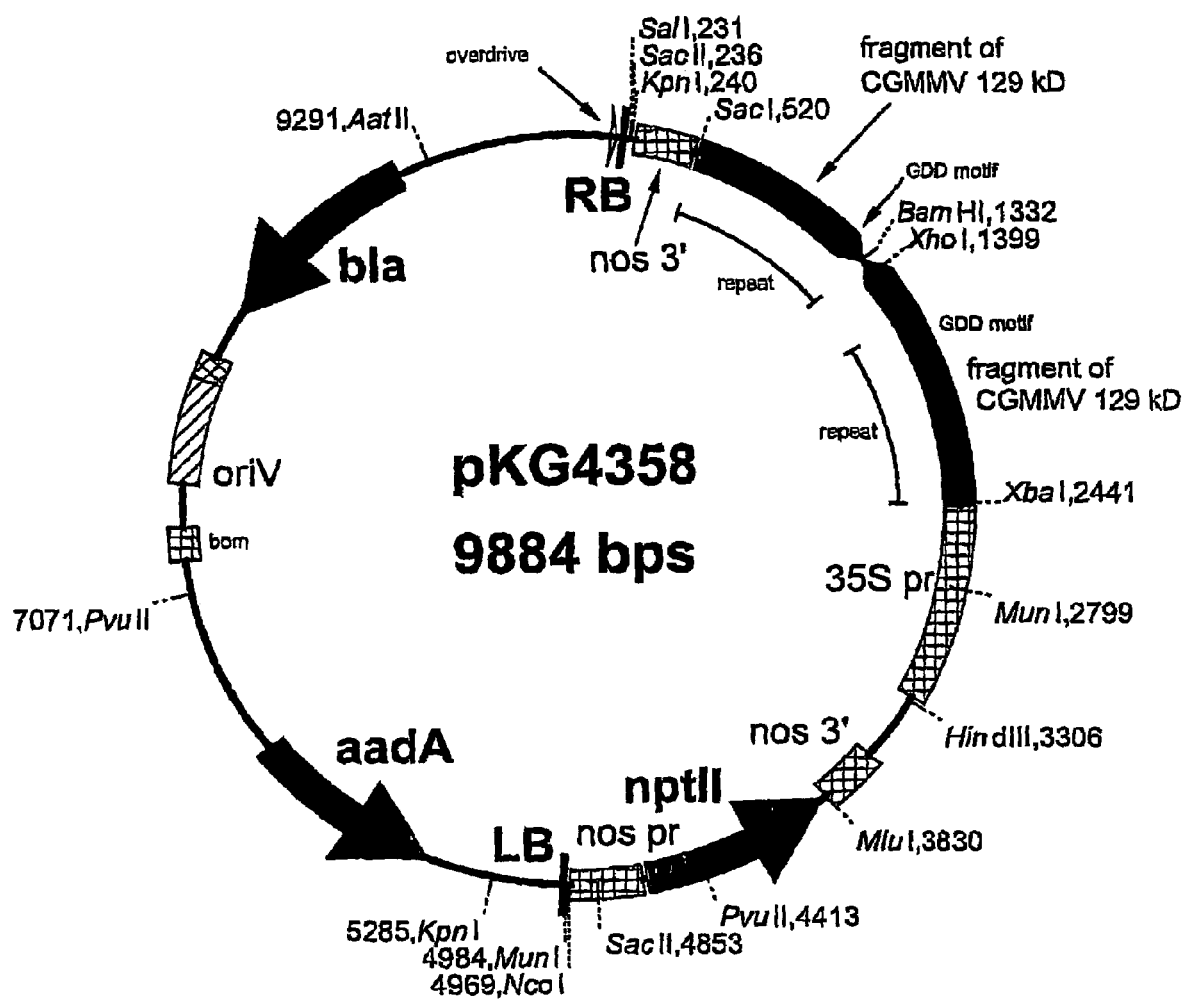
FIG. 12 shows the plasmid construct pKG4358.

Similarly, the PCR products of pKG4351 and pKG4346 were inserted in a 3-way ligation in transformation vector pKG1572 to create pKG4358 (FIG. 12), consisting of 805 bp inverted repeats of the CGMMV target sequence, separated by a 297 bp 'stuffer'. All constructs were transformed to E. coli MC1061 and stored at −80° C.

1.5. Transformation of Cucumber

Transformation vector pCG3 was subsequently transferred to the disarmed Agrobacterium tumefaciens strain GV2260 by tri-parental mating. Strain GV2260 carries in its Ti-plasmid pGV2260 a 3.8 kb sequence of pBR322, homologous to a similar fragment of pBR322 residing in the backbone of the cointegrate transformation vectors such as pKG1572 and pCG3. This homologous sequence allows the stable integration of the transformation vector into the Ti-plasmid by homologous recombination.

Agrobactrium colonies were grown and subcultured on streptomycin end spectinomycin to select for the presence of the integrated transformation vector. Selected colonies were subjected to Southern blot analysis with the aadA selectable marker gene present on the cointegrate vector as a probe to verify single integration events in the Ti-plasmid. Furthermore, the Agrobacterium colonies were subjected to PCR analysis using primer sets capable of amplifying overlapping fragments covering the entire T-DNA of the integrated transformation vector to verify the correct integration in the Ti-plasmid of the complete T-DNA. A number of Agrobacterium colonies verified in this way were named GV2260 (pGV2260::pCG3) and were stored at −80° C.

In a similar way, the transformation vectors pKG4358 and pKG4359 were transferred to Agrobacterium GV2260. These were named GV2260 (pGV2260::pKG4358) and GV2260 (pGV2260::pKG4359), respectively.

The hairpin RNA encoding constructs are introduced into the genomes of cucumber plants using Agrobacterium-mediated transformation procedures known i the art. Briefly, cotyledon explants of young cucumber seedlings germinated in vitro are inoculated with a suspension of an Agrobacterium strain containing any one of the previously described transformation constructs integrated on their Ti-plasmids. The explants, after 1 to 5 days of cocultivation with Agrobacterium, are transferred to Petri dishes with regeneration medium containing, in addition to minerals, vitamins, sugars and plant growth regulators, kanamycin sulphate in concentrations of 50 to 300 mg/l as a selective aged, and incubated in growth chambers under the appropriate temperature and light conditions for the specific cucumber cultivar under study. The cotyledon explants will, in the course of the following weeks, produce primordia, that grow out to shoots. When the shoots have grown sufficiently long, the are transferred to glass jars with rooting medium containing the selective agent kanamycin sulphate. Truly transformed shoots will remain green and form roots on this medium, are ultimately hardened off transplanted to soil and transferred to a greenhouse. Viral resistance assays are preferably performed on young seedlings originating from crosses between transformed maternal cucumber plants and a pollinator line. Virus resistance assays can simply be carried out by mechanical inoculation of the seedlings with a crude extract in phosphate buffer of leaves of a severely diseased cucumber plant previously infected. The resistance phenotype is observed 21 days post-inoculation by absence of leaf chlorosis and stunted growth, which has become apparent in non-transgenic control sets. Depending on the number of independently integrated copies of the gene construct in the plant genome, the number of resistant seedlings versus the number of susceptible seedlings will correspond to a Mendelian segregation.

The resistance against virus infection obtained may be expressed as the degree of tolerance, by scoring the period in number of days post-infection which it takes for 50% of transformed seedlings in the infected population to show symptoms of virus infection. In many cases, however, the resistance to CGMMV infection obtained by hairpin RNA constructs is sufficiently effective that a score of 50% of transformed seedlings showing symptoms will not be observed within a period of several months. In such case, all seedlings remaining free of symptoms 21 days post-inoculation are scored as being resistant, and the number of resistant seedlings out of the total number of infected transformed seedlings is expressed as a percentage of effectiveness of resistance. In this way, differences in the effectiveness of the various described intron-spliced hairpin RNA constructs in conferring virus resistance are evaluated.

The virus resistance assays described above can be performed using inoculations of viral isolates of different origin. In this way, the intron-spliced hairpin RNA constructs targeted again CGMMV are shown to be effective against all isolates of CGMMV described in Table 1, including the Japanese isolate CGMMV-SH, as well as to isolates of the related cucurbit-infecting tobamoviruses Kyuri Green Mottle Mosaic Virus (KGMMV) and Cucumber Fruit Mottle Mosaic Virus (CFMMV).

EXAMPLE V

2.1. Cloning of Plant Intron Sequences

In a second example, an alternative 'stuffer' fragment necessary for stable maintenance of the inverted repeat structure in *E. coli* is chose in this case, use is made of a plant intron sequence capable of being spliced after transcription of the inverted repeat sequence in plant cells. The publication of Smith et al. (Nature 407: 319-320, 2000) describes the use of intron 2 of the PdK gene *Flaveria* as a 'stuffer' fragment in gene silencing constructs to obtain a high degree of resistance to infections with PVY. However, this *Flaveria* intron is very large (1.8 kb) and the correct splicing of this intron in *Cucumis* plant cells is uncertain. In this example, two types of plant introns are employed, of which the correct splicing in *Cucumis* has been verified. The intron is the 188 bp IV2 intron of the potato LS-1 gene, that is frequently encountered in gusA reporter gene constructs to obtain expression of beta-glucuronidase in plant cells with simultaneous absence of beta-glucuronidase expression in bacterial cells such as *Agrobacterium tumefaciens*. From experience it is known that cucumber and melon plants correctly express beta-glucuronidase from introduced gene constructs containing the gusA gene with the potato IV2 intron.

The second intron employed is the 532 bp *Cucumis melo* ascorbate oxidase intron AO3, which by its very nature is known to be spliced correctly in *Cucumis melo* (melon plants and is expected to function properly in the related species *Cucumis sativus* (cucumber).

Both these intron sequences were obtained by PCR amplification using primers, which, in the 5' part of the primer sequences, include an additional restriction site to facilitate the cloning of the amplification products. Thus, melon intron AO3 was amplified from total genomic DNA of young melon seedlings using primers 5 and 7 (see Table 9), which each contains a restriction site fox BamHI or BglII, respectively, at their 5' ends.

An alternative PCR reaction to obtain gene melon AO3 intron employed primers 19 and 20, and yielded a PCR product with 546 bp of amplified intron sequence, which corresponded to the known AO3 intron sequence, and which contained restriction sites for BamHI and BglII on either end. This PCR product was cloned in the T/A cloning vector pCR2.1 to yield plasmid pKG4355.

In order to test the effect of the cloned intron sequences in the hairpin RNA encoding gene constructs, control gene constructs were anticipate in which the intron sequences were placed in reverse orientation. To this end, a similar primer set was designed, consisting of primers 6 and 8, in which the restriction sites for BamHI and BglII were reversed as compared to primers 5 and 7 (Table 9). The PCR products obtained by amplification of the AO3 intron sequence using said primer sets were cloned in T/A cloning vector pCR2.1, resulting in pCG4 (BamHI-AO3 intron-BglII) and pCG5 (BglII-AO3 intron-BamHI). The sequences of the cloned PCR products were verified by sequence analysis and found to correspond exactly to the known sequences of intron.

The potato IV2 intron was amplified from the vector construct pKGT-3 carrying a gusA gene containing this intron with primes 9 and 11 (see Table 9), each carrying an additional restriction site for BamHI and BglII, respectively. Also for this intron, an additional PCR product with BamHI and BglII at the removed positions on either side of the amplification product was using PCR primers 10 and 12 (Table 9). The PCR products thus obtained were cloned in cloning vector pCR2.1, and named pCG6 (BamHI-potato IV2 intron-BglII) and pCG7 (BglII-potato IV2 intron-BamHI).

An alternative reaction to obtain the potato IV2 intron for cloning in the correct orientation employed primers 21 and 22 in a PCR reaction on template DNA of pKG1600, a plasmid vector containing the gusA gene of this intron. The reaction yielded an amplification product with 202 bp of IV2 intron sequence, and which contained restriction sites for BamHI and BglII on either end. This PCR product was cloned in the T/A cloning vector pCR2.1 to yield plasmid pKCG4353.

2.2. Cloning of Introns in the Hairpin RNA Encoding Expression Cassettes

The target sequence of 489 bp of the CGMMV RdRP gene was reamplified from the cloned CGMMV RdRp gene in vector pKG4322 by PCR using primer 2 and primer 3, as described in Example IV. This PCR reaction produced a fragment containing the target sequence, that was identical to the insert of pCG1 of Example IV) except that the 5' restriction site generated at the 5' end of the PCR product is a recognition site XbaI instead of for SacI. The PCR product was cloned in T/A vector pCR2.1 to produce pCG8. The ligation product was transformed to *E. coli* MC1061 and stored at −80° C. The sequences of the cloned PCR product in pCG8 was verified by sequence analysis and found to correspond exactly to the sequence of the template DNA of pKG4322.

In a similar way, the 398 bp CGMMV target sequence was reamplified from pKG4322 template DNA using primers 23 and 14 to create restriction sites for BamHI and XbaI on either end, to facilitate the cloning in intron-containing repeat constructs. This PCR fragment, after cloning in the T/A cloning vector pCR2.1, was named pKG4348.

Yet in another, similar, PCR reaction, an 806 bp CGMMV target sequence was reamplified from pKG4322 template DNA using primers 23 and 24 to create restriction sites for BamHI and XbaI on either end, to facilitate the cloning in intron-containing repeat constructs. This PCR fragment, after cloning in the T/A cling vector pCR2.1, was named pKG4350.

The vector pCG1 of Example IV was digested with restriction enzymes SacI and BamHI and the rent containing the 489 bp target sequence was isolated from gel and ligated into the transformation vector pKG1572 (described in Example IV) digested with the same two restriction enzymes. This ligation product, named pCG9, was transformed to *E. coli* MC1061. The correct structure of pCG9 was then verified by restriction analysis.

Next, both plant intron sequences in sense and in antisense orientations, cloned in vectors pCG4 to pCG7 were isolated from their vectors by digestion with BamHI and BglII and ligated into pCG9 digested with BamHI. The ligation products were transformed to *E. coli* MC1061. This cloning step placed the plant intron sequences next to the 489 bp CGMMV target sequence in the expression cassette of the transformation vector. Since restriction enzymes BamHI and BglII are isoschizomers and produce identical 'sticky ends', two orientations of the intron sequences were obtained in the ligation products. Colonies of all four cloning reactions were analysed by restriction enzyme digestion, and only those colonies of all four reactions were retained for further cloning, that contained the single BamHI site at a position between the in sequence and the CaMV 355 promoter. The cloning intermediates were named pCG10 (sense AO3 intron), pCG12 (sense IV2 intron), pCG14 (antisense AO3 intron) and pCG16 (antisense IV2 intron).

Figure 13:
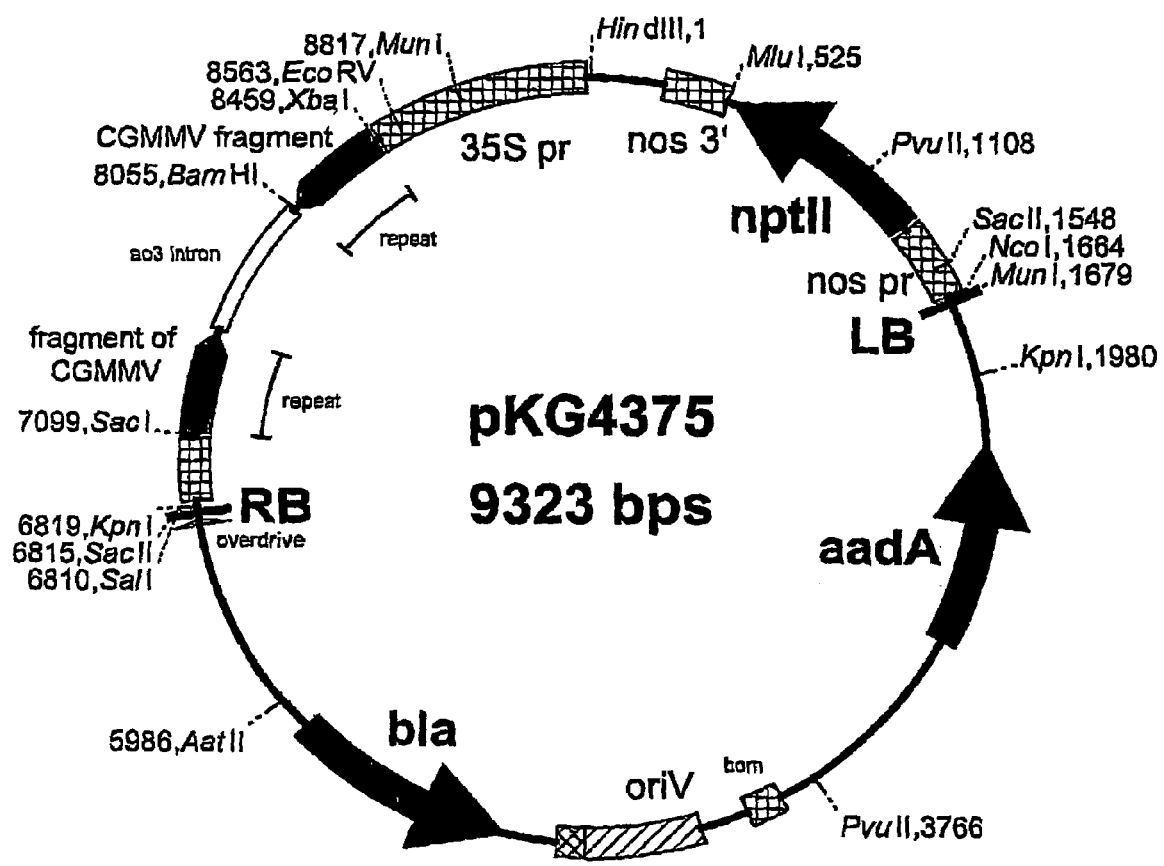
FIG. 13 shows the plasmid construct pKG4375.
Figure 14:
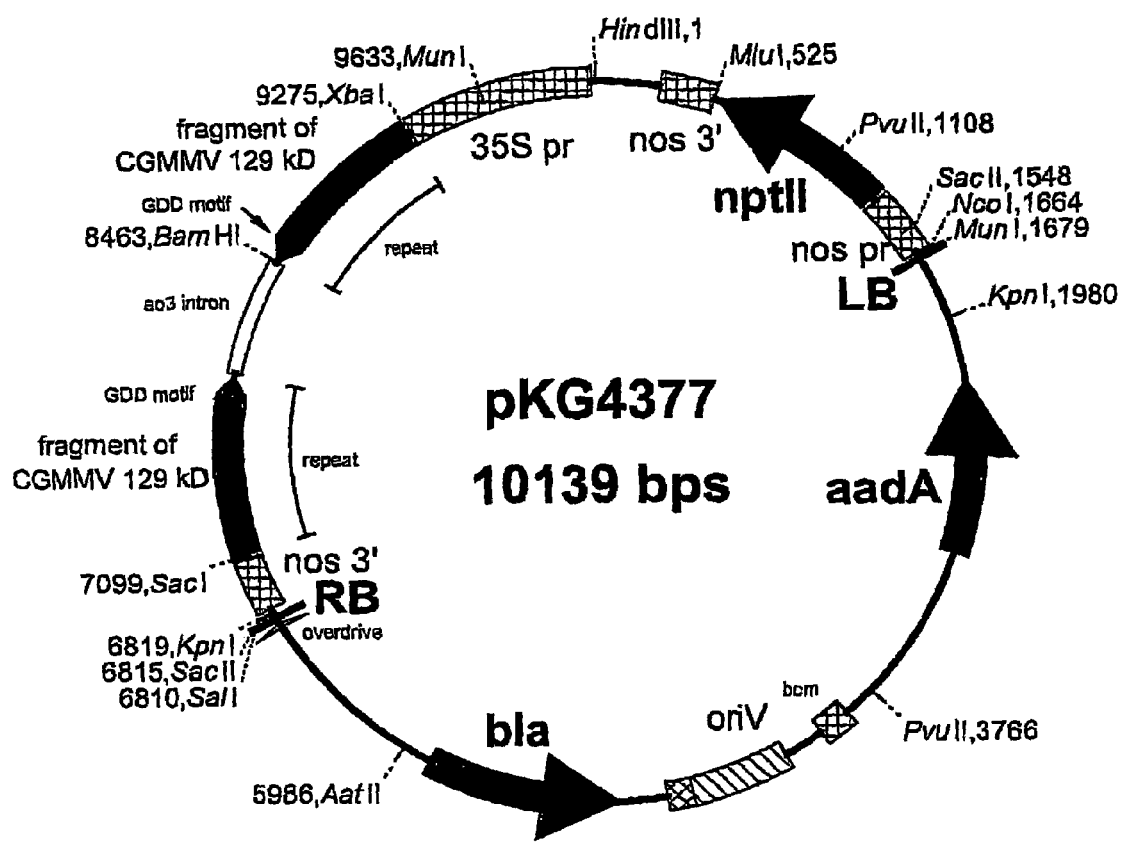
FIG. 14 shows the plasmid construct pKG4377.
Figure 15:
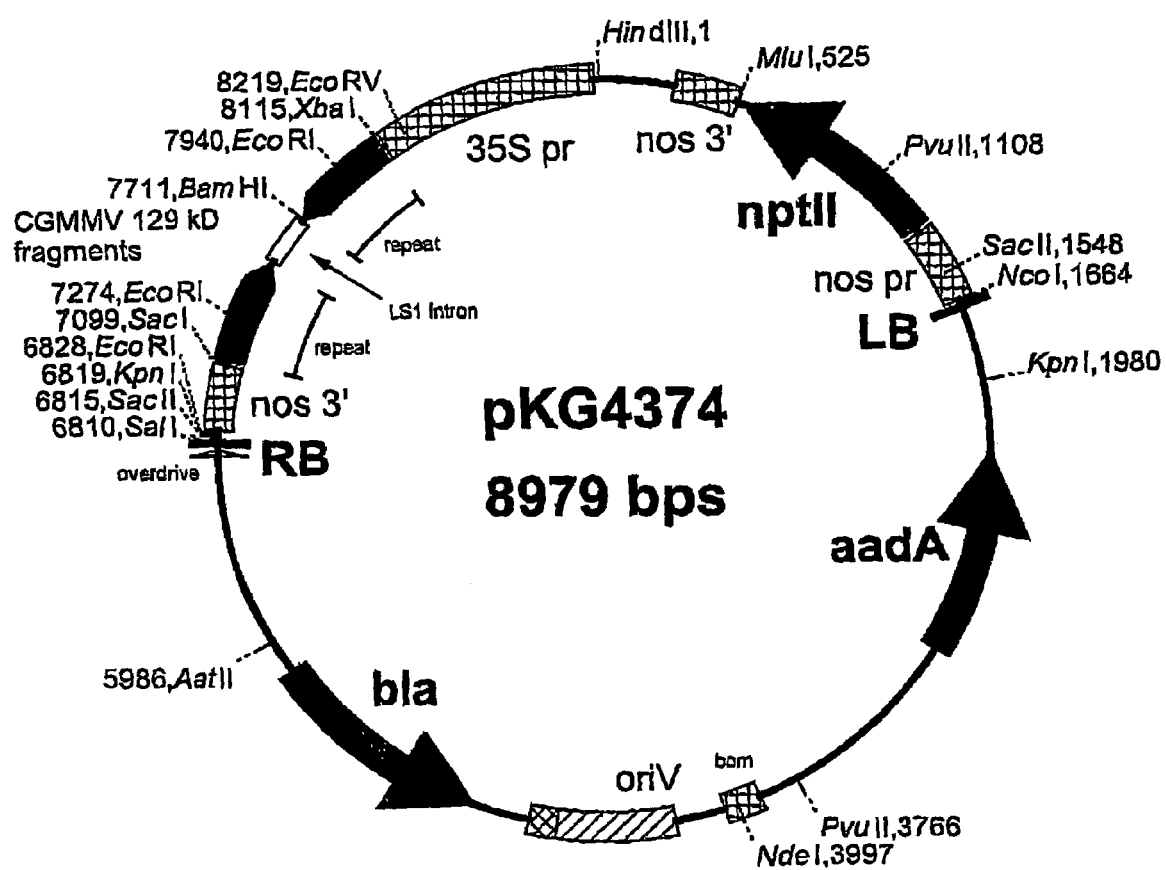
FIG. 15 shows the plasmid construct pKG4374.
Figure 16:
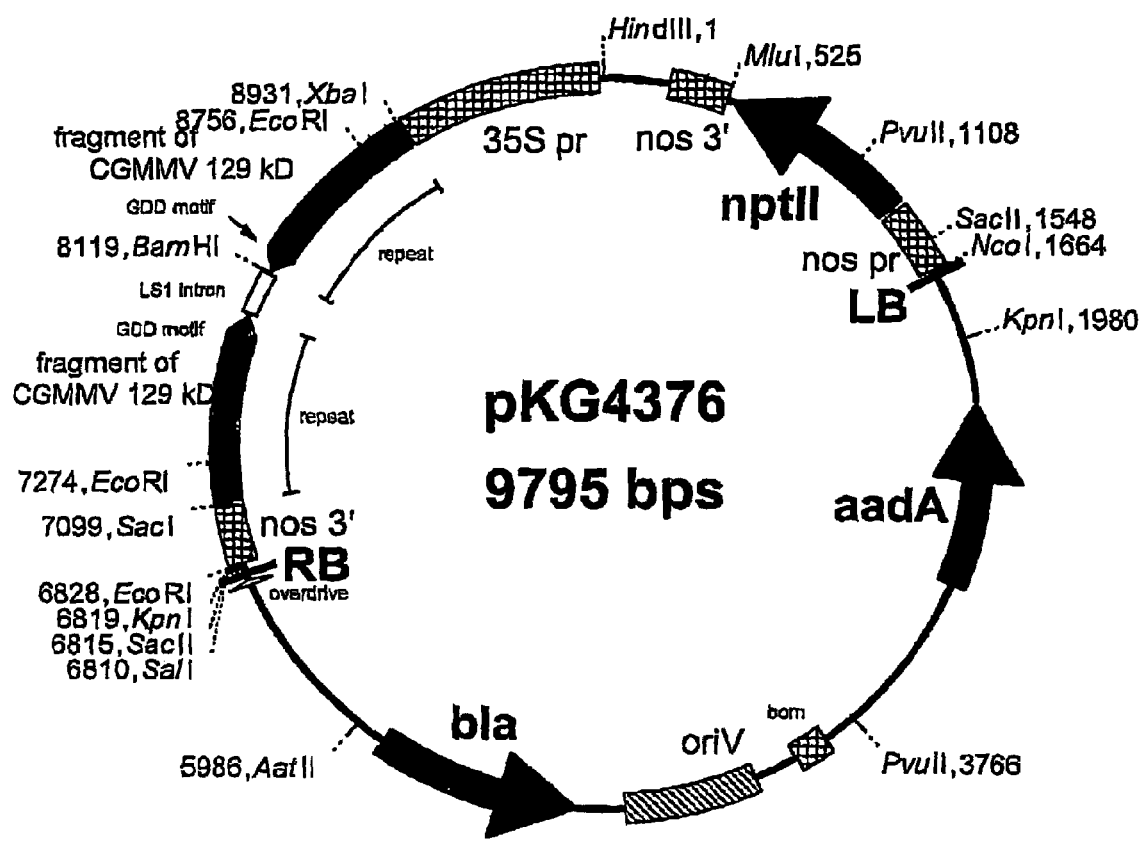
FIG. 16 shows the plasmid construct pKG4376.

Subsequently, the 489 bp target sequence of pCG8 was isolated from the vector by digestion with XbaI and BamHI and ligated into the vectors pCG10, pCG12, pCG14 and pCG16, each digested with XbaI and BamHI. This Ligation step produced the final transformation vectors containing two copies of the 489 bp target sequence in reverse orientation to each other, thus encoding a hairpin RNA structure, and separated from each other by plant intron sequences in sense and antisense orientation The ligation products were named pCG11 (sense AO3 intron), pCG13 (sense IV2 intron), pCG15 (antisense AO3 intron) and pCG17 (antisense IV2 intron), and were transformed to *E. coli* MC1061 and stored at −80° C. The correct structure of the vectors was verified by sequence analysis, The other cloned amplification products of target and intron sequences described in this example were assemble in the follow manner. The melon AO3 intron of pKG4355, as a BamHI-BglII fragment, and the 398 bp CGMMV RdRp target sequence of pKG4347, as a BamHI-SacI fragment, were simultaneously ligated in the transformation vector pKG1572. Subsequent insertion of a BamHI-XbaI fragment of pKG4348 into the ligation product yielded transformation vector pKG4375 (FIG. 13), which carried inverted repeats of the 398 bp CGMMV RdRp target sequence, separated by the melon AO3 intron.

To create a similar construct with the longer CGMMV target sequences, tie melon AO3 intron of pKG4355, as a BamHI-BglII fragment, and the 805 bp CGMMV RdRp target sequence of pKG4351, as a BamHI-SacI fragment were simultaneously ligated in the transformation vector pKG1572. Subsequent insertion of a BamHI-XbaI fragment of pKG4350 into the ligation product yielded transformational vector pKG4377 (FIG. 14), which carried inverted repeats of the 805 bp CGMMV RdRp target sequence, separated by the melon AO3 intron.

Likewise, transformation vectors with CGMMV RdRp inverted repeats separated by the potato IV2 intron were created. The potato IV2 intron of pKG4353, as a BamHI-BglII fragment, and the 398 bp CGMMV RdRp target sequence of pKG4347, as a BamHI-SacI fragment, were simultaneously ligated in the transformation vector pKG1572. Subsequent insertion of a BamHI-XbaI fragment of pKG4348 into the ligation product yielded transformation vector pKG4374 (FIG. 15), which carried inverted repeats of the 398 bp CGMMV RdRp target sequence, separated by the potato IV2 intron.

Also, the potato IV2 intron of pKG4353, as a BamHI-BglII fragment, and the 805 bp CGMMV RdRp target sequence of pKG4351, as a BamHI-SacI fragment, were simultaneously ligated in the transformation vector pKG1572. Subsequent insertion of a BamHI-XbaI fragment of pKG4350 into the ligation product yielded transformation vector pKG4376 (FIG. 16), which carried inverted repeats of the 805 bp CGMMV RdRp target sequence, separated by the potato IV2 intron.

All constructs were transformed to *E. coli* MC1061 and stored at −80° C.

2.3. Transformation of Cucumber

After transferred the transformation vectors to *Agrobacterium tumefaciens* strain GV2260 as described in Example IV, cucumber plants transformed with these *Agrobacterium* strains will be resistant to CGMMV infection. The preferred manner to assay virus resistance is described in Example IV. With all four gene constructs resistance to CGMMV infection is obtained. The efficacy of the intron sequences in sense orientation as opposed to constructs with introns in antisense orientation is apparent from the high percentage of cucumber lines showing extreme resistance to CGMMV infection.

Hereinabove, the invention has been described under the assumption that resistance against CGMMV is generated “at the protein level”, i.e. that the “nucleotide sequence encoding a defective variant of the replicase gene of CGMMV” codes for a “defective replicase”, the expression of which at cellular level generates the desired resistance against CGMMV. Hereinabove, the invention has been described under the assumption, that the resistance to CGMMV can also be generated at the RNA-level, e.g. down-regulation of gene expression due to RNA sequence homology. However, the invention is not limited to any explanation or mechanism, and is not particularly limited to the use of a particular type of nucleotide sequence (i.e. encoding a “defective replicase” or a “hairpin”).

REFERENCES

Anderson, J. M., Palukaitis, P. and M. Zaitin (1992) A defective replicase gene induces resistance to cucumber mosaic virus in transgenic tobacco. Proc.Nat.Acad.Sci.USA 89: 8759-8763.

Audy et al. (1993) Molec.Plant-Microbe Interact 7: 15-23.

Beachy, R. N., S. Loesch-Fries and N. Turner (1990) Coat-protein mediated resistance against virus infection. Ann.Rev Phytopathology 28: 451-474.

Christou et al. (1992) IAPTC Newsletter 2-14.

Cooper et al. (1995) Virology 206: 307-313.

Depicker et al. (1982) J.Mol.Appl.Genet. 561-573.

Donson, J., C. M. Kearney, T. H. Turpen, I. A. Khan, G. Kurath, A. M. Turpen, G. E. Jones, W. O. Dawson and D. J. Lewendowski (1993) Broad Resistance to Tobamoviruses is mediated by a modified Tobacco Mosaic Virus Replicase Transgene. Mol.Plant-Microbe Interact 6: 635-642.

Goldbach, R, and P. De Haan (1993) Prospects of engineered forms of resistance against tomato spotted wilt vim. Seminars in Virology 4: 381-387.

Golemboski, D. B., G. P. Lomonosoff and M. Zaitlin (1990) Plants transformed with a tobacco mosaic virus nonstructural gene sequence are resistant to the virus. Proc. Natl. Acad. Sci.USA 87: 6311-6315.

Hollings, M., Y. Komuro and H. Tochihara (1975) Cucumber Green Mottle Mosaic Vu. C. M. I./A. A. B. Descriptions of Plant Viruses, nr. 154.

Horsch, R. B., J. G. Fry, N. L. Hoffmann, D. Eichholtz, S. G. Rogers and R. T. Fraley (1985) A simple and general method for transferring genes into plants. Science 227: 1229-1231.

Kunik, T., R. Salomon, D. Zamir, N. Navot, M. Zeidan, I. Michelson, Y. Gafni and H. Czosnek (1994) Transgenic tomato plants expressing the tomato yellow leaf curl virus capsid protein are resistant to the virus. Bio/Technology 12, 500-504.

Meshi, T., R. Kiyama, T. Ohno and Y. Okada (1983) Nucleotide sequence of the coat protein cistron and the 3' noncoding region of cucumber green mottle mosaic virus (watermelon strain) RNA. Virology 127: 54-64.

Prins et al. (1994) Molec.Plant-Microbe Interact 8: 85-91.

Ugaki M., M. Tomiyama, T. Kakutani, S. Hidaka, T. Kiguchi, R. Nagata, T. Sato, F. Motoyoshi and M. Nishiguchi (1991) The complete nucleotide sequence of Cucumber Green Mottle Mosaic Virus (SH strain) genomic RNA J.Gen.Virol. 72; 1487-1495.

Rogers, S. G., H. J. Klee, R. B. Horsch and R. T. Fraley (1986) Gene transfer in plants: production of transformed plants using Ti plasmid vectors. Meth. Enzymol. 118: 627-640.

Shillito, R. D., M. W. Saul, J. Paszkowski, M. Muller and I. Potrykus (1985) High efficiency direct gene transfer to plants. Bio/Technology 3: 1099-1103.

Vaira, A. M, L. Semeria, S. Crespi, V. Lisa, A. Allavena and G. P. Accotto (1995) Resistance to Tosposviruses in Nicotiana benthamiana transformed with the N gene of tomato spotted wilt virus: correlation between transgene expression and protection in primary transformants. Molec.Plant-Microbe Interact. 8; 66-73.

Vorts O., P. Kock, A. lever, B. Weterings, P. Weisbeek and S. Smeekens (1993) The promoter of the *Arabidopsis thaliana* plastocyanin gene contains a far upstream enhancer-like element involved in chloroplast-dependent expression. Plant Journal 4:933-945.

Wilson, T. M. A. (1993) Strategies to protect crop plants against viruses: pathogen-derived resistance blossoms. Proc.Natl.Acad.Sci.USA 90: 3143-3141.

The invention claimed is:

1. A method for generating resistance in a plant or in a plant cell against infection with Cucumber Green Mottle Mosaic Virus (CGMMV), comprising generating a transformed plant or plant cell by transforming a plant or plant cell with one or more polynucleotide sequences that upon transcription into RNA generate resistance against infection with CGMMV in said plant and produce a sense and an antisense RNA molecule capable of forming a double stranded RNA region by base-pairing between the regions which are complementary, said polynucleotide sequences comprising a first and a second DNA sequence, wherein:

said first DNA sequence comprises a promoter, operably linked to a first DNA region capable of being transcribed into a sense RNA molecule with a nucleotide sequence comprising a sense nucleotide sequence of at least 100 consecutive nucleotides having 100% sequence identity with the replicase encoding nucleotide sequence of the genome of the CGMMV virus capable of infecting the plant or the plant cell;

said first DNA sequence optionally further comprises a DNA region involved in transcription termination and polyadenylation functioning in plant cells operably linked to said first DNA region; and said second DNA sequence comprises a second DNA region capable of being transcribed into an antisense RNA molecule with a nucleotide sequence comprising an antisense nucleotide sequence including at least 100 consecutive nucleotides, having 100% sequence identity with the complement of said at least 100 consecutive nucleotides of the sense nucleotide sequence;

said second DNA sequence optionally further comprises a promoter operably linked to said second DNA region and optionally a DNA region involved in transcription termination and polyadenylation functioning in plant cells operably linked to said second DNA region, and wherein said replicase encoding nucleotide sequence of the genome of the CGMMV virus is:

(A) the nucleotide sequence of SEQ ID NO:1;

(B) the nucleotide sequence of SEQ ID NO:5; or (C) the nucleotide sequence of SEQ ID NO:3.

2. The method according to claim 1, wherein the transformed plant is generated by crossing transformed parent plants comprising either the first or the second DNA sequence.

3. The method according to claim 1, wherein the transformed plant is generated by transforming a plant cell with the first and second DNA sequence and regenerating a plant from the transformed plant cell.

4. The method according to claim 1, wherein the first and second DNA sequence are integrated separately in the nuclear genome of the plant cell.

5. The method according to claim 1, wherein the polynucleotide sequence is transcribed into an inverted repeat RNA sequence, optionally linked by a spacer and wherein the spacer is preferably an intron.

6. The method according to claim 1, further comprising at least one step of cultivating the transformed plant cell into a mature plant.

7. The method according to claim 1, further comprising at least one step of sexually or asexually reproducing or multiplying the transformed plant and/or a mature plant obtained from the transformed plant cell.

8. The method according to claim 1, in which the plant is a plant that is susceptible to infection with CGMMV, more preferably a plant belonging to the Cucurbitaceae family, such as melon (*Cucumis melo*), cucumber (*C. sativus*), watermelon (*Citrullus vulgaris*) and bottlegourd (*Lagenaria siceraria*).

9. A transgenic plant or plant cell, obtainable or obtained by a method according to claim 1, or a descendant of such a plant; wherein the plant, plant cell, or descendant comprises said polynucleotide sequences.

10. The transgenic plant or plant cell or descendent according to claim 9, wherein said plant or plant cell or descendent is resistant against infection with strains of CGMMV prevalent in Europe.

11. The plant according to claim 9, being a plant that is susceptible to infection with CGMMV, more preferably a plant belonging to the Cucurbitaceae family, such as melon (*Cucumis melo*), cucumber (*C. sativus*), watermelon (*Citrullus vulgaris*) and bottlegourd (*Lagenaria siceraria*).

12. A cultivation material such as seed, tubers, roots, stalks, seedlings of a plant according to claim 9; wherein said cultivation material comprises said polynucleotide sequences.

13. The method according to claim 1, wherein the sense RNA molecule comprises a sense nucleotide sequence of at least 150 consecutive nucleotides having 100% identity with the replicase encoding nucleotide sequence of the CGMMV virus genome.

14. The method according to claim 1, wherein said transformed plant or plant cell is resistant against infection with strains of CGMMV prevalent in Europe.

15. The method according to claim 14, wherein said CGMMV strains prevalent in Europe are strains encountered in the cultivation of cucumbers in greenhouses.

16. The method according to claim 1, wherein the sense RNA molecule comprises a sense nucleotide sequence of at least 200 consecutive nucleotides having 100% identity with the replicase encoding nucleotide sequence of the CGMMV virus genome.

17. The method according to claim 1, wherein the sense RNA molecule with a nucleotide sequence comprises a sense nucleotide sequence of at least 550 consecutive nucleotides having 100% sequence identity with the replicase encoding nucleotide sequence of the CGMMV virus genome.

* * * * *

SEQUENCE LISTING

```
<160> NUMBER OF SEQ ID NOS: 68

<210> SEQ ID NO 1
<211> LENGTH: 3432
<212> TYPE: DNA
<213> ORGANISM: Cucumber green mottle mosaic virus
<220> FEATURE:
<223> OTHER INFORMATION: DNA sequence encoding 129 kD replicase of CGMMV

<400> SEQUENCE: 1
atggcaaaca ttaatgaaca aatcaacaat caacgtgatg ctgctgctag cgggagaaat      60
aatctcgtta gtcagctagc atcaaagagg gtgtatgacg aggccgttcg ctcgttagat     120
catcaagata gacgcccaaa aatgaacttt tctcgtgtgg tcagtacaga gcacaccagg     180
cttgtcaccg atgcgtatcc ggagttttcg attagtttca ccgctaccaa gaattcagtt     240
cattcccttg cgggaggttt gaggcttctt gaattggaat acatgatgat gcaggtgcct     300
tatggttcac cttgctttga tattggcggt aattacacgc agcatttatt taaaggtaga     360
tcatatgtgc attgctgcaa tccgtgcctg gatcttaagg atgttgcgag gaatgtgatg     420
tacaacgaca tgatcacaca acatgtacag aggcacaaag gatctggtgg gtgtagacct     480
cttccgactt tccagataga tgctttcagg aggtatgaag attcgcccgt cgcagtcacc     540
tgtccagacg tttttcaaga atgctcctat gattttggga gtggtaggga taatcatgcg     600
gtttcattac attcgattta tgatatccct tattcttcga ttgggccagc tcttcatagg     660
aaaaacgtca gggtctgtta cgcagccttt catttctcgg aggcgttgct cctaggttcg     720
cccgtgggta atttaaatag tatagggggct caatttaggg ttgatggtga cgatgtgcat     780
tttcttttta gtgaggagtc aactttgcat tacactcata gtttggagaa tattaagttg     840
attgtaatgc gtacttattt ccctgctgat gataggttcg tgtatattaa ggagtttatg     900
gttaagcgtg tagacacttt ttttttagg ttagttaggg cagacacaca tatgctccat     960
aaatctgtag ggcactattc gaagtcgaaa tctgagtatt ttgcgttgaa cacccctccg    1020
attttccaag ataaggccac gttttctgtg tggtttcccg aagcgaagcg gaaggtgttg    1080
atacctaagt ttgaactctc gagatttctt tctggaaatg tgaaagtctc taggatgctt    1140
gtcgatgctg attttgtcca taccattatt aatcacatta gcacgtacga taacaaggcc    1200
ttagtgtgga agaatgtcca gtcttttgta gaatctatac gctctagggt aattgtaaac    1260
ggagtttccg taaaatctga atggaatgta ccggtcgatc agcttactga tatctcattc    1320
tcgatattcc ttctcgtgaa ggttagaaag gtgcagattg agttaatgtc tgataaggtt    1380
gtgatcgagg cgaggggttt gcttcggagg ttcgctgata gtctcaaatc cgccgtagaa    1440
ggactaggtg attgcgtcta tgatgctcta gttcaaaccg gttggtttga cacctctagc    1500
```

-continued

```
gacgaactga aagtattact acctgaaccg tttatgacct tttcagatta tctcgaaggg     1560
atgtacgagg cagatgcaaa aattgagaga gagagtgtct ctgagctgct tgcttccgga     1620
gatgatctgt tcaagaagat tgacgaaata aggaataatt acagcggagt tgaatttgat     1680
gtggagaaat tcaagaatt ctgtaaagaa ctgaatgtta atcctatgct aatcggtcat      1740
gtgatcgaag ctattttttc acagaaggca ggggtaacag tcacgggcct aggcacgctc     1800
tctcctgaga tgggtgcttc cgttgcgtta tccaataatt ctgtagatac atgtgatgat     1860
atggacgtaa ctgaggatat ggaggaaata gtgttgatag cagacaagaa tcactcttat     1920
atttctccag aaatgtcgag atgggctagt atgaaatacg caataataa cggggcctta     1980 gttgagtaca aggtcggaac ctcgatgact ttacctgcca cctgggcaga aaagggtaag     2040
gctgttttac cgttgtcggg aatctgtgta agaaagcccc aattttcaaa gccactcgat     2100
gaggaggacg acttgaggtt atcaaacatg aatttcttta aggtgagtga tctgaagttg     2160
aagaagacta tcactccagt tgtttatact gggaccattc gagagaggca gatgaagaat     2220
tatatcgatt atctatcggc ttctctgggt tctacgcttg gtaatcttga gagaattgtt     2280
aggagtgact ggaatggtac cgaggagagc atgcaaactt ttggattgta cgattgcgag     2340
aagtgcaagt ggttactgtt gccatcggag aagaaacacg cctgggctgt agtcctggcg     2400
agtgatgata ccactcgtat aatctttctg tcgtatgacg aatccggttc tcctataatt     2460
gacaagaaaa attggaagcg gttcgctgtc tgttctgata ccaaagttta gtgtaatt      2520 cgtagtttag aagtcttaaa taaggaggcc acagtcgatc ctgggtgta tataacttta    2580 gtcgatgggg ttccgggctg tggaaaaacc gctgaaatta tagcgagggt caattggaaa    2640
actgaccttg tgttgactcc cggaagggaa gcggctgcta tgatcaggcg aagagcctgt    2700
gccctacaca agtcacctgt agctactagt gataacgtta ggacttttga ttctttcgta    2760
atgaataaga aggttttaaa atttgacgcc gtctacgtag atgaaggtct tatggtccac    2820
acggggttgc tcaactttgc gttgaagatt tcgggttgta aaaaggcctt tgtcttcggt    2880
gatgctaagc aaattccgtt tattaataga gttatgaatt ttgattatcc taaggaatta    2940
agaactttga tagttgataa tgtagagcgt aggtatatta cccataggtg tcctagagat    3000
gtcactagtt ttcttaatac tatttataaa gctgcggttt ctaccactag tccggttgta    3060
cattccgtga aggcaataaa ggtttctggg gctggtattc tgaggcccga gttgacgaag    3120
atcaaaggga agatcataac gtttactcag tctgataaac aatccttgat caagagtggg    3180
tacaatgatg tgaatactgt gcatgagatt caggggagaa cctttgagga gacggcggtt    3240
gtgcgtgcaa caccgactcc aataggtctg attgcccgag attcaccaca cgtgttagtg    3300
gctttaacgc ggcacaccaa ggcaatggtg tattataccg ttgtgttcga tgccgtaaca    3360
agcataatag cggatgtgga aaaggtcgat cagtcgattt tgactatgtt tgctactact    3420
gtgcctacca aa                                                         3432
```

<210> SEQ ID NO 2
<211> LENGTH: 1144
<212> TYPE: PRT
<213> ORGANISM: Cucumber green mottle mosaic virus
<220> FEATURE:
<223> OTHER INFORMATION: 129 kD replicase of CGMMV

<400> SEQUENCE: 2

```
Met Ala Asn Ile Asn Glu Gln Ile Asn Asn Gln Arg Asp Ala Ala Ala
 1               5                  10                  15
```

```
Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Gly Leu Arg Leu Leu Glu Leu Glu Tyr Met Met
                85                  90                  95

Met Gln Val Pro Tyr Gly Ser Pro Cys Phe Asp Ile Gly Gly Asn Tyr
                100                 105                 110

Thr Gln His Leu Phe Lys Gly Arg Ser Tyr Val His Cys Cys Asn Pro
            115                 120                 125

Cys Leu Asp Leu Lys Asp Val Ala Arg Asn Val Met Tyr Asn Asp Met
    130                 135                 140

Ile Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Glu Asp Ser Pro
                165                 170                 175

Val Ala Val Thr Cys Pro Asp Val Phe Gln Glu Cys Ser Tyr Asp Phe
                180                 185                 190

Gly Ser Gly Arg Asp Asn His Ala Val Ser Leu His Ser Ile Tyr Asp
            195                 200                 205

Ile Pro Tyr Ser Ser Ile Gly Pro Ala Leu His Arg Lys Asn Val Arg
    210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Glu Ser Thr Leu His Tyr Thr
            260                 265                 270

His Ser Leu Glu Asn Ile Lys Leu Ile Val Met Arg Thr Tyr Phe Pro
    275                 280                 285

Ala Asp Asp Arg Phe Val Tyr Ile Lys Glu Phe Met Val Lys Arg Val
290                 295                 300

Asp Thr Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
            340                 345                 350

Pro Glu Ala Lys Arg Lys Val Leu Ile Pro Lys Phe Glu Leu Ser Arg
    355                 360                 365

Phe Leu Ser Gly Asn Val Lys Val Ser Arg Met Leu Val Asp Ala Asp
370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
                405                 410                 415

Val Ile Val Asn Gly Val Ser Val Lys Ser Glu Trp Asn Val Pro Val
            420                 425                 430

Asp Gln Leu Thr Asp Ile Ser Phe Ser Ile Phe Leu Leu Val Lys Val
```

-continued

```
                435                 440                 445
Arg Lys Val Gln Ile Glu Leu Met Ser Asp Lys Val Val Ile Glu Ala
450                 455                 460
Arg Gly Leu Leu Arg Arg Phe Ala Asp Ser Leu Lys Ser Ala Val Glu
465                 470                 475                 480
Gly Leu Gly Asp Cys Val Tyr Asp Ala Leu Val Gln Thr Gly Trp Phe
                485                 490                 495
Asp Thr Ser Ser Asp Glu Leu Lys Val Leu Leu Pro Glu Pro Phe Met
            500                 505                 510
Thr Phe Ser Asp Tyr Leu Glu Gly Met Tyr Glu Ala Asp Ala Lys Ile
            515                 520                 525
Glu Arg Glu Ser Val Ser Glu Leu Leu Ala Ser Gly Asp Asp Leu Phe
        530                 535                 540
Lys Lys Ile Asp Glu Ile Arg Asn Asn Tyr Ser Gly Val Glu Phe Asp
545                 550                 555                 560
Val Glu Lys Phe Gln Glu Phe Cys Lys Glu Leu Asn Val Asn Pro Met
                565                 570                 575
Leu Ile Gly His Val Ile Glu Ala Ile Phe Ser Gln Lys Ala Gly Val
            580                 585                 590
Thr Val Thr Gly Leu Gly Thr Leu Ser Pro Glu Met Gly Ala Ser Val
            595                 600                 605
Ala Leu Ser Asn Asn Ser Val Asp Thr Cys Asp Asp Met Asp Val Thr
        610                 615                 620
Glu Asp Met Glu Glu Ile Val Leu Ile Ala Asp Lys Asn His Ser Tyr
625                 630                 635                 640
Ile Ser Pro Glu Met Ser Arg Trp Ala Ser Met Lys Tyr Gly Asn Asn
                645                 650                 655
Asn Gly Ala Leu Val Glu Tyr Lys Val Gly Thr Ser Met Thr Leu Pro
            660                 665                 670
Ala Thr Trp Ala Glu Lys Gly Lys Ala Val Leu Pro Leu Ser Gly Ile
            675                 680                 685
Cys Val Arg Lys Pro Gln Phe Ser Lys Pro Leu Asp Glu Glu Asp Asp
        690                 695                 700
Leu Arg Leu Ser Asn Met Asn Phe Phe Lys Val Ser Asp Leu Lys Leu
705                 710                 715                 720
Lys Lys Thr Ile Thr Pro Val Val Tyr Thr Gly Thr Ile Arg Glu Arg
                725                 730                 735
Gln Met Lys Asn Tyr Ile Asp Tyr Leu Ser Ala Ser Leu Gly Ser Thr
            740                 745                 750
Leu Gly Asn Leu Glu Arg Ile Val Arg Ser Asp Trp Asn Gly Thr Glu
            755                 760                 765
Glu Ser Met Gln Thr Phe Gly Leu Tyr Asp Cys Glu Lys Cys Lys Trp
        770                 775                 780
Leu Leu Leu Pro Ser Glu Lys Lys His Ala Trp Ala Val Val Leu Ala
785                 790                 795                 800
Ser Asp Asp Thr Thr Arg Ile Ile Phe Leu Ser Tyr Asp Glu Ser Gly
                805                 810                 815
Ser Pro Ile Ile Asp Lys Lys Asn Trp Lys Arg Phe Ala Val Cys Ser
            820                 825                 830
Asp Thr Lys Val Tyr Ser Val Ile Arg Ser Leu Glu Val Leu Asn Lys
            835                 840                 845
Glu Ala Thr Val Asp Pro Gly Val Tyr Ile Thr Leu Val Asp Gly Val
        850                 855                 860
```

-continued

Pro Gly Cys Gly Lys Thr Ala Glu Ile Ile Ala Arg Val Asn Trp Lys
865                 870                 875                 880

Thr Asp Leu Val Leu Thr Pro Gly Arg Glu Ala Ala Met Ile Arg
            885                 890                 895

Arg Arg Ala Cys Ala Leu His Lys Ser Pro Val Ala Thr Ser Asp Asn
            900                 905                 910

Val Arg Thr Phe Asp Ser Phe Val Met Asn Lys Val Phe Lys Phe
        915                 920                 925

Asp Ala Val Tyr Val Asp Glu Gly Leu Met Val His Thr Gly Leu Leu
        930                 935                 940

Asn Phe Ala Leu Lys Ile Ser Gly Cys Lys Lys Ala Phe Val Phe Gly
945                 950                 955                 960

Asp Ala Lys Gln Ile Pro Phe Ile Asn Arg Val Met Asn Phe Asp Tyr
                965                 970                 975

Pro Lys Glu Leu Arg Thr Leu Ile Val Asp Asn Val Glu Arg Arg Tyr
            980                 985                 990

Ile Thr His Arg Cys Pro Arg Asp Val Thr Ser Phe Leu Asn Thr Ile
        995                 1000                1005

Tyr Lys Ala Ala Val Ser Thr Thr Ser Pro Val Val His Ser Val Lys
    1010                1015                1020

Ala Ile Lys Val Ser Gly Ala Gly Ile Leu Arg Pro Glu Leu Thr Lys
1025                1030                1035                1040

Ile Lys Gly Lys Ile Ile Thr Phe Thr Gln Ser Asp Lys Gln Ser Leu
                1045                1050                1055

Ile Lys Ser Gly Tyr Asn Asp Val Asn Thr Val His Glu Ile Gln Gly
            1060                1065                1070

Glu Thr Phe Glu Glu Thr Ala Val Val Arg Ala Thr Pro Thr Pro Ile
        1075                1080                1085

Gly Leu Ile Ala Arg Asp Ser Pro His Val Leu Val Ala Leu Thr Arg
    1090                1095                1100

His Thr Lys Ala Met Val Tyr Tyr Thr Val Val Phe Asp Ala Val Thr
1105                1110                1115                1120

Ser Ile Ile Ala Asp Val Glu Lys Val Asp Gln Ser Ile Leu Thr Met
                1125                1130                1135

Phe Ala Thr Thr Val Pro Thr Lys
            1140

<210> SEQ ID NO 3
<211> LENGTH: 1503
<212> TYPE: DNA
<213> ORGANISM: Cucumber green mottle mosaic virus
<220> FEATURE:
<223> OTHER INFORMATION: DNA sequence encoding 57 kD protein of CGMMV

<400> SEQUENCE: 3
atggagaatt cgctgtatgt ccaccgcaat atcttcctcc ctgttactaa gacagggttt     60
tatacggata tgcaggagtt ctatgacagg tgtcttccag ggaattcttt tgttctgaac    120
gatttcgatg ccgtcaccat gcggttgagg gataatgaat tcaatttgca accttgtaga    180
ttaactttaa gtaatttaga tccggtgccg gctttgatta agagtgaggc aaaagatttt    240
ctggttcccg tattgcgaac ggcttgcgaa aggccgcgta ttccgggtct tctcgaaaat    300
cttgttgcta tgataaagag gaatatgaat actcctgatt ggctgggac cgtggatata    360 actaatatgt ctatttctat agtagataat ttcttttctt cctttgtcag ggacgaggtt    420

```
ctacttgatc atttagattg cgttagagct agttctattc agagttttc cgattggttt      480
tcttgtcagc caacctcggc ggttggccag ttagctaatt taacttcat agatttacct      540
gcctttgata cgtatatgca tatgattaaa aggcagccta agagtcggtt agatacttcg      600
attcagtccg aatatccggc cttacaaact attgtatatc atccgaaggt ggtaaacgca      660
gttttcgggc cggtttttaa gtatctgact actaagtttc ttagcatggt agataattct      720
aagttttcct tttatactag gaaaaagcca gaggatctgc aggaattttt ctcggatctt      780
tcttcccatt ctgattatga aattcttgag ctcgatgttt ctaaatatga taagtcgcag      840
tccgatttcc atttctctat cgagatggca atttgggaaa ggctgggact agatgatatt      900
ttagcttgga tgtggtctat gggtcataag agaactatac tgcaagattt ccaagctgga      960
ataaagacgc tcattatta tcaaaggaag tctggcgacg taactacttt cataggtaat    1020
acttttatta ttgcagcgtg tgtagctagt atgttaccgt tagataagtg ttttaaggct    1080
agttttgtg gtgatgattc gttaatctac cttcctaagg gtttggagta tcctgatatt    1140
caggctactg ccaatttggt ttggaatttt gaggcgaaac ttttccggaa gaagtatggt    1200
tacttctgcg ggaaatatat cattcatcac gccaacggtt gtattgttta ccctgacccct    1260
ttgaagttaa ttagtaaatt aggtagtaag agtcttgtag ggtacgagca tgtcgaggag    1320
tttcgtatat ctctcctcga tgtcgctcac agtttgttta atggtgctta tttccatttg    1380
ctcgacgatg caatccacga gttgtttcct aacgctgggg gttgcagttt tgtaataaat    1440
tgtttgtgta agtacttgag tgataagcgc cttttccgta gtctttatat agatgtctct    1500
aag                                                                 1503

<210> SEQ ID NO 4
<211> LENGTH: 501
<212> TYPE: PRT
<213> ORGANISM: Cucumber green mottle mosaic virus
<220> FEATURE:
<223> OTHER INFORMATION: 57 kD protein of CGMMV

<400> SEQUENCE: 4

Met Glu Asn Ser Leu Tyr Val His Arg Asn Ile Phe Leu Pro Val Thr
  1               5                  10                  15

Lys Thr Gly Phe Tyr Thr Asp Met Gln Glu Phe Tyr Asp Arg Cys Leu
             20                  25                  30

Pro Gly Asn Ser Phe Val Leu Asn Asp Phe Asp Ala Val Thr Met Arg
         35                  40                  45

Leu Arg Asp Asn Glu Phe Asn Leu Gln Pro Cys Arg Leu Thr Leu Ser
     50                  55                  60

Asn Leu Asp Pro Val Pro Ala Leu Ile Lys Ser Glu Ala Lys Asp Phe
 65                  70                  75                  80

Leu Val Pro Val Leu Arg Thr Ala Cys Glu Arg Pro Arg Ile Pro Gly
                 85                  90                  95

Leu Leu Glu Asn Leu Val Ala Met Ile Lys Arg Asn Met Asn Thr Pro
            100                 105                 110

Asp Leu Ala Gly Thr Val Asp Ile Thr Asn Met Ser Ile Ser Ile Val
        115                 120                 125

Asp Asn Phe Phe Ser Ser Phe Val Arg Asp Glu Val Leu Leu Asp His
    130                 135                 140

Leu Asp Cys Val Arg Ala Ser Ser Ile Gln Ser Phe Ser Asp Trp Phe
145                 150                 155                 160

Ser Cys Gln Pro Thr Ser Ala Val Gly Gln Leu Ala Asn Phe Asn Phe
```

```
                    165                 170                 175
Ile Asp Leu Pro Ala Phe Asp Thr Tyr Met His Met Ile Lys Arg Gln
                180                 185                 190
Pro Lys Ser Arg Leu Asp Thr Ser Ile Gln Ser Glu Tyr Pro Ala Leu
            195                 200                 205
Gln Thr Ile Val Tyr His Pro Lys Val Val Asn Ala Val Phe Gly Pro
        210                 215                 220
Val Phe Lys Tyr Leu Thr Thr Lys Phe Leu Ser Met Val Asp Asn Ser
225                 230                 235                 240
Lys Phe Phe Tyr Thr Arg Lys Lys Pro Glu Asp Leu Gln Glu Phe
                245                 250                 255
Phe Ser Asp Leu Ser Ser His Ser Asp Tyr Glu Ile Leu Glu Leu Asp
                260                 265                 270
Val Ser Lys Tyr Asp Lys Ser Gln Ser Asp Phe His Phe Ser Ile Glu
            275                 280                 285
Met Ala Ile Trp Glu Arg Leu Gly Leu Asp Asp Ile Leu Ala Trp Met
        290                 295                 300
Trp Ser Met Gly His Lys Arg Thr Ile Leu Gln Asp Phe Gln Ala Gly
305                 310                 315                 320
Ile Lys Thr Leu Ile Tyr Tyr Gln Arg Lys Ser Gly Asp Val Thr Thr
                325                 330                 335
Phe Ile Gly Asn Thr Phe Ile Ile Ala Ala Cys Val Ala Ser Met Leu
            340                 345                 350
Pro Leu Asp Lys Cys Phe Lys Ala Ser Phe Cys Gly Asp Asp Ser Leu
        355                 360                 365
Ile Tyr Leu Pro Lys Gly Leu Glu Tyr Pro Asp Ile Gln Ala Thr Ala
        370                 375                 380
Asn Leu Val Trp Asn Phe Glu Ala Lys Leu Phe Arg Lys Lys Tyr Gly
385                 390                 395                 400
Tyr Phe Cys Gly Lys Tyr Ile Ile His His Ala Asn Gly Cys Ile Val
                405                 410                 415
Tyr Pro Asp Pro Leu Lys Leu Ile Ser Lys Leu Gly Ser Lys Ser Leu
            420                 425                 430
Val Gly Tyr Glu His Val Glu Glu Phe Arg Ile Ser Leu Leu Asp Val
        435                 440                 445
Ala His Ser Leu Phe Asn Gly Ala Tyr Phe His Leu Leu Asp Asp Ala
    450                 455                 460
Ile His Glu Leu Phe Pro Asn Ala Gly Gly Cys Ser Phe Val Ile Asn
465                 470                 475                 480
Cys Leu Cys Lys Tyr Leu Ser Asp Lys Arg Leu Phe Arg Ser Leu Tyr
                485                 490                 495
Ile Asp Val Ser Lys
            500

<210> SEQ ID NO 5
<211> LENGTH: 4935
<212> TYPE: DNA
<213> ORGANISM: Cucumber green mottle mosaic virus
<220> FEATURE:
<223> OTHER INFORMATION: DNA sequence encoding 186 kDa protein of CGMMV

<400> SEQUENCE: 5
atggcaaaca ttaatgaaca aatcaacaat caacgtgatg ctgctgctag cgggagaaat      60
aatctcgtta gtcagctagc atcaaagagg gtgtatgacg aggccgttcg ctcgttagat     120
```

```
catcaagata gacgcccaaa aatgaacttt tctcgtgtgg tcagtacaga gcacaccagg    180
cttgtcaccg atgcgtatcc ggagttttcg attagtttca ccgctaccaa gaattcagtt    240
cattcccttg cgggaggttt gaggcttctt gaattggaat acatgatgat gcaggtgcct    300
tatggttcac cttgctttga tattggcggt aattacacgc agcatttatt taaaggtaga    360
tcatatgtgc attgctgcaa tccgtgcctg gatcttaagg atgttgcgag gaatgtgatg    420
tacaacgaca tgatcacaca acatgtacag aggcacaaag gatctggtgg gtgtagacct    480
cttccgactt tccagataga tgctttcagg aggtatgaag attcgcccgt cgcagtcacc    540
tgtccagacg ttttcaaga atgctcctat gattttggga gtggtaggga taatcatgcg    600
gtttcattac attcgattta tgatatccct tattcttcga ttgggccagc tcttcatagg    660
aaaaacgtca gggtctgtta cgcagccttt catttctcgg aggcgttgct cctaggttcg    720
cccgtgggta atttaaatag tataggggct caatttaggg ttgatggtga cgatgtgcat    780
tttctttta gtgaggagtc aactttgcat tacactcata gtttggagaa tattaagttg    840
attgtaatgc gtacttattt ccctgctgat gataggttcg tgtatattaa ggagtttatg    900
gttaagcgtg tagacacttt tttttttagg ttagttaggg cagacacaca tatgctccat    960
aaatctgtag ggcactattc gaagtcgaaa tctgagtatt ttgcgttgaa cacccctccg   1020
attttccaag ataaggccac gttttctgtg tggtttcccg aagcgaagcg gaaggtgttg   1080
atacctaagt ttgaactctc gagatttctt tctggaaatg tgaaagtctc taggatgctt   1140
gtcgatgctg attttgtcca taccattatt aatcacatta gcacgtacga taacaaggcc   1200
ttagtgtgga agaatgtcca gtcttttgta gaatctatac gctctagggt aattgtaaac   1260
ggagtttccg taaaatctga atggaatgta ccggtcgatc agcttactga tatctcattc   1320
tcgatattcc ttctcgtgaa ggttagaaag gtgcagattg agttaatgtc tgataaggtt   1380
gtgatcgagg cgaggggttt gcttcggagg ttcgctgata gtctcaaatc cgccgtagaa   1440
ggactaggtg attgcgtcta tgatgctcta gttcaaaccg gttggtttga cacctctagc   1500
gacgaactga agtgtattact acctgaaccg tttatgacct tttcagatta tctcgaaggg   1560
atgtacgagg cagatgcaaa aattgagaga gagagtgtct ctgagctgct tgcttccgga   1620
gatgatctgt tcaagaagat tgacgaaata aggaataatt acagcggagt tgaatttgat   1680
gtggagaaat ttcaagaatt ctgtaaagaa ctgaatgtta atcctatgct aatcggtcat   1740
gtgatcgaag ctattttttc acagaaggca ggggtaacag tcacgggcct aggcacgctc   1800
tctcctgaga tgggtgcttc cgttgcgtta tccaataatt ctgtagatac atgtgatgat   1860
atggacgtaa ctgaggatat ggaggaaata gtgttgatag cagacaagaa tcactcttat   1920
atttctccag aaatgtcgag atgggctagt atgaaatacg gcaataataa cggggcctta   1980
gttgagtaca aggtcggaac ctcgatgact ttacctgcca cctgggcaga aaagggtaag   2040
gctgttttac cgttgtcggg aatctgtgta agaaagcccc aatttcaaa gccactcgat   2100
gaggaggacg acttgaggtt atcaaacatg aatttctttta aggtgagtga tctgaagttg   2160
aagaagacta tcactccagt tgtttatact gggaccattc gagagaggca gatgaagaat   2220
tatatcgatt atctatcggc ttctctgggt tctacgcttg taatcttga gagaattgtt   2280
aggagtgact ggaatggtac cgaggagagc atgcaaactt ttggattgta cgattgcgag   2340
aagtgcaagt ggttactgtt gccatcggag aagaaacacg cctgggctgt agtcctggcg   2400
agtgatgata ccactcgtat aatctttctg tcgtatgacg aatccggttc tcctataatt   2460
gacaagaaaa attggaagcg gttcgctgtc tgttctgata ccaaagttta tagtgtaatt   2520
```

```
cgtagtttag aagtcttaaa taaggaggcc acagtcgatc ctggggtgta tataacttta    2580
gtcgatgggg ttccgggctg tggaaaaacc gctgaaatta tagcgagggt caattggaaa    2640
actgaccttg tgttgactcc cggaagggaa gcggctgcta tgatcaggcg aagagcctgt    2700
gccctacaca agtcacctgt agctactagt gataacgtta ggacttttga ttctttcgta    2760
atgaataaga aggttttaa atttgacgcc gtctacgtag atgaaggtct tatggtccac    2820
acggggttgc tcaactttgc gttgaagatt tcggttgta aaaaggcctt tgtcttcggt    2880
gatgctaagc aaaattccgtt tattaataga gttatgaatt ttgattatcc taaggaatta    2940
agaactttga tagttgataa tgtagagcgt aggtatatta cccataggtg tcctagagat    3000
gtcactagtt ttcttaatac tatttataaa gctgcggttt ctaccactag tccggttgta    3060
cattccgtga aggcaataaa ggtttctggg gctggtattc tgaggcccga gttgacgaag    3120
atcaaaggga agatcataac gtttactcag tctgataaac aatccttgat caagagtggg    3180
tacaatgatg tgaatactgt gcatgagatt caggggagaa cctttgagga gacggcggtt    3240
gtgcgtgcaa caccgactcc aataggtctg attgcccgag attcaccaca cgtgttagtg    3300
gctttaacgc ggcacaccaa ggcaatggtg tattataccg ttgtgttcga tgccgtaaca    3360
agcataatag cggatgtgga aaaggtcgat cagtcgattt tgactatgtt tgctactact    3420
gtgcctacca aaatggagaa ttcgctgtat gtccaccgca atatcttcct ccctgttact    3480
aagacagggt tttatacgga tatgcaggag ttctatgaca ggtgtcttcc agggaattct    3540
tttgttctga acgatttcga tgccgtcacc atgcggttga gggataatga attcaattg    3600
caaccttgta gattaacttt aagtaattta gatccggtgc cggctttgat taagagtgag    3660
gcaaagatt ttctggttcc cgtattgcga acggcttgcg aaaggccgcg tattccgggt    3720
cttctcgaaa atcttgttgc tatgataaag aggaatatga atactcctga tttggctggg    3780
accgtggata taactaatat gtctatttct atagtgataa atttctttc ttcctttgtc    3840
agggacgagg ttctacttga tcatttagat tgcgttagag ctagttctat tcagagtttt    3900
tccgattggt tttcttgtca gccaacctcg gcggttggcc agttagctaa ttttaacttc    3960
atagatttac ctgcctttga tacgtatatg catatgatta aaaggcagcc taagagtcgg    4020
ttagatactt cgattcagtc cgaatatccg gccttacaaa ctattgtata tcatccgaag    4080
gtggtaaacg cagttttcgg gccggttttt aagtatctga ctactaagtt tcttagcatg    4140
gtagataatt ctaagttttt cttttatact aggaaaaagc cagaggatct gcaggaattt    4200
ttctcggatc tttcttccca ttctgattat gaaattcttg agctcgatgt ttctaaatat    4260
gataagtcgc agtccgattt ccatttctct atcgagatgg caatttggga aaggctggga    4320
ctagatgata ttttagcttg gatgtggtct atgggtcata agagaactat actgcaagat    4380
ttccaagctg gaataaagac gctcatttat tatcaaagga agtctggcga cgtaactact    4440
ttcataggta atacttttat tattgcagcg tgtgtagcta gtatgttacc gttagataag    4500
tgttttaagg ctagttttttg tggtgatgat tcgttaatct accttcctaa gggtttggag    4560
tatcctgata ttcaggctac tgccaatttg gtttggaatt ttgaggcgaa acttttccgg    4620
aagaagtatg gttacttctg cgggaaatat atcattcatc acgccaacgg ttgtattgtt    4680
taccctgacc ctttgaagtt aattagtaaa ttaggtagta agagtcttgt agggtacgag    4740
catgtcgagg agtttcgtat atctctcctc gatgtcgctc acagtttgtt taatggtgct    4800
tatttccatt tgctcgacga tgcaatccac gagttgtttc ctaacgctgg gggttgcagt    4860
```

-continued

```
tttgtaataa attgtttgtg taagtacttg agtgataagc gccttttccg tagtctttat    4920
atagatgtct ctaag                                                    4935
```

<210> SEQ ID NO 6
<211> LENGTH: 1645
<212> TYPE: PRT
<213> ORGANISM: Cucumber green mottle mosaic virus
<220> FEATURE:
<223> OTHER INFORMATION: 186 kD protein of CGMMV

<400> SEQUENCE: 6

```
Met Ala Asn Ile Asn Glu Gln Ile Asn Asn Gln Arg Asp Ala Ala Ala
 1               5                  10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Gly Leu Arg Leu Leu Glu Leu Glu Tyr Met Met
                85                  90                  95

Met Gln Val Pro Tyr Gly Ser Pro Cys Phe Asp Ile Gly Gly Asn Tyr
           100                 105                 110

Thr Gln His Leu Phe Lys Gly Arg Ser Tyr Val His Cys Cys Asn Pro
       115                 120                 125

Cys Leu Asp Leu Lys Asp Val Ala Arg Asn Val Met Tyr Asn Asp Met
   130                 135                 140

Ile Thr Gln His Val Gln Arg His Lys Gly Ser Gly Gly Cys Arg Pro
145                 150                 155                 160

Leu Pro Thr Phe Gln Ile Asp Ala Phe Arg Arg Tyr Glu Asp Ser Pro
               165                 170                 175

Val Ala Val Thr Cys Pro Asp Val Phe Gln Glu Cys Ser Tyr Asp Phe
           180                 185                 190

Gly Ser Gly Arg Asp Asn His Ala Val Ser Leu His Ser Ile Tyr Asp
       195                 200                 205

Ile Pro Tyr Ser Ser Ile Gly Pro Ala Leu His Arg Lys Asn Val Arg
   210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
               245                 250                 255

Asp Asp Val His Phe Leu Phe Ser Glu Ser Thr Leu His Tyr Thr
           260                 265                 270

His Ser Leu Glu Asn Ile Lys Leu Ile Val Met Arg Thr Tyr Phe Pro
       275                 280                 285

Ala Asp Asp Arg Phe Val Tyr Ile Lys Glu Phe Met Val Lys Arg Val
   290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
               325                 330                 335

Asn Thr Pro Pro Ile Phe Gln Asp Lys Ala Thr Phe Ser Val Trp Phe
           340                 345                 350
```

-continued

```
Pro Glu Ala Lys Arg Lys Val Leu Ile Pro Lys Phe Glu Leu Ser Arg
        355                 360                 365

Phe Leu Ser Gly Asn Val Lys Val Ser Arg Met Leu Val Asp Ala Asp
        370                 375                 380

Phe Val His Thr Ile Ile Asn His Ile Ser Thr Tyr Asp Asn Lys Ala
385                 390                 395                 400

Leu Val Trp Lys Asn Val Gln Ser Phe Val Glu Ser Ile Arg Ser Arg
                405                 410                 415

Val Ile Val Asn Gly Val Ser Val Lys Ser Glu Trp Asn Val Pro Val
                420                 425                 430

Asp Gln Leu Thr Asp Ile Ser Phe Ser Ile Phe Leu Leu Val Lys Val
        435                 440                 445

Arg Lys Val Gln Ile Glu Leu Met Ser Asp Lys Val Ile Glu Ala
        450                 455                 460

Arg Gly Leu Leu Arg Arg Phe Ala Asp Ser Leu Lys Ser Ala Val Glu
465                 470                 475                 480

Gly Leu Gly Asp Cys Val Tyr Asp Ala Leu Val Gln Thr Gly Trp Phe
                485                 490                 495

Asp Thr Ser Ser Asp Glu Leu Lys Val Leu Leu Pro Glu Pro Phe Met
        500                 505                 510

Thr Phe Ser Asp Tyr Leu Glu Gly Met Tyr Glu Ala Asp Ala Lys Ile
        515                 520                 525

Glu Arg Glu Ser Val Ser Glu Leu Leu Ala Ser Gly Asp Asp Leu Phe
        530                 535                 540

Lys Lys Ile Asp Glu Ile Arg Asn Asn Tyr Ser Gly Val Glu Phe Asp
545                 550                 555                 560

Val Glu Lys Phe Gln Glu Phe Cys Lys Glu Leu Asn Val Asn Pro Met
                565                 570                 575

Leu Ile Gly His Val Ile Glu Ala Ile Phe Ser Gln Lys Ala Gly Val
                580                 585                 590

Thr Val Thr Gly Leu Gly Thr Leu Ser Pro Glu Met Gly Ala Ser Val
        595                 600                 605

Ala Leu Ser Asn Asn Ser Val Asp Thr Cys Asp Asp Met Asp Val Thr
        610                 615                 620

Glu Asp Met Glu Glu Ile Val Leu Ile Ala Asp Lys Asn His Ser Tyr
625                 630                 635                 640

Ile Ser Pro Glu Met Ser Arg Trp Ala Ser Met Lys Tyr Gly Asn Asn
                645                 650                 655

Asn Gly Ala Leu Val Glu Tyr Lys Val Gly Thr Ser Met Thr Leu Pro
        660                 665                 670

Ala Thr Trp Ala Glu Lys Gly Lys Ala Val Leu Pro Leu Ser Gly Ile
        675                 680                 685

Cys Val Arg Lys Pro Gln Phe Ser Lys Pro Leu Asp Glu Glu Asp Asp
        690                 695                 700

Leu Arg Leu Ser Asn Met Asn Phe Phe Lys Val Ser Asp Leu Lys Leu
705                 710                 715                 720

Lys Lys Thr Ile Thr Pro Val Val Tyr Thr Gly Thr Ile Arg Glu Arg
                725                 730                 735

Gln Met Lys Asn Tyr Ile Asp Tyr Leu Ser Ala Ser Leu Gly Ser Thr
                740                 745                 750

Leu Gly Asn Leu Glu Arg Ile Val Arg Ser Asp Trp Asn Gly Thr Glu
        755                 760                 765
```

-continued

```
Glu Ser Met Gln Thr Phe Gly Leu Tyr Asp Cys Glu Lys Cys Lys Trp
    770                 775                 780
Leu Leu Leu Pro Ser Glu Lys Lys His Ala Trp Ala Val Val Leu Ala
785                 790                 795                 800
Ser Asp Asp Thr Thr Arg Ile Ile Phe Leu Ser Tyr Asp Glu Ser Gly
                805                 810                 815
Ser Pro Ile Ile Asp Lys Lys Asn Trp Lys Arg Phe Ala Val Cys Ser
                820                 825                 830
Asp Thr Lys Val Tyr Ser Val Ile Arg Ser Leu Glu Val Leu Asn Lys
                835                 840                 845
Glu Ala Thr Val Asp Pro Gly Val Tyr Ile Thr Leu Val Asp Gly Val
    850                 855                 860
Pro Gly Cys Gly Lys Thr Ala Glu Ile Ile Ala Arg Val Asn Trp Lys
865                 870                 875                 880
Thr Asp Leu Val Leu Thr Pro Gly Arg Glu Ala Ala Met Ile Arg
                885                 890                 895
Arg Arg Ala Cys Ala Leu His Lys Ser Pro Val Ala Thr Ser Asp Asn
                900                 905                 910
Val Arg Thr Phe Asp Ser Phe Val Met Asn Lys Lys Val Phe Lys Phe
                915                 920                 925
Asp Ala Val Tyr Val Asp Glu Gly Leu Met Val His Thr Gly Leu Leu
                930                 935                 940
Asn Phe Ala Leu Lys Ile Ser Gly Cys Lys Lys Ala Phe Val Phe Gly
945                 950                 955                 960
Asp Ala Lys Gln Ile Pro Phe Ile Asn Arg Val Met Asn Phe Asp Tyr
                965                 970                 975
Pro Lys Glu Leu Arg Thr Leu Ile Val Asp Asn Val Glu Arg Arg Tyr
                980                 985                 990
Ile Thr His Arg Cys Pro Arg Asp Val Thr Ser Phe Leu Asn Thr Ile
                995                 1000                1005
Tyr Lys Ala Ala Val Ser Thr Thr Ser Pro Val Val His Ser Val Lys
                1010                1015                1020
Ala Ile Lys Val Ser Gly Ala Gly Ile Leu Arg Pro Glu Leu Thr Lys
1025                1030                1035                1040
Ile Lys Gly Lys Ile Ile Thr Phe Thr Gln Ser Asp Lys Gln Ser Leu
                1045                1050                1055
Ile Lys Ser Gly Tyr Asn Asp Val Asn Thr Val His Glu Ile Gln Gly
                1060                1065                1070
Glu Thr Phe Glu Glu Thr Ala Val Val Arg Ala Thr Pro Thr Pro Ile
                1075                1080                1085
Gly Leu Ile Ala Arg Asp Ser Pro His Val Leu Val Ala Leu Thr Arg
                1090                1095                1100
His Thr Lys Ala Met Val Tyr Tyr Thr Val Val Phe Asp Ala Val Thr
1105                1110                1115                1120
Ser Ile Ile Ala Asp Val Glu Lys Val Asp Gln Ser Ile Leu Thr Met
                1125                1130                1135
Phe Ala Thr Thr Val Pro Thr Lys Met Glu Asn Ser Leu Tyr Val His
                1140                1145                1150
Arg Asn Ile Phe Leu Pro Val Thr Lys Thr Gly Phe Tyr Thr Asp Met
                1155                1160                1165
Gln Glu Phe Tyr Asp Arg Cys Leu Pro Gly Asn Ser Phe Val Leu Asn
                1170                1175                1180
Asp Phe Asp Ala Val Thr Met Arg Leu Arg Asp Asn Glu Phe Asn Leu
```

-continued

```
     1185                1190                1195                1200

Gln Pro Cys Arg Leu Thr Leu Ser Asn Leu Asp Pro Val Pro Ala Leu
             1205                1210                1215

Ile Lys Ser Glu Ala Lys Asp Phe Leu Val Pro Val Leu Arg Thr Ala
     1220                1225                1230

Cys Glu Arg Pro Arg Ile Pro Gly Leu Leu Glu Asn Leu Val Ala Met
             1235                1240                1245

Ile Lys Arg Asn Met Asn Thr Pro Asp Leu Ala Gly Thr Val Asp Ile
     1250                1255                1260

Thr Asn Met Ser Ile Ser Ile Val Asp Asn Phe Phe Ser Phe Ser Val
1265                1270                1275                1280

Arg Asp Glu Val Leu Leu Asp His Leu Asp Cys Val Arg Ala Ser Ser
             1285                1290                1295

Ile Gln Ser Phe Ser Asp Trp Phe Ser Cys Gln Pro Thr Ser Ala Val
     1300                1305                1310

Gly Gln Leu Ala Asn Phe Asn Phe Ile Asp Leu Pro Ala Phe Asp Thr
             1315                1320                1325

Tyr Met His Met Ile Lys Arg Gln Pro Lys Ser Arg Leu Asp Thr Ser
     1330                1335                1340

Ile Gln Ser Glu Tyr Pro Ala Leu Gln Thr Ile Val Tyr His Pro Lys
1345                1350                1355                1360

Val Val Asn Ala Val Phe Gly Pro Val Phe Lys Tyr Leu Thr Thr Lys
             1365                1370                1375

Phe Leu Ser Met Val Asp Asn Ser Lys Phe Phe Phe Tyr Thr Arg Lys
     1380                1385                1390

Lys Pro Glu Asp Leu Gln Glu Phe Phe Ser Asp Leu Ser Ser His Ser
             1395                1400                1405

Asp Tyr Glu Ile Leu Glu Leu Asp Val Ser Lys Tyr Asp Lys Ser Gln
     1410                1415                1420

Ser Asp Phe His Phe Ser Ile Glu Met Ala Ile Trp Glu Arg Leu Gly
1425                1430                1435                1440

Leu Asp Asp Ile Leu Ala Trp Met Trp Ser Met Gly His Lys Arg Thr
             1445                1450                1455

Ile Leu Gln Asp Phe Gln Ala Gly Ile Lys Thr Leu Ile Tyr Tyr Gln
     1460                1465                1470

Arg Lys Ser Gly Asp Val Thr Thr Phe Ile Gly Asn Thr Phe Ile Ile
             1475                1480                1485

Ala Ala Cys Val Ala Ser Met Leu Pro Leu Asp Lys Cys Phe Lys Ala
     1490                1495                1500

Ser Phe Cys Gly Asp Asp Ser Leu Ile Tyr Leu Pro Lys Gly Leu Glu
1505                1510                1515                1520

Tyr Pro Asp Ile Gln Ala Thr Ala Asn Leu Val Trp Asn Phe Glu Ala
             1525                1530                1535

Lys Leu Phe Arg Lys Lys Tyr Gly Tyr Phe Cys Gly Lys Tyr Ile Ile
     1540                1545                1550

His His Ala Asn Gly Cys Ile Val Tyr Pro Asp Pro Leu Lys Leu Ile
             1555                1560                1565

Ser Lys Leu Gly Ser Lys Ser Leu Val Gly Tyr Glu His Val Glu Glu
     1570                1575                1580

Phe Arg Ile Ser Leu Leu Asp Val Ala His Ser Leu Phe Asn Gly Ala
1585                1590                1595                1600

Tyr Phe His Leu Leu Asp Asp Ala Ile His Glu Leu Phe Pro Asn Ala
             1605                1610                1615
```

-continued

Gly Gly Cys Ser Phe Val Ile Asn Cys Leu Cys Lys Tyr Leu Ser Asp
    1620                1625                1630

Lys Arg Leu Phe Arg Ser Leu Tyr Ile Asp Val Ser Lys
        1635                1640            1645

<210> SEQ ID NO 7
<211> LENGTH: 1139
<212> TYPE: DNA
<213> ORGANISM: Cucumber green mottle mosaic virus
<220> FEATURE:
<223> OTHER INFORMATION: DNA sequence encoding coat protein of CGMMV
      isolate 1

<400> SEQUENCE: 7
aattcggctt ctgtaggggt ggtgctactg ttgctttggt tgacacaagg atgcattctg    60
ttgcagaagg aactatatgc aaattttcag ctcccgccac cgtccgcgag ttctctgtta   120
ggttcatccc taactattct gtcgtggttg cggatgccct tcgcgatcct tggtctttat   180
ttgtgaggct ctctaacgta ggtattaagg atggtttttca tccattaact ttagaggtcg   240
cctgtctagt tgccactact aactctatta ttaaaaaggg gcttagagct tctgtagttg   300
agtccgttgt ctcttccgat cagtcgattg ttctagattc tttatctgag aaagttgagc   360
cttttcttcga taaagtccct atttcagcgg ctgtaatggc gagagacccc agttataggt   420
ctaggtcgca gtctgtcgtt ggtcgtggta agcggcattc taaacctcca aatcggaggt   480
cggactctgc ttctgaagag tccagttctg tttctttcga agatggctta caatccgatc   540
acgcctagca aacttattgc gtttagtgct tcttatgctc ccgttagaac tttacttaat   600
tttctagtgg cgtcgcaagg tactgctttc caaacccagg caggaagaga ttccttccgt   660
gagtctttgt ctgcgttacc ttcatccgtt gtagatatta attctaggtt cccgagtgcg   720
ggtttttacg ccttcctcaa cggtcctgtg ttgaggccta tcttcgtttc gcttcttagc   780
tctacggata cgcgtaatag ggtcattgag gttgtagatc ctagcaatcc gacgactgct   840
gaatcgctta acgcagttaa gcgtactgac gatgcgtcta cagccgctag gctgagata    900
gataattttaa tagaatcaat ctctaagggg tttgatgttt atgatagggc ttcttttgaa   960
gccgcgtttt cggtagtctg tcagagggct accacctcca aggcttagcc ttgagggtct  1020
tctgacggtg gtgcacacca tagtgcatag tgctttcccg ttcactttaa tcgaacggtt  1080
tgctcattgg tttgcgaaaa cctctcgcgt gtgacgttga agtttctatg ggcaagccg   1139

<210> SEQ ID NO 8
<211> LENGTH: 1139
<212> TYPE: DNA
<213> ORGANISM: Cucumber green mottle mosaic virus
<220> FEATURE:
<223> OTHER INFORMATION: DNA sequence encoding coat protein of CGMMV
      isolate 2

<400> SEQUENCE: 8
aattcggctt ctgtaggggt ggtgctactg ttgctttggt tgacacaagg atgcattctg    60
ttgcagaagg aactatatgc aaattttcag ctcccgccac cgtccgcgag ttctctgtta   120
ggttcatccc taactattct gtcgtggttg cggatgccct tcgcgatcct tggtctttat   180
ttgtgaggct ctctaacgta ggtattaagg atggtttttca tccattaact ttagaggtcg   240
cctgtctagt tgccactact aactctatta ttaaaaaggg gcttagagct tctgtagttg   300
agtccgttgt ctcttccgat cagtcgattg ttctagattc tttatctgag aaagttgagc   360

```
ctttcttcga taaagtccct atttcagcgg ctgtaatggc gagagacccc agttataggt    420
ctaggtcgca gtctgtcgtt ggtcgtggta agcggcattc taaacctcca aatcggaggt    480
cggactctgc ttctgaagag tccagttctg tttctttcga agatggctta caatccgatc    540
acgcctagca aacttattgc gtttagtgct tcttatgctc ccgttagaac tttacttaat    600
tttctagtgg cgtcgcaagg tactgctttc caaacccagg caggaagaga ttccttccgt    660
gagtctttgt ctgcgttacc ttcatccgtt gtagatatta attctaggtt cccgagtgcg    720
ggttttacg ctttcctcaa cggtcctgtg ttgaggccta tcttcgtttc gcttcttagc    780
tctacggata cgcgtaatag ggtcattgag gttgtagatc ctagcaatcc gacgactgct    840
gaatcgctta acgcagttaa gcgtactgac gatgcgtcta cagccgctag ggctgagata    900
gataatttaa tagaatcaat ctctaagggg tttgatgttt atgatagggc ttcttttgaa    960
gccgcgtttt cggtagtctg gtcagaggct accacctcca aggcttagcc ttgagggtct   1020
tctgacggtg gtgcacacca tagtgcatag tgctttcccg ttcactttaa tcgaacggtt   1080
tgctcattgg tttgcgaaaa cctctcgcgt gtgacgttga agtttctatg ggcaagccg    1139
```

<210> SEQ ID NO 9
<211> LENGTH: 1139
<212> TYPE: DNA
<213> ORGANISM: Cucumber green mottle mosaic virus
<220> FEATURE:
<223> OTHER INFORMATION: DNA sequence encoding coat protein of CGMMV
      isolate 3

<400> SEQUENCE: 9

```
aattcggctt ctgtaggggt ggtgctactg ttgctttggt tgacacaagg atgcattctg     60
ttgcagaagg aactatatgc aaattttcag ctcccgccac cgtccgcgag ttctctgtta    120
ggttcatccc taactattct gtcgtggttg cggatgccct tcgcgatcct tggtctttat    180
ttgtgaggct ctctaacgta ggtattaagg atggttttca tccattaact ttagaggtcg    240
cctgtctagt tgccactact aactctatta ttaaaaaggg gcttagagct tctgtagttg    300
agtccgttgt ctcttccgat cagtcgattg ttctagattc tttatctgag aaagttgagc    360
ctttcttcga taaagtccct atttcagcgg ctgtaatggc gagagacccc agttataggt    420
ctaggtcgca gtctgtcgtt ggtcgtggta agcggtattc taaacctcca aatcggaggt    480
cgggctctgc ttctgaagag tccagttctg tttctttcga agatggctta caatccgatc    540
acgcctagca aacttattgc gtttagtgct tcttatgttc ccgttagaac tttacttaat    600
tttctagtgg cgtcgcaagg tactgctttc caaacccagg caggaagaga ttccttccgt    660
gagtctttgt ctgcgttacc ttcatccgtc gtagatatta attctaggtt cccgagtgcg    720
ggttttacg ctttcctcaa cggtcctgtg ttgaggccta tcttcgtttc gtttcttagc    780
tctacggata cgcgtaatag ggtcattgag gttgtagatc ctagcaatcc gacgactgct    840
gagtcgctta acgcagttaa gcgtactgac gatgcgtcta cagccgctag ggctgagata    900
gataatttaa tagaatcaat ctctaagggg tttgatgttt atgatagggc ttcttttgaa    960
gccgcgtttt cggtagtctg gtcagaggct accacctcca aggcttagcc ttgagggtct   1020
tctgacggtg gtgcacacca tagtgcatag tgctttcccg ttcactttaa tcgaacggtt   1080
tgctcattgg tttgcgaaaa cctctcgcgt gtgacgttga agtttctatg ggcaagccg    1139
```

<210> SEQ ID NO 10
<211> LENGTH: 1139
<212> TYPE: DNA

```
<213> ORGANISM: Cucumber green mottle mosaic virus
<220> FEATURE:
<223> OTHER INFORMATION: DNA sequence encoding co

```
ggtttttacg ctttcctcaa cggtcctgtg ttgaggccta tcttcgtttc gcttcttagc    780
tctacggata cgcgtaatag ggtcattgag gttgtagatc ctagcaatcc gacgactgct    840
gagtcgctta acgcagttaa gcgtactgac gatgcgtcta cagccgctag gctgagata    900 gataatttaa tagaatcaat ctctaagggg tttgatgttt atgatagggc ttcttttgaa    960
gccgcgtttt cggtagtctg gtcagaggct accacctcca aggcttagcc ttgagggtct   1020
tctgacggtg gtgcacacca tagtgcatag tgctttcccg ttcactttaa tcgaacggtt   1080
tgctcattgg tttgcgaaaa cctctcgcgt gtgacgttga agtttctatg ggcaagccg    1139
```

<210> SEQ ID NO 12
<211> LENGTH: 1139
<212> TYPE: DNA
<213> ORGANISM: Cucumber green mottle mosaic virus
<220> FEATURE:
<223> OTHER INFORMATION: DNA sequence encoding coat protein of CGMMV
      isloate 6

<400> SEQUENCE: 12

```
aattcggctt ctgtaggggt ggtgctactg ttgctttggt tgacacaagg atgcattctg     60
ttgcagaagg aactatatgc aaattttcag ctcccgccac cgtccgcgag ttctctgtta    120
ggttcatccc taactattct gtcgtggttg cggatgccct tcgcgatcct tggtctttat    180
ttgtgaggct ctcaacgta ggtattaagg atggttttca tccattaact ttagaggtcg    240
cctgtctagt tgccactact aactctatta ttaaaaagga gcttagagct tctgtagttg    300
agtccgttgt ctcttccgat cagtcgattg ttctagattc tttatctgag aaagttgagc    360 cttcttcga taaagtccct atttcagcgg ctgtaatggc gagagacccc agttataggt    420
ctaggtcgca gtctgtcgtt ggtcgtggta agcggcattc taaacctcca aatcggaggt    480
cggactctgc ttctgaagag tccagttctg tttctttcga agatggctta caatccgatc    540
acgcctagca aacttattgc gtttagtgct tcttatgttc ccgttagaac tttacttaat    600
tttctagtgg cgtcgcaagg tactgctttc caaacccagg caggaagaga ttccttccgt    660
gagtctttgt ctgcgttacc ttcatccgtt gtagatatta attctaggtt cccgagtgcg    720 ggttttacg ctttcctcaa cggtcctgtg ttgaggccta tcttcgtttc gcttcttagc    780
tctacggata cgcgtaatag ggtcattgag gttgtagatc ctagcaatcc gacgactgct    840
gaatcgctta acgcagttaa gcgtactgac gatgcgtcta cagccgctag gctgagata    900 gataatttaa tagaatcaat ctctaagggg tttgatgttt atgacagggc ttcttttgaa    960
gccgcgtttt cggtagtctg gtcagaggct accacctcca aggcttagcc ttgagggtct   1020
tctgacggtg gtgcacacca tagtgcatag tgctttcccg ttcactttaa tcgaacggtt   1080
tgctcattgg tttgcgaaaa cctctcgcgt gtgacgttga agtttctatg ggcaagccg    1139
```

<210> SEQ ID NO 13
<211> LENGTH: 1138
<212> TYPE: DNA
<213> ORGANISM: Cucumber green mottle mosaic virus
<220> FEATURE:
<223> OTHER INFORMATION: DNA sequence encoding coat protein of CGMMV
      isolate 7

<400> SEQUENCE: 13

```
aattcggctt ctgtaggggt ggtgctactg ttgctttggt tgacacaagg atgcattctg     60
ttgcagaagg aactatatgc aaattttcag ctcccgccac cgtccgcgag ttctctgtta    120
```

```
ggttcatccc taactattct gtcgtggttg cggatgccct tcgcgatcct tggtctttat        180
ttgtgaggct ctctaacgta ggtattaagg atggttttca tccattaact ttagaggtcg        240
cctgtctagt tgccactact aactctatta ttaaaaaggg gcttagagct tctgtagttg        300
agtccgttgt ctcttccgat cagtcgattg ttctagattc tttatctgag aaagttgagc        360
ctttcttcga taaagtccct atttcagcgg ctgtgatggc gagggacccc agttataggt        420
ctaggtcgca gtcgtcgtt ggtcgtggta agcggcattc taaacctcca aatcggaggt         480
cggactctgc ttctgaagag tccagttctg tttctttcga agatggctta caatccgatc        540
acgcctagca aacttattgc gtttagtgct tcttatgttc ccgttagaac tttacttaat        600
tttctagtgg cgtcgcaagg tactgctttc caaacccagg caggaagaga ttccttccgt        660
gagtctttgt ctgcgttacc ttcatccgtt gtagatatta attctaggtt cccgaatgcg        720 ggttttacg ctttcctcaa cggtcctgtg ttgaggccta tcttcgtttc gcttcttagc        780
tctacggata cgcgtaatag ggtcattgag gttgttgatc ctagcaatcc gacgactgct       840
gagtcgctta acgcagttaa gcgtactgac gatgcgtcta cagccgctag ggctgagata       900
gataatttaa tagaatcaat ctctaagggg tttgatgttt atgataggc ttcttttgaa         960 gccgcgtttt cggtagtctg gtcagaggct accacctcca aggcttagcc ttgagggtct       1020
tctgacggtg gtgcacacca tagtgcatag tgctttcccg ttcactttaa tcgaacggtt       1080
tgctcattgg tttgcgaaaa ctctcgcgtg tgacgttgaa gtttctatgg gcaagccg        1138

<210> SEQ ID NO 14
<211> LENGTH: 1139
<212> TYPE: DNA
<213> ORGANISM: Cucumber green mottle mosaic virus
<220> FEATURE:
<223> OTHER INFORMATION: DNA sequence encoding coat protein of CGMMV
     isolate 8

<400> SEQUENCE: 14
aattcggctt ctgtaggggt ggtgctactg ttgctttggt tgacacaagg atgcattctg          60
ttgcagaagg aactatatgc aaattttcag ctcccgccac cgtccgcgag ttctctgtta        120
ggttcatccc taactattct gtcgtggttg cggatgccct tcgcgatcct tggtctttat        180
ttgtgaggct ctctaacgta ggtattaagg atggttttca tccattaact ttagaggtcg        240
cctgtctagt tgccactact aactctatta ttaaaaaggg gcttagagct tctgtagttg        300
agtccgttgt ctcttccgat cagtcgattg ttctagattc tttatctgag aaagttgagc        360
ctttcttcga taaagtccct atttcagcgg ctgtaatggc gagagacccc agttataggt        420
ctaggtcgca gtcgtcgtt ggtcgtggta agcggcattc taaacctcca aatcggaggt         480
cggactctgc ttctgaagag tccagttctg tttctttcga agatggctta caatccgatc        540
acgcctagca aacttattgc gtttagtgct tcttatgctc ccgttagaac tttacttaat        600
tttctagtgg cgtcgcaagg tactgctttc caaatccagg caggaagaga ttccttccgt        660
gagtctttgt ctgcgttacc ttcatccgtt gtagatatta attctaggtt cccgagtgcg        720 ggttttacg ctttcctcaa cggtcctgtg ttgaggccta tcttcgtttc gcttcttagc        780
tctacggata cgcgtaatag ggtcattgag gttgtagatc ctagcaatcc gacgactgct       840
gaatcgctta acgcagttaa gcgtactgac gatgcgtcta cagccgctag ggctgagata       900
gataatttaa tagaatcaat ctctaagggg tttgatgttt atgataggc ttcttttgaa         960 gccgcgtttt cggtagtctg gtcagaggct accacctcca aggcttagcc ttgagggtct       1020
```

```
tctgacggtg gtgcacacca tagtgcatag tgctttcccg ttcactttaa tcgaacggtt    1080
tgctcattgg tttgcgaaaa cctctcgcgt gtgacgttga agtttctatg ggcaagccg     1139
```

<210> SEQ ID NO 15
<211> LENGTH: 1139
<212> TYPE: DNA
<213> ORGANISM: Cucumber green mottle mosaic virus
<220> FEATURE:
<223> OTHER INFORMATION: DNA sequence encoding coat protein of CGMMV
      isolate 9

<400> SEQUENCE: 15

```
aattcggctt ctgtaggggt ggtgctactg ttgctttggt tgacacaagg atgcattctg      60
ttgcagaagg aactatatgc aaattttcag ctcccgccac cgtccgcgag ttctctgtta    120
ggttcatccc taactattct gtcgtggctg cggatgccct tcgcgatcct tggtctttat    180
ttgtgaggct ctctaacgta ggcattaagg atggttttca tccattaact ttagaggtcg    240
cctgtctagt tgccactact aactctatta ttaaaaaggg gcttagagct tctgtagttg    300
agtccgttgt ctcttccgat cagtcgattg ttctagattc tttgtctgag aaagttgagc    360 cttttcttcga taaagtccct atttcagcgg ctgtaatggc tagagacccc agttataggt    420
ctaggtcaca gtctgtcgtt ggtcgtggta agcggcattc taaacctcca aatcggaggt    480
cggactctgc ttctgaagag tccagttctg tttcttttga agatggctta caatccgatc    540
acgcctagca aacttattgc gtttagtgct tcatatgttc ccgttagaac tttacttaat    600
tttctagtgg cgtcgcaagg tactgctttt caaacccagg caggaagaga ttccttccgt    660
gagtctttgt ctgcgttacc ttcatccgtt gtagatatta attctaggtt cccgagtgcg    720
ggtttttacg ctttcctcaa cggtcctgtg ttgaggccta tcttcgtttc gcttcttagc    780
tctacggata cgcgtaatag ggtcattgag gttgtagatc ctagcaatcc gacgactgct    840
gagtcgctta acgcagttaa gcgtactgac gatgcgtcta cagccgctag ggctgagata    900 gataattaa tagaatcaat ctctaagggg tttgatgttt atgatagggc ttccctttgaa    960 gccgcgtttt cggtagtctg gtcagaggct accacctcca aggcttagcc ttgagggtct   1020
tctgacggtg gtgcacacca tagtgcatag tgttttcccg ttcactttaa tcgaacggtt   1080
tgctcattgg tttgcgaaaa cctctcgcgt gtgacgttga agtttctatg ggcaagccg    1139
```

<210> SEQ ID NO 16
<211> LENGTH: 1139
<212> TYPE: DNA
<213> ORGANISM: Cucumber green mottle mosaic virus
<220> FEATURE:
<223> OTHER INFORMATION: DNA sequence encoding coat protein of CGMMV
      isolate 10

<400> SEQUENCE: 16

```
aattcggctt ctgtaggggt ggtgctactg ttgctttggt tgacacaagg atgcattctg      60
ttgcagaagg aactatatgc aaattttcag ctcccgccac cgtccgcgag ttctctgtta    120
ggttcatccc taactattct gtcgtggctg cggatgccct tcgcgatcct tggtctttat    180
ttgtgaggct ctctaacgta ggcattaagg atggttttca tccattaact ttagaggtcg    240
cctgtctagt tgccactact aactctatta ttaaaaaggg gcttagagct tctgtagttg    300
agtccgttgt ctcttccgat cagtcgattg ttctagattc tttgtctgag aaagttgagc    360 cttttcttcga taaagtccct atttcagcgg ctgtaatggc tagagacccc agttataggt    420
ctaggtcaca gtctgtcgtt ggtcgtggta agcggcattc taaacctcca aatcggaggt    480
```

```
cggactctgc ttctgaagag tccagttctg tttcttttga agatggctta caatccgatc    540
acgcctagca aacttattgc gtttagtgct tcatatgttc ccgttagaac tttacttaat    600
tttctagtgg cgtcgcaagg tactgctttt caaacccagg caggaagaga ttccttccgt    660
gagtctttgt ctgcgttacc ttcatccgtt gtagatatta attctaggtt cccgagtgcg    720 ggttttacg ctttcctcaa cggtcctgtg ttgaggccta tcttcgtttc gcttcttagc    780
tctacggata cgcgtaatag ggtcattgag gttgtagatc ctagcaatcc gacgactgct    840
gagtcgctta acgcagttaa gcgtactgac gatgcgtcta cagccgctag gctgagata    900 gataatttaa tagaatcaat ctctaagggg tttgatgttt atgatagggc ttcctttgaa    960
gccgcgtttt cggtagtctg tcagaggct accacctcca aggcttagcc ttgagggtct    1020
tctgacggtg gtgcacacca tagtgcatag tgctttcccg ttcactttaa tcgaacggtt   1080
tgctcattgg tttgcgaaaa cctctcgcgt gtgacgttga agtttctatg gcaagccg     1139
```

<210> SEQ ID NO 17
<211> LENGTH: 3429
<212> TYPE: DNA
<213> ORGANISM: Cucumber green mottle mosaic virus
<220> FEATURE:
<223> OTHER INFORMATION: DNA sequence encoding 129 kD replicase of CGMMV strain SH

<400> SEQUENCE: 17

```
atggcaaaca ttaatgaaca aatcaacaac caacgtgacg ccgcggctag cgggagaaac     60
aatctcgtta gccaattggc gtcaaaaagg gtgtatgacg aggctgttcg ctcgttggat    120
catcaagaca gacgcccgaa aatgaatttt tctcgtgtgg tcagcacaga gcacaccagg    180
cttgtaactg acgcgtatcc ggagttttcg attagcttta ccgccaccaa gaactctgta    240
cactcccttg cgggtggtct gaggcttctt gaattggaat atatgatgat gcaggtgccc    300
tacggctcac cttgttatga catcggcggt aactatacgc agcacttgtt caaaggtaga    360
tcatatgtgc attgctgcaa tccgtgccta gatcttaagg atgttgcgag gaatgtgatg    420
tacaacgata tgattacgca acatgtacag aggcacaagg gatcttgcgg gtgcagacct    480
cttccaactt tccagataga tgcattcagg aggtacgata gttctccctg tgcggtcacc    540
tgttcagacg tttttccaaga gtgttcctat gattttggga gtggtaggga taatcatgca    600
gtctcgttgc attcaatcta cgatatccct tattcttcga tcggacctgc tcttcatagg    660
aagaatgtgc gagtttgtta tgcagccttt catttctcgg aggcattgct tttaggttcg    720
cctgtaggta atttaaatag tattggggct cagtttaggg tcgatggtga tgatgtgcat    780
tttcttttta gtgaagagtc tactttgcat tatactcata gttagaaaaa tatcaagtta    840
atcgtgatgc gtacttactt tcctgctgat gataggtttg tatatattaa ggagttcatg    900
gttaagcgtg tggatacttt tttctttagg ttggtcagag cagatacaca catgcttcat    960
aaatctgtgg ggcactattc gaaatcgaag tctgagtact tcgcgctgaa taccccctccg   1020 atcttccaag ataaagccac gttttctgtg tggtttcctg aagcgaagaa ggtgttgata    1080
cccaagtttg aactttcgag attcctttct gggaatgtga aaatctctag gatgcttgtc    1140
gatgctgatt tcgtccatac cattattaat cacattagca cgtatgataa caaggcctta    1200
gtgtggaaga atgttcagtc ctttgtggaa tccatacgtt caagagtaat tgtaaacgga    1260
gtttccgtga atctgagtg gaacgtaccg gttgatcagc tcactgatat ctcgttctcg    1320
atattccctc tcgtgaaggt taggaaggta cagatcgagt taatgtctga taaagttgta    1380
```

```
atcgaggcga ggggtttgct tcggaggttc gcagacagtc ttaaatctgc cgtagaagga   1440
ctaggtgatt gcgtctatga tgctctagtt caaaccggct ggtttgacac ctctagcgac   1500
gaactgaaag tattgctacc tgaaccgttt atgaccttt cggattatct tgaagggatg    1560
tacgaggcag atgcaaagat cgagagagag agtgtctctg agttgctcgc ttccggtgat   1620
gatttgttca agaaaatcga tgagataaga aacaattaca gtggagtcga atttgatgta   1680
gagaaattcc aagaattttg caaggaactg aatgttaatc ctatgctaat tggccatgtc   1740
atcgaagcta ttttttcgca gaaggctggg gtaacagtaa cgggtctggg cacgctctct   1800
cctgagatgg gcgcttctgt tgcgttatcc agtacctctg tagatacatg tgaagatatg   1860
gatgtaactg aagatatgga ggatatagtg ttgatggcgg acaagagtca ttcttacatg   1920
tcccctgaaa tggcgagatg ggctgatgtt aaatatggca acaataaagg ggctctagtc   1980
gagtacaaag tcggaacctc gatgacttta cctgccacct gggcagagaa agttaaggct   2040
gtcttaccgt tgtcggggat ctgtgtgagg aaaccccaat tttcgaagcc gcttgatgag   2100
gaagatgact tgaggttatc aaacatgaat ttctttaagg tgagcgatct aaagttgaag   2160
aagactatca ctccagtcgt ttacactggg accattcgag agaggcaaat gaagaattat   2220
attgattact tatcggcctc tcttggttcc acgctgggta atctggagag aatcgtgcgg   2280
agtgattgga atggtactga ggagagtatg caaacgttcg ggttgtatga ctgcgaaaag   2340
tgcaagtggt tattgttgcc agccgagaag aagcacgcat gggccgtggt tctggcaagt   2400
gacgatacca ctcgcataat cttcctttca tatgacgaat ctggttctcc tataattgat   2460
aagaaaaact ggaagcgatt tgctgtctgt tccgagacca agtctatag tgtaattcgt    2520 agcttagagg ttctaaataa ggaagcaata gtcgaccccg gggttcacat aacattagtt   2580
gacggagtgc cgggttgtgg aaagaccgcc gagattatag cgagggtcaa ttggaaaact   2640
gatctagtat tgactcccgg aagggaggca gctgctatga ttaggcggag agcctgcgcc   2700
ctgcacaagt cacctgtggc aaccaatgac aacgtcagaa ctttcgattc ttttgtgatg   2760
aataggaaaa tcttcaagtt tgacgctgtc tatgttgacg agggtctgat ggtccatacg   2820
ggattactta attttgcgtt aaagatctca ggttgtaaaa aagccttcgt ctttggtgat   2880
gctaagcaaa tcccgtttat aaacagagtc atgaatttcg attatcctaa ggagttaaga   2940
actttaatag tcgataatgt agagcgtagg tatgtcaccc ataggtgtcc tagagatgtc   3000
actagttttc ttaatactat ctataaagcc gctgtcgcta ctactagtcc ggttgtacat   3060
tctgtgaagg caattaaagt gtcaggggcc ggtattctga ggcctgagtt gacaaagatc   3120
aaaggaaaga taataacgtt tactcaatct gataagcagt ccttgatcaa gagtgggtac   3180
aatgatgtga atactgtgca tgaaattcag ggagaaacct tgaggagac ggcagttgtg    3240 cgtgccaccc cgactccaat aggtttgatt gcccgtgatt caccacatgt actagtggcc   3300
ttaactaggc acactaaggc aatggtgtat tatactgttg tattcgatgc agttacaagt   3360
ataatagcgg atgtggaaaa ggtcgatcag tcgatcttga ccatgtttgc taccactgtg   3420
cctaccaaa                                                           3429
```

<210> SEQ ID NO 18
<211> LENGTH: 1143
<212> TYPE: PRT
<213> ORGANISM: Cucumber green mottle mosaic virus
<220> FEATURE:
<223> OTHER INFORMATION: 129 kD replicase of CGMMV strain SH

<400> SEQUENCE: 18

```
Met Ala Asn Ile Asn Glu Gln Ile Asn Asn Gln Arg Asp Ala Ala Ala
 1               5                  10                  15

Ser Gly Arg Asn Asn Leu Val Ser Gln Leu Ala Ser Lys Arg Val Tyr
            20                  25                  30

Asp Glu Ala Val Arg Ser Leu Asp His Gln Asp Arg Arg Pro Lys Met
        35                  40                  45

Asn Phe Ser Arg Val Val Ser Thr Glu His Thr Arg Leu Val Thr Asp
    50                  55                  60

Ala Tyr Pro Glu Phe Ser Ile Ser Phe Thr Ala Thr Lys Asn Ser Val
65                  70                  75                  80

His Ser Leu Ala Gly Gly Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125

Cys Leu Asp Leu Lys Asp Val Ala Arg Asn Val Met Tyr Asn Asp Met
    130                 135                 140

Ile Thr Gln His Val Gln Arg His Lys Gly Ser Cys Gly Cys Arg Pro
145                 150                 155                 160

Leu Pro Thr Phe Gln Ile Asp Ala Phe Arg Arg Tyr Asp Ser Ser Pro
                165                 170                 175

Cys Ala Val Thr Cys Ser Asp Val Phe Gln Glu Cys Ser Tyr Asp Phe
            180                 185                 190

Gly Ser Gly Arg Asp Asn His Ala Val Ser Leu His Ser Ile Tyr Asp
        195                 200                 205

Ile Pro Tyr Ser Ser Ile Gly Pro Ala Leu His Arg Lys Asn Val Arg
    210                 215                 220

Val Cys Tyr Ala Ala Phe His Phe Ser Glu Ala Leu Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Glu Ser Thr Leu His Tyr Thr
            260                 265                 270

His Ser Leu Glu Asn Ile Lys Leu Ile Val Met Arg Thr Tyr Phe Pro
        275                 280                 285

Ala Asp Asp Arg Phe Val Tyr Ile Lys Glu Phe Met Val Lys Arg Val
    290                 295                 300

Asp Thr Phe Phe Phe Arg Leu Val Arg Ala Asp Thr His Met Leu His
305                 310                 315                 320

Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
            340                 345                 350

Pro Glu Ala Lys Lys Val Leu Ile Pro Lys Phe Glu Leu Ser Arg Phe
        355                 360                 365

Leu Ser Gly Asn Val Lys Ile Ser Arg Met Leu Val Asp Ala Asp Phe
    370                 375                 380

Val His Thr Ile Ile Asn His Ile Ser Thr Tyr Asp Asn Lys Ala Leu
385                 390                 395                 400

Val Trp Lys Asn Val Gln Ser Phe Val Glu Ser Ile Arg Ser Arg Val
                405                 410                 415
```

```
Ile Val Asn Gly Val Ser Val Lys Ser Glu Trp Asn Pro Val Asp
            420                 425                 430

Gln Leu Thr Asp Ile Ser Phe Ser Ile Phe Pro Leu Val Lys Val Arg
            435                 440                 445

Lys Val Gln Ile Glu Leu Met Ser Asp Lys Val Val Ile Glu Ala Arg
            450                 455                 460

Gly Leu Leu Arg Arg Phe Ala Asp Ser Leu Lys Ser Ala Val Glu Gly
465                 470                 475                 480

Leu Gly Asp Cys Val Tyr Asp Ala Leu Val Gln Thr Gly Trp Phe Asp
                485                 490                 495

Thr Ser Ser Asp Glu Leu Lys Val Leu Leu Pro Glu Pro Phe Met Thr
                500                 505                 510

Phe Ser Asp Tyr Leu Glu Gly Met Tyr Glu Ala Asp Ala Lys Ile Glu
                515                 520                 525

Arg Glu Ser Val Ser Glu Leu Leu Ala Ser Gly Asp Asp Leu Phe Lys
            530                 535                 540

Lys Ile Asp Glu Ile Arg Asn Asn Tyr Ser Gly Val Glu Phe Asp Val
545                 550                 555                 560

Glu Lys Phe Gln Glu Phe Cys Lys Glu Leu Asn Val Asn Pro Met Leu
                565                 570                 575

Ile Gly His Val Ile Glu Ala Ile Phe Ser Gln Lys Ala Gly Val Thr
                580                 585                 590

Val Thr Gly Leu Gly Thr Leu Ser Pro Glu Met Gly Ala Ser Val Ala
            595                 600                 605

Leu Ser Ser Thr Ser Val Asp Thr Cys Glu Asp Met Asp Val Thr Glu
            610                 615                 620

Asp Met Glu Asp Ile Val Leu Met Ala Asp Lys Ser His Ser Tyr Met
625                 630                 635                 640

Ser Pro Glu Met Ala Arg Trp Ala Asp Val Lys Tyr Gly Asn Asn Lys
                645                 650                 655

Gly Ala Leu Val Glu Tyr Lys Val Gly Thr Ser Met Thr Leu Pro Ala
                660                 665                 670

Thr Trp Ala Glu Lys Val Lys Ala Val Leu Pro Leu Ser Gly Ile Cys
            675                 680                 685

Val Arg Lys Pro Gln Phe Ser Lys Pro Leu Asp Glu Glu Asp Leu
            690                 695                 700

Arg Leu Ser Asn Met Asn Phe Phe Lys Val Ser Asp Leu Lys Leu Lys
705                 710                 715                 720

Lys Thr Ile Thr Pro Val Val Tyr Thr Gly Thr Ile Arg Glu Arg Gln
                725                 730                 735

Met Lys Asn Tyr Ile Asp Tyr Leu Ser Ala Ser Leu Gly Ser Thr Leu
                740                 745                 750

Gly Asn Leu Glu Arg Ile Val Arg Ser Asp Trp Asn Gly Thr Glu Glu
            755                 760                 765

Ser Met Gln Thr Phe Gly Leu Tyr Asp Cys Glu Lys Cys Lys Trp Leu
            770                 775                 780

Leu Leu Pro Ala Glu Lys Lys His Ala Trp Ala Val Val Leu Ala Ser
785                 790                 795                 800

Asp Asp Thr Thr Arg Ile Ile Phe Leu Ser Tyr Asp Glu Ser Gly Ser
                805                 810                 815

Pro Ile Ile Asp Lys Lys Asn Trp Lys Arg Phe Ala Val Cys Ser Glu
                820                 825                 830
```

-continued

| | | | | | | | | | | | |
|---|---|---|---|---|---|---|---|---|---|---|---|
|Thr|Lys|Val|Tyr|Ser|Val|Ile|Arg|Ser|Leu|Glu|Val|Leu|Asn|Lys|Glu|
| | |835| | | |840| | | |845| |

Ala Ile Val Asp Pro Gly Val His Ile Thr Leu Val Asp Gly Val Pro
            850                 855                 860

Gly Cys Gly Lys Thr Ala Glu Ile Ile Ala Arg Val Asn Trp Lys Thr
865                 870                 875                 880

Asp Leu Val Leu Thr Pro Gly Arg Glu Ala Ala Met Ile Arg Arg
            885                 890                 895

Arg Ala Cys Ala Leu His Lys Ser Pro Val Ala Thr Asn Asp Asn Val
            900                 905                 910

Arg Thr Phe Asp Ser Phe Val Met Asn Arg Lys Ile Phe Lys Phe Asp
            915                 920                 925

Ala Val Tyr Val Asp Glu Gly Leu Met Val His Thr Gly Leu Leu Asn
            930                 935                 940

Phe Ala Leu Lys Ile Ser Gly Cys Lys Lys Ala Phe Val Phe Gly Asp
945                 950                 955                 960

Ala Lys Gln Ile Pro Phe Ile Asn Arg Val Met Asn Phe Asp Tyr Pro
            965                 970                 975

Lys Glu Leu Arg Thr Leu Ile Val Asp Asn Val Glu Arg Tyr Val
            980                 985                 990

Thr His Arg Cys Pro Arg Asp Val Thr Ser Phe Leu Asn Thr Ile Tyr
            995                 1000                1005

Lys Ala Ala Val Ala Thr Thr Ser Pro Val Val His Ser Val Lys Ala
            1010                1015                1020

Ile Lys Val Ser Gly Ala Gly Ile Leu Arg Pro Glu Leu Thr Lys Ile
1025                1030                1035                1040

Lys Gly Lys Ile Ile Thr Phe Thr Gln Ser Asp Lys Gln Ser Leu Ile
            1045                1050                1055

Lys Ser Gly Tyr Asn Asp Val Asn Thr Val His Glu Ile Gln Gly Glu
            1060                1065                1070

Thr Phe Glu Glu Thr Ala Val Val Arg Ala Thr Pro Thr Pro Ile Gly
            1075                1080                1085

Leu Ile Ala Arg Asp Ser Pro His Val Leu Val Ala Leu Thr Arg His
            1090                1095                1100

Thr Lys Ala Met Val Tyr Tyr Thr Val Val Phe Asp Ala Val Thr Ser
1105                1110                1115                1120

Ile Ile Ala Asp Val Glu Lys Val Asp Gln Ser Ile Leu Thr Met Phe
            1125                1130                1135

Ala Thr Thr Val Pro Thr Lys
            1140

<210> SEQ ID NO 19
<211> LENGTH: 1503
<212> TYPE: DNA
<213> ORGANISM: Cucumber green mottle mosaic virus
<220> FEATURE:
<223> OTHER INFORMATION: DNA sequence encoding 57 kD protein of CGMMV
      strain SH

<400> SEQUENCE: 19

```
atgcagaatt cgctgtatgt ccatcgtaat attttcctcc ctgttagtaa aacggggttt      60
tatacagaca tgcaggagtt ctacgataga tgccttcctg ggaattcctt cgtactaaat     120
gatttcgatg ccgtaaccat gcggttgagg gacaacgaat ttaacttaca accttgtagg     180
ctaaccttga gtaatttaga tccggtaccc gctttgatta agaatgaagc gcagaatttt     240
```

```
ctgatcccocg ttttgcgtac ggcctgtgaa aggccgcgca ttccgggtct tcttgagaat      300
cttgtagcta tgataaagag gaatatgaat actcctgatt tagctgggac cgtagatata      360
actaacatgt cgatttctat agtagataac ttcttttctt cttttgttag ggacgaggtt      420
ttgcttgatc acttagattg tgttagggct agttccattc aaagttttc tgattggttt       480 tcgtgtcaac caacctcagc ggttggccag ttagctaatt tcaatttcat agatttgcct      540
gcctttgata cttatatgca tatgattaag aggcaaccca agagtcggtt agatacttcg      600
attcagtctg aatatccggc cttgcaaact attgtttatc ccctaaagt ggtaaatgca       660 gttttggtc cggttttcaa gtatttaacc accaagtttc ttagtatggt agatagttct       720 aagttttct tttacactag gaaaaaacca gaagatctgc aggaatttt ctcagatctc        780 tcttcccatt ctgattatga gattcttgag cttgatgttt ctaaatatga caagtcgcaa      840
tccgatttcc acttctctat tgagatggca atttgggaaa aattagggct tgacgatatt     900
ttggcttgga tgtggtctat gggtcacaaa agaactatac tgcaagattt ccaagccggg      960
ataaagacgc tcatttacta tcaacggaag tctggtgatg taactacttt tataggtaat     1020
acctttatta tcgcagcgtg tgtggctagt atgttgccgt tagataagtg tttaaagct      1080 agttttgtg gtgatgattc gctgatctac cttcctaagg gtttggagta tcctgatata     1140
caggctactg ccaaccttgt ttggaatttt gaggcgaaac ttttccgaaa gaagtatggt    1200
tacttctgcg ggaagtatat aattcaccat gccaacggct gtattgttta ccctgaccct    1260
ttaaaattaa ttagtaaatt aggtaataag agtcttgtag ggtatgagca tgttgaggag    1320
tttcgtatat ctctcctcga cgttgctcat agtttgttta atggtgctta tttccattta    1380
ctcgacgatg caatccacga attatttcct aatgctgggg gttgcagttt tgtaattaat    1440
tgtttgtgta agtatttgag tgataagcgc cttttccgta gtctttacat agatgtctct    1500
aag                                                                    1503

<210> SEQ ID NO 20
<211> LENGTH: 501
<212> TYPE: PRT
<213> ORGANISM: Cucumber green mottle mosaic virus
<220> FEATURE:
<223> OTHER INFORMATION: 57 kD protein of CGMMV strain SH

<400> SEQUENCE: 20

Met Gln Asn Ser Leu Tyr Val His Arg Asn Ile Phe Leu Pro Val Ser
  1               5                  10                  15

Lys Thr Gly Phe Tyr Thr Asp Met Gln Glu Phe Tyr Asp Arg Cys Leu
             20                  25                  30

Pro Gly Asn Ser Phe Val Leu Asn Asp Phe Asp Ala Val Thr Met Arg
         35                  40                  45

Leu Arg Asp Asn Glu Phe Asn Leu Gln Pro Cys Arg Leu Thr Leu Ser
     50                  55                  60

Asn Leu Asp Pro Val Pro Ala Leu Ile Lys Asn Glu Ala Gln Asn Phe
 65                  70                  75                  80

Leu Ile Pro Val Leu Arg Thr Ala Cys Glu Arg Pro Arg Ile Pro Gly
                 85                  90                  95

Leu Leu Glu Asn Leu Val Ala Met Ile Lys Arg Asn Met Asn Thr Pro
            100                 105                 110

Asp Leu Ala Gly Thr Val Asp Ile Thr Asn Met Ser Ile Ser Ile Val
        115                 120                 125

Asp Asn Phe Phe Ser Ser Phe Val Arg Asp Glu Val Leu Leu Asp His
```

-continued

```
    130                 135                 140

Leu Asp Cys Val Arg Ala Ser Ser Ile Gln Ser Phe Ser Asp Trp Phe
145                 150                 155                 160

Ser Cys Gln Pro Thr Ser Ala Val Gly Gln Leu Ala Asn Phe Asn Phe
                165                 170                 175

Ile Asp Leu Pro Ala Phe Asp Thr Tyr Met His Met Ile Lys Arg Gln
            180                 185                 190

Pro Lys Ser Arg Leu Asp Thr Ser Ile Gln Ser Glu Tyr Pro Ala Leu
        195                 200                 205

Gln Thr Ile Val Tyr His Pro Lys Val Val Asn Ala Val Phe Gly Pro
    210                 215                 220

Val Phe Lys Tyr Leu Thr Thr Lys Phe Leu Ser Met Val Asp Ser Ser
225                 230                 235                 240

Lys Phe Phe Phe Tyr Thr Arg Lys Lys Pro Glu Asp Leu Gln Glu Phe
                245                 250                 255

Phe Ser Asp Leu Ser Ser His Ser Asp Tyr Glu Ile Leu Glu Leu Asp
            260                 265                 270

Val Ser Lys Tyr Asp Lys Ser Gln Ser Asp Phe His Phe Ser Ile Glu
        275                 280                 285

Met Ala Ile Trp Glu Lys Leu Gly Leu Asp Asp Ile Leu Ala Trp Met
    290                 295                 300

Trp Ser Met Gly His Lys Arg Thr Ile Leu Gln Asp Phe Gln Ala Gly
305                 310                 315                 320

Ile Lys Thr Leu Ile Tyr Tyr Gln Arg Lys Ser Gly Asp Val Thr Thr
                325                 330                 335

Phe Ile Gly Asn Thr Phe Ile Ile Ala Ala Cys Val Ala Ser Met Leu
            340                 345                 350

Pro Leu Asp Lys Cys Phe Lys Ala Ser Phe Cys Gly Asp Asp Ser Leu
        355                 360                 365

Ile Tyr Leu Pro Lys Gly Leu Glu Tyr Pro Asp Ile Gln Ala Thr Ala
    370                 375                 380

Asn Leu Val Trp Asn Phe Glu Ala Lys Leu Phe Arg Lys Lys Tyr Gly
385                 390                 395                 400

Tyr Phe Cys Gly Lys Tyr Ile Ile His His Ala Asn Gly Cys Ile Val
                405                 410                 415

Tyr Pro Asp Pro Leu Lys Leu Ile Ser Lys Leu Gly Asn Lys Ser Leu
            420                 425                 430

Val Gly Tyr Glu His Val Glu Glu Phe Arg Ile Ser Leu Leu Asp Val
        435                 440                 445

Ala His Ser Leu Phe Asn Gly Ala Tyr Phe His Leu Leu Asp Asp Ala
    450                 455                 460

Ile His Glu Leu Phe Pro Asn Ala Gly Gly Cys Ser Phe Val Ile Asn
465                 470                 475                 480

Cys Leu Cys Lys Tyr Leu Ser Asp Lys Arg Leu Phe Arg Ser Leu Tyr
                485                 490                 495

Ile Asp Val Ser Lys
            500

<210> SEQ ID NO 21
<211> LENGTH: 4932
<212> TYPE: DNA
<213> ORGANISM: Cucumber green mottle mosaic virus
<220> FEATURE:
<223> OTHER INFORMATION: DNA sequence encoding 186 kD protein of CGMMV
strain SH

<400> SEQUENCE: 21

```
atggcaaaca ttaatgaaca atcaacaac caacgtgacg ccgcggctag cgggagaaac      60
aatctcgtta gccaattggc gtcaaaaagg gtgtatgacg aggctgttcg ctcgttggat    120
catcaagaca gacgcccgaa atgaattttt tctcgtgtgg tcagcacaga gcacaccagg    180
cttgtaactg acgcgtatcc ggagttttcg attagcttta ccgccaccaa gaactctgta    240
cactcccttg cgggtggtct gaggcttctt gaattggaat atatgatgat gcaggtgccc    300
tacggctcac cttgttatga catcggcggt aactatacgc agcacttgtt caaaggtaga    360
tcatatgtgc attgctgcaa tccgtgccta gatcttaagg atgttgcgag gaatgtgatg    420
tacaacgata tgattacgca acatgtacag aggcacaagg gatcttgcgg gtgcagacct    480
cttccaactt ccagataga tgcattcagg aggtacgata gttctccctg tgcggtcacc     540
tgttcagacg ttttccaaga gtgttcctat gattttggga gtggtaggga taatcatgca    600
gtctcgttgc attcaatcta cgatatccct tattcttcga tcggacctgc tcttcatagg    660
aagaatgtgc gagtttgtta tgcagccttt catttctcgg aggcattgct tttaggttcg    720
cctgtaggta atttaaatag tattggggct cagtttaggg tcgatggtga tgatgtgcat    780
tttcttttta gtgaagagtc tactttgcat tatactcata gtttagaaaa tatcaagtta    840
atcgtgatgc gtacttactt tcctgctgat gataggtttg tatatattaa ggagttcatg    900
gttaagcgtg tggatacttt tttctttagg ttggtcagag cagatacaca catgcttcat    960
aaatctgtgg ggcactattc gaaatcgaag tctgagtact tcgcgctgaa taccccctccg   1020
atcttccaag ataaagccac gttttctgtg tggtttcctg aagcgaagaa ggtgttgata    1080
cccaagtttg aactttcgag attccttct gggaatgtga aaatctctag gatgcttgtc     1140
gatgctgatt tcgtccatac cattattaat cacattagca cgtatgataa caaggcctta    1200
gtgtggaaga atgttcagtc ctttgtggaa tccatacgtt caagagtaat tgtaaacgga    1260
gtttccgtga atctgagtg gaacgtaccg gttgatcagc tcactgatat ctcgttctcg     1320
atattccctc tcgtgaaggt taggaaggta cagatcgagt taatgtctga taaagttgta    1380
atcgaggcga ggggtttgct tcggaggttc gcagacagtc ttaaatctgc cgtagaagga    1440
ctaggtgatt gcgtctatga tgctctagtt caaaccggct ggtttgacac ctctagcgac    1500
gaactgaaag tattgctacc tgaaccgttt atgaccttt cggattatct tgaagggatg     1560
tacgaggcag atgcaaagat cgagagagag agtgtctctg agttgctcgc ttccggtgat    1620
gatttgttca agaaaatcga tgagataaga acaattaca gtggagtcga atttgatgta     1680
gagaaattcc aagaattttg caaggaactg aatgttaatc ctatgctaat tggccatgtc    1740
atcgaagcta ttttttcgca gaaggctggg gtaacagtaa cgggtctggg cacgctctct    1800
cctgagatgg gcgcttctgt tgcgttatcc agtacctctg tagatacatg tgaagatatg    1860
gatgtaactg aagatatgga ggatatagtg ttgatggcgg acaagagtca ttcttacatg    1920
tccctgaaa tggcgagatg ggctgatgtt aaatatggca acaataaagg ggctctagtc     1980
gagtacaaag tcggaacctc gatgacttta cctgccacct gggcagagaa agttaaggct    2040
gtcttaccgt tgtcggggat ctgtgtgagg aaacccccaat tttcgaagcc gcttgatgag    2100
gaagatgact tgaggttatc aaacatgaat ttctttaagg tgagcgatct aaagttgaag    2160
aagactatca ctccagtcgt ttacactggg accattcgag agaggcaaat gaagaattat    2220
attgattact tatcggcctc tcttggttcc acgctgggta atctggagag aatcgtgcgg    2280
```

```
agtgattgga atggtactga ggagagtatg caaacgttcg ggttgtatga ctgcgaaaag    2340
tgcaagtggt tattgttgcc agccgagaag aagcacgcat gggccgtggt tctggcaagt    2400
gacgatacca ctcgcataat cttcctttca tatgacgaat ctggttctcc tataattgat    2460
aagaaaaact ggaagcgatt tgctgtctgt tccgagacca aagtctatag tgtaattcgt    2520
agcttagagg ttctaaataa ggaagcaata gtcgaccccg gggttcacat aacattagtt    2580
gacggagtgc cgggttgtgg aaagaccgcc gagattatag cgagggtcaa ttggaaaact    2640
gatctagtat tgactcccgg aagggaggca gctgctatga ttaggcggag agcctgcgcc    2700
ctgcacaagt cacctgtggc aaccaatgac aacgtcagaa ctttcgattc ttttgtgatg    2760
aataggaaaa tcttcaagtt tgacgctgtc tatgttgacg agggtctgat ggtccatacg    2820
ggattactta attttgcgtt aaagatctca ggttgtaaaa aagccttcgt ctttggtgat    2880
gctaagcaaa tcccgtttat aaacagagtc atgaatttcg attatcctaa ggagttaaga    2940
actttaatag tcgataatgt agagcgtagg tatgtcaccc ataggtgtcc tagagatgtc    3000
actagttttc ttaatactat ctataaagcc gctgtcgcta ctactagtcc ggttgtacat    3060
tctgtgaagg caattaaagt gtcaggggcc ggtattctga ggcctgagtt gacaaagatc    3120
aaaggaaaga taataacgtt tactcaatct gataagcagt ccttgatcaa gagtgggtac    3180
aatgatgtga atactgtgca tgaaattcag ggagaaacct tgaggagac ggcagttgtg    3240 cgtgccaccc cgactccaat aggtttgatt gcccgtgatt caccacatgt actagtggcc    3300
ttaactaggc acactaaggc aatggtgtat tatactgttg tattcgatgc agttacaagt    3360
ataatagcgg atgtggaaaa ggtcgatcag tcgatcttga ccatgtttgc taccactgtg    3420
cctaccaaaa tgcagaattc gctgtatgtc catcgtaata tttctcctcc tgttagtaaa    3480
acggggtttt atacagacat gcaggagttc tacgatagat gccttcctgg gaattccttc    3540
gtactaaatg atttcgatgc cgtaaccatg cggttgaggg acaacgaatt taacttacaa    3600
ccttgtaggc taaccttgag taatttagat ccggtacccg ctttgattaa gaatgaagcg    3660
cagaattttc tgatcccgcgt tttgcgtacg gcctgtgaaa ggccgcgcat tccgggtctt    3720
cttgagaatc ttgtagctat gataaagagg aatatgaata ctcctgattt agctgggacc    3780
gtagatataa ctaacatgtc gatttctata gtagataact tctttcttc ttttgttagg    3840 gacgaggttt tgcttgatca cttagattgt gttagggcta gttccattca aagtttttct    3900
gattggtttt cgtgtcaacc aacctcagcg gttggccagt tagctaattt caatttcata    3960
gatttgcctg cctttgatac ttatatgcat atgattaaga ggcaacccaa gagtcggtta    4020
gatacttcga ttcagtctga atatccggcc ttgcaaacta ttgtttatca ccctaaagtg    4080
gtaaatgcag ttttttggtcc ggttttcaag tatttaacca ccaagtttct tagtatggta    4140
gatagttcta agtttttctt ttacactagg aaaaaccag aagatctgca ggaattttc    4200 tcagatctct cttcccattc tgattatgag attcttgagc ttgatgtttc taaatatgac    4260
aagtcgcaat ccgatttcca cttctctatt gagatggcaa tttgggaaaa attagggctt    4320
gacgatattt tggcttggat gtggtctatg ggtcacaaaa gaactatact gcaagatttc    4380
caagccggga taaagacgct catttactat caacggaagt ctggtgatgt aactactttt    4440
ataggtaata ccttattat cgcagcgtgt gtggctagta tgttgccgtt agataagtgt    4500
tttaaagcta gttttttgtgg tgatgattcg ctgatctacc ttcctaaggg tttggagtat    4560
cctgatatac aggctactgc caaccttgtt tggaattttg aggcgaaact tttccgaaag    4620
aagtatggtt acttctgcgg gaagtatata attcaccatg ccaacggctg tattgtttac    4680
```

```
cctgacccct taaaattaat tagtaaatta ggtaataaga gtcttgtagg gtatgagcat    4740
gttgaggagt tcgtatatc tctcctcgac gttgctcata gtttgtttaa tggtgcttat    4800
ttccatttac tcgacgatgc aatccacgaa ttatttccta atgctggggg ttgcagtttt    4860
gtaattaatt gtttgtgtaa gtatttgagt gataagcgcc ttttccgtag tctttacata    4920
gatgtctcta ag                                                       4932
```

```
<210> SEQ ID NO 22
<211> LENGTH: 1644
<212> TYPE: PRT
<213> ORGANISM: Cucumber green mottle mosaic virus
<220> FEATURE:
<223> OTHER INFORMATION: 186 kD protein of CGMMV strain SH

<400> SEQUENCE: 22
```

Met Ala Asn Ile Asn Glu Gln Ile Asn Asn Gln Arg Asp Ala Ala
 1               5                  10                  15

Ser Gly Arg Asn Asn Leu Val Ser Gln Leu Ala Ser Lys Arg Val Tyr
                20                  25                  30

Asp Glu Ala Val Arg Ser Leu Asp His Gln Asp Arg Arg Pro Lys Met
            35                  40                  45

Asn Phe Ser Arg Val Val Ser Thr Glu His Thr Arg Leu Val Thr Asp
        50                  55                  60

Ala Tyr Pro Glu Phe Ser Ile Ser Phe Thr Ala Thr Lys Asn Ser Val
    65                  70                  75                  80

His Ser Leu Ala Gly Gly Leu Arg Leu Leu Glu Leu Glu Tyr Met Met
                85                  90                  95

Met Gln Val Pro Tyr Gly Ser Pro Cys Tyr Asp Ile Gly Gly Asn Tyr
            100                 105                 110

Thr Gln His Leu Phe Lys Gly Arg Ser Tyr Val His Cys Cys Asn Pro
        115                 120                 125

Cys Leu Asp Leu Lys Asp Val Ala Arg Asn Val Met Tyr Asn Asp Met
    130                 135                 140

Ile Thr Gln His Val Gln Arg His Lys Gly Ser Cys Gly Cys Arg Pro
145                 150                 155                 160

Leu Pro Thr Phe Gln Ile Asp Ala Phe Arg Arg Tyr Asp Ser Ser Pro
                165                 170                 175

Cys Ala Val Thr Cys Ser Asp Val Phe Gln Glu Cys Ser Tyr Asp Phe
            180                 185                 190

Gly Ser Gly Arg Asp Asn His Ala Val Ser Leu His Ser Ile Tyr Asp
        195                 200                 205

Ile Pro Tyr Ser Ser Ile Gly Pro Ala Leu His Arg Lys Asn Val Arg
    210                 215                 220

Val Cys Tyr Ala Ala Phe His Phe Ser Glu Ala Leu Leu Gly Ser
225                 230                 235                 240

Pro Val Gly Asn Leu Asn Ser Ile Gly Ala Gln Phe Arg Val Asp Gly
                245                 250                 255

Asp Asp Val His Phe Leu Phe Ser Glu Ser Thr Leu His Tyr Thr
            260                 265                 270

His Ser Leu Glu Asn Ile Lys Leu Ile Val Met Arg Thr Tyr Phe Pro
        275                 280                 285

Ala Asp Asp Arg Phe Val Tyr Ile Lys Glu Phe Met Val Lys Arg Val
    290                 295                 300

Asp Thr Phe Phe Phe Arg Leu Val Arg Ala Asp Thr His Met Leu His

-continued

```
            305                 310                 315                 320
Lys Ser Val Gly His Tyr Ser Lys Ser Lys Ser Glu Tyr Phe Ala Leu
                325                 330                 335

Asn Thr Pro Pro Ile Phe Gln Asp Lys Ala Thr Phe Ser Val Trp Phe
                340                 345                 350

Pro Glu Ala Lys Lys Val Leu Ile Pro Lys Phe Glu Leu Ser Arg Phe
                355                 360                 365

Leu Ser Gly Asn Val Lys Ile Ser Arg Met Leu Val Asp Ala Asp Phe
        370                 375                 380

Val His Thr Ile Ile Asn His Ile Ser Thr Tyr Asp Asn Lys Ala Leu
385                 390                 395                 400

Val Trp Lys Asn Val Gln Ser Phe Val Glu Ser Ile Arg Ser Arg Val
                405                 410                 415

Ile Val Asn Gly Val Ser Val Lys Ser Glu Trp Asn Val Pro Val Asp
                420                 425                 430

Gln Leu Thr Asp Ile Ser Phe Ser Ile Phe Pro Leu Val Lys Val Arg
                435                 440                 445

Lys Val Gln Ile Glu Leu Met Ser Asp Lys Val Val Ile Glu Ala Arg
        450                 455                 460

Gly Leu Leu Arg Arg Phe Ala Asp Ser Leu Lys Ser Ala Val Glu Gly
465                 470                 475                 480

Leu Gly Asp Cys Val Tyr Asp Ala Leu Val Gln Thr Gly Trp Phe Asp
                485                 490                 495

Thr Ser Ser Asp Glu Leu Lys Val Leu Leu Pro Glu Pro Phe Met Thr
                500                 505                 510

Phe Ser Asp Tyr Leu Glu Gly Met Tyr Glu Ala Asp Ala Lys Ile Glu
                515                 520                 525

Arg Glu Ser Val Ser Glu Leu Leu Ala Ser Gly Asp Asp Leu Phe Lys
        530                 535                 540

Lys Ile Asp Glu Ile Arg Asn Asn Tyr Ser Gly Val Glu Phe Asp Val
545                 550                 555                 560

Glu Lys Phe Gln Glu Phe Cys Lys Glu Leu Asn Val Asn Pro Met Leu
                565                 570                 575

Ile Gly His Val Ile Glu Ala Ile Phe Ser Gln Lys Ala Gly Val Thr
                580                 585                 590

Val Thr Gly Leu Gly Thr Leu Ser Pro Glu Met Gly Ala Ser Val Ala
                595                 600                 605

Leu Ser Ser Thr Ser Val Asp Thr Cys Glu Asp Met Asp Val Thr Glu
        610                 615                 620

Asp Met Glu Asp Ile Val Leu Met Ala Asp Lys Ser His Ser Tyr Met
625                 630                 635                 640

Ser Pro Glu Met Ala Arg Trp Ala Asp Val Lys Tyr Gly Asn Asn Lys
                645                 650                 655

Gly Ala Leu Val Glu Tyr Lys Val Gly Thr Ser Met Thr Leu Pro Ala
                660                 665                 670

Thr Trp Ala Glu Lys Val Lys Ala Val Leu Pro Leu Ser Gly Ile Cys
                675                 680                 685

Val Arg Lys Pro Gln Phe Ser Lys Pro Leu Asp Glu Glu Asp Asp Leu
        690                 695                 700

Arg Leu Ser Asn Met Asn Phe Phe Lys Val Ser Asp Leu Lys Leu Lys
705                 710                 715                 720

Lys Thr Ile Thr Pro Val Val Tyr Thr Gly Thr Ile Arg Glu Arg Gln
                725                 730                 735
```

```
Met Lys Asn Tyr Ile Asp Tyr Leu Ser Ala Ser Leu Gly Ser Thr Leu
            740                 745                 750

Gly Asn Leu Glu Arg Ile Val Arg Ser Asp Trp Asn Gly Thr Glu Glu
            755                 760                 765

Ser Met Gln Thr Phe Gly Leu Tyr Asp Cys Glu Lys Cys Lys Trp Leu
            770                 775                 780

Leu Leu Pro Ala Glu Lys Lys His Ala Trp Ala Val Val Leu Ala Ser
785                 790                 795                 800

Asp Asp Thr Thr Arg Ile Ile Phe Leu Ser Tyr Asp Glu Ser Gly Ser
                805                 810                 815

Pro Ile Ile Asp Lys Lys Asn Trp Lys Arg Phe Ala Val Cys Ser Glu
                820                 825                 830

Thr Lys Val Tyr Ser Val Ile Arg Ser Leu Glu Val Leu Asn Lys Glu
                835                 840                 845

Ala Ile Val Asp Pro Gly Val His Ile Thr Leu Val Asp Gly Val Pro
                850                 855                 860

Gly Cys Gly Lys Thr Ala Glu Ile Ile Ala Arg Val Asn Trp Lys Thr
865                 870                 875                 880

Asp Leu Val Leu Thr Pro Gly Arg Glu Ala Ala Met Ile Arg Arg
                885                 890                 895

Arg Ala Cys Ala Leu His Lys Ser Pro Val Ala Thr Asn Asp Asn Val
                900                 905                 910

Arg Thr Phe Asp Ser Phe Val Met Asn Arg Lys Ile Phe Lys Phe Asp
                915                 920                 925

Ala Val Tyr Val Asp Glu Gly Leu Met Val His Thr Gly Leu Leu Asn
                930                 935                 940

Phe Ala Leu Lys Ile Ser Gly Cys Lys Lys Ala Phe Val Phe Gly Asp
945                 950                 955                 960

Ala Lys Gln Ile Pro Phe Ile Asn Arg Val Met Asn Phe Asp Tyr Pro
                965                 970                 975

Lys Glu Leu Arg Thr Leu Ile Val Asp Asn Val Glu Arg Arg Tyr Val
                980                 985                 990

Thr His Arg Cys Pro Arg Asp Val Thr Ser Phe Leu Asn Thr Ile Tyr
                995                 1000                1005

Lys Ala Ala Val Ala Thr Thr Ser Pro Val Val His Ser Val Lys Ala
            1010                1015                1020

Ile Lys Val Ser Gly Ala Gly Ile Leu Arg Pro Glu Leu Thr Lys Ile
1025                1030                1035                1040

Lys Gly Lys Ile Ile Thr Phe Thr Gln Ser Asp Lys Gln Ser Leu Ile
                1045                1050                1055

Lys Ser Gly Tyr Asn Asp Val Asn Thr Val His Glu Ile Gln Gly Glu
                1060                1065                1070

Thr Phe Glu Glu Thr Ala Val Arg Ala Thr Pro Thr Pro Ile Gly
                1075                1080                1085

Leu Ile Ala Arg Asp Ser Pro His Val Leu Val Ala Leu Thr Arg His
                1090                1095                1100

Thr Lys Ala Met Val Tyr Tyr Thr Val Val Phe Asp Ala Val Thr Ser
1105                1110                1115                1120

Ile Ile Ala Asp Val Glu Lys Val Asp Gln Ser Ile Leu Thr Met Phe
                1125                1130                1135

Ala Thr Thr Val Pro Thr Lys Met Gln Asn Ser Leu Tyr Val His Arg
                1140                1145                1150
```

```
Asn Ile Phe Leu Pro Val Ser Lys Thr Gly Phe Tyr Thr Asp Met Gln
        1155                1160                1165
Glu Phe Tyr Asp Arg Cys Leu Pro Gly Asn Ser Phe Val Leu Asn Asp
    1170                1175                1180
Phe Asp Ala Val Thr Met Arg Leu Arg Asp Asn Glu Phe Asn Leu Gln
1185                1190                1195                1200
Pro Cys Arg Leu Thr Leu Ser Asn Leu Asp Pro Val Pro Ala Leu Ile
        1205                1210                1215
Lys Asn Glu Ala Gln Asn Phe Leu Ile Pro Val Leu Arg Thr Ala Cys
        1220                1225                1230
Glu Arg Pro Arg Ile Pro Gly Leu Leu Glu Asn Leu Val Ala Met Ile
        1235                1240                1245
Lys Arg Asn Met Asn Thr Pro Asp Leu Ala Gly Thr Val Asp Ile Thr
        1250                1255                1260
Asn Met Ser Ile Ser Ile Val Asp Asn Phe Phe Ser Ser Phe Val Arg
1265                1270                1275                1280
Asp Glu Val Leu Leu Asp His Leu Asp Cys Val Arg Ala Ser Ser Ile
        1285                1290                1295
Gln Ser Phe Ser Asp Trp Phe Ser Cys Gln Pro Thr Ser Ala Val Gly
        1300                1305                1310
Gln Leu Ala Asn Phe Asn Phe Ile Asp Leu Pro Ala Phe Asp Thr Tyr
        1315                1320                1325
Met His Met Ile Lys Arg Gln Pro Lys Ser Arg Leu Asp Thr Ser Ile
        1330                1335                1340
Gln Ser Glu Tyr Pro Ala Leu Gln Thr Ile Val Tyr His Pro Lys Val
1345                1350                1355                1360
Val Asn Ala Val Phe Gly Pro Val Phe Lys Tyr Leu Thr Thr Lys Phe
        1365                1370                1375
Leu Ser Met Val Asp Ser Ser Lys Phe Phe Phe Tyr Thr Arg Lys Lys
        1380                1385                1390
Pro Glu Asp Leu Gln Glu Phe Phe Ser Asp Leu Ser Ser His Ser Asp
        1395                1400                1405
Tyr Glu Ile Leu Glu Leu Asp Val Ser Lys Tyr Asp Lys Ser Gln Ser
        1410                1415                1420
Asp Phe His Phe Ser Ile Glu Met Ala Ile Trp Glu Lys Leu Gly Leu
1425                1430                1435                1440
Asp Asp Ile Leu Ala Trp Met Trp Ser Met Gly His Lys Arg Thr Ile
        1445                1450                1455
Leu Gln Asp Phe Gln Ala Gly Ile Lys Thr Leu Ile Tyr Tyr Gln Arg
        1460                1465                1470
Lys Ser Gly Asp Val Thr Thr Phe Ile Gly Asn Thr Phe Ile Ile Ala
        1475                1480                1485
Ala Cys Val Ala Ser Met Leu Pro Leu Asp Lys Cys Phe Lys Ala Ser
        1490                1495                1500
Phe Cys Gly Asp Asp Ser Leu Ile Tyr Leu Pro Lys Gly Leu Glu Tyr
1505                1510                1515                1520
Pro Asp Ile Gln Ala Thr Ala Asn Leu Val Trp Asn Phe Glu Ala Lys
        1525                1530                1535
Leu Phe Arg Lys Lys Tyr Gly Tyr Phe Cys Gly Lys Tyr Ile Ile His
        1540                1545                1550
His Ala Asn Gly Cys Ile Val Tyr Pro Asp Pro Leu Lys Leu Ile Ser
        1555                1560                1565
Lys Leu Gly Asn Lys Ser Leu Val Gly Tyr Glu His Val Glu Glu Phe
```

```
                1570             1575             1580
Arg Ile Ser Leu Leu Asp Val Ala His Ser Leu Phe Asn Gly Ala Tyr
1585             1590             1595             1600

Phe His Leu Leu Asp Asp Ala Ile His Glu Leu Phe Pro Asn Ala Gly
                1605             1610             1615

Gly Cys Ser Phe Val Ile Asn Cys Leu Cys Lys Tyr Leu Ser Asp Lys
                1620             1625             1630

Arg Leu Phe Arg Ser Leu Tyr Ile Asp Val Ser Lys
        1635             1640
```

```
<210> SEQ ID NO 23
<211> LENGTH: 1139
<212> TYPE: DNA
<213> ORGANISM: Cucumber green mottle mosaic virus
<220> FEATURE:
<223> OTHER INFORMATION: DNA sequnece encoding coat protein of CGMMV
      strain SH

<400> SEQUENCE: 23
aattcggctt ctgtaggggt ggtgctactg ttgctctggt tgacacaagg atgcattctg      60
ttgcagaggg aactatatgc aaattttcag ctcccgccac cgtccgcgaa ttctctgtta     120
ggttcatacc taattatcct gtcgtggctg cggatgccct tcgcgatcct tggtctttat     180
ttgtgagact ctctaatgtg ggcattaaag atggtttcca tcctttgact ttagaggtcg     240
cttgtttagt cgctacaact aactctatta tcaaaaaggg tcttagagct tctgtagtcg     300
agtctgtcgt ctcttccgat cagtctattg tcctagattc cttgtccgag aaagttgaac     360 cttttctttga caaagttcct atttcagcgg ctgtaatggc aagagatccc agttataggt     420
ctaggtcaca gtctgtcggt ggtcgtggta agcggcattc taaacctcca aatcggaggt     480
tggactctgc ttctgaagag tccagttctg tttcttttga agatggctta caatccgatc     540
acacctagca aacttattgc gtttagtgct tcatatgttc ccgtcaggac tttacttaat     600
tttctagttg cttcacaagg taccgctttt cagactcaag cgggaagaga ttctttccgc     660
gagtccctgt ctgcgttacc ctcgtctgtc gtagatatta attctagatt cccagatgcg     720 ggttttacg ctttcctcaa cggtcctgtg ttgaggccta tcttcgtttc gcttctcagc      780
tccacggata cgcgtaatag ggtcattgag gttgtagatc ctagcaatcc tacgactgct     840
gagtcgctta acgctgtaaa gcgtactgat gacgcgtcta cagccgctag ggccgagata     900
gataatttaa tagagtctat ttctaagggt tttgatgttt acgatagggc ttcatttgaa     960
gccgcgtttt cggtagtctg gtcagaggct accacctcga aagcttagtt tcgagggtct    1020
tctgatggtg gtgcacacca aagtgcatag tgctttcccg ttcacttaaa tcgaacggtt    1080
tgctcattgg tttgcggaaa cctctcacgt gtgacgttga agtttctatg ggcaagccg     1139
```

```
<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: primer
      97G01

<400> SEQUENCE: 24
aggtgtcagt ggagaactca ttga                                             24

<210> SEQ ID NO 25
<211> LENGTH: 17
```

```
<212> TYPE: DNA
<213> ORGANISM: Artificial Sequence
<220> FEATURE:
<223> OTHER INFORMATION: Description of Artificial Sequence: primer
      97G02

<400> SEQUENCE: 25
ggcgttgtgg tttgtgg                                                       17

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: primer
      97G03

<400> SEQUENCE: 26
ctgtaggggt ggtgctactg t                                                  21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: primer
      97G18

<400> SEQUENCE: 27
gcccatagaa acttcaacgt c                                                  21

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: primer
      98A88

<400> SEQUENCE: 28
ccatggagaa ttcgctgtat gtcc                                               24

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: primer
      98A86

<400> SEQUENCE: 29
cgagctctcg actgacacct tac                                                23

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: primer
      98A84

<400> SEQUENCE: 30
ccatggcaaa cattaatgaa c                                                  21

<210> SEQ ID NO 31
<211> LENGTH: 21
<212> TYPE: DNA
```

-continued

```
<213> ORGANISM: Artificial Sequence
<220> FEATURE:
<223> OTHER INFORMATION: Description of Artificial Sequence: primer
      98A85

<400> SEQUENCE: 31
caaccatggc aaacattaat g                                              21

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: primer
      98G63

<400> SEQUENCE: 32
taacagggag gaaaatatta cg                                             22

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: primer
      98L99

<400> SEQUENCE: 33
gagctcggat ccactagtaa cggc                                           24

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: primer
      98L107

<400> SEQUENCE: 34
tagagctctt gaagctaagc aaattccg                                       28

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: primer
      98L108

<400> SEQUENCE: 35
ttcaagagct ctaatcaccg aagacaaagg c                                   31

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: primer
      98L102

<400> SEQUENCE: 36
gaattatatc gattatctat cggc                                           24

<210> SEQ ID NO 37
<211> LENGTH: 27
<212> TYPE: DNA
<213> ORGANISM: Artificial Sequence
```

```
<220> FEATURE:
<223> OTHER INFORMATION: Description of Artificial Sequence: primer
      98L103

<400> SEQUENCE: 37
gataatcgat ataattcttc atctgcc                                          27

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: primer
      98L104

<400> SEQUENCE: 38
aactagtaat tgatgatctg ttcaagaag                                        29

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: primer
      98L105

<400> SEQUENCE: 39
aattactagt ttccggaagc aagcagctca g                                     31

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: primer
      98L106

<400> SEQUENCE: 40
gccctctaga tgcatgctcg ag                                               22

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: primer
      97G40

<400> SEQUENCE: 41
ctagagtttt aatttttata attaaacaaa                                       30

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence: primer
      97G41

<400> SEQUENCE: 42
tcaaaattaa aaatattaat tgtttgttg ttgttg                                 36

<210> SEQ ID NO 43
<211> LENGTH: 36
<212> TYPE: DNA
<213> ORGANISM: Artificial Sequence
<220> FEATURE:
```

```
<223> OTHER INFORMATION: Description of Artificial Sequence: primer
      97G42

<400> SEQUENCE: 43
caacaacaac aacaacaaac aattttaaaa caacac                              36

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: primer
      97G43

<400> SEQUENCE: 44
ttgttgtttg ttaaaatttt gttgtggtac                                    30

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: primer 1

<400> SEQUENCE: 45
cgagctcatc tcgttagtca gc                                            22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: primer 2

<400> SEQUENCE: 46
gggatccacg tctggacagg                                               20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: primer 3

<400> SEQUENCE: 47
ctctagaatc tcgttagtca gc                                            22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: primer 4

<400> SEQUENCE: 48
aggatcctac acgaacctat c                                             21

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: primer 5

<400> SEQUENCE: 49
aggatccatt gcggtaacac aac                                           23
```

```
<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: primer 6

<400> SEQUENCE: 50
tagatctatt gcggtaacac aac                                          23

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: primer 7

<400> SEQUENCE: 51
tagatctgtg tgattctgg                                               19

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: primer 8

<400> SEQUENCE: 52
aggatccgtg tgattctgg                                               19

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: primer 9

<400> SEQUENCE: 53
aggatccgtg tacgtaagtt tc                                           22

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: primer 10

<400> SEQUENCE: 54
tagatctgtg tacgtaagtt tc                                           22

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: primer 11

<400> SEQUENCE: 55
tagatctgtg atacctgcag                                              20

<210> SEQ ID NO 56
<211> LENGTH: 20
<212> TYPE: DNA
<213> ORGANISM: Artificial Sequence
<220> FEATURE:
```

-continued

<223> OTHER INFORMATION: Description of Artificial Sequence: primer 12

<400> SEQUENCE: 56
aggatccgtg atacctgcag                                             20

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: primer 13

<400> SEQUENCE: 57
cgagctcatc tcgttagtca gctagc                                      26

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: primer 14

<400> SEQUENCE: 58
aggatccttt gtgcctctgt acatg                                       25

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: primer 15

<400> SEQUENCE: 59
ctctagaatc tcgttagtca gctagc                                      26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: primer 16

<400> SEQUENCE: 60
aggatccatc aaccctaaat tgagcc                                      26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: primer 17

<400> SEQUENCE: 61
aggatccagc agggaaataa gtacgc                                      26

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: primer 18

<400> SEQUENCE: 62
aggatccggt atggacaaaa tcagc                                       25

```
<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: primer 19

<400> SEQUENCE: 63
aggatccatt gcggtaacac aacctctc                                          28

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: primer 20

<400> SEQUENCE: 64
tagatctgtg tgattctgga aaag                                              24

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: primer 21

<400> SEQUENCE: 65
tagatctgtg atacctgcac atcaac                                            26

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: primer 22

<400> SEQUENCE: 66
aggatccgtg tacgtaagtt tctgcttc                                          28

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: primer 23

<400> SEQUENCE: 67
ctctagaatc tcgttagtca gctagc                                            26

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: primer 24

<400> SEQUENCE: 68
aggatccagc agggaaataa gtacgc                                            26
```